(12) United States Patent
Lim

(10) Patent No.: US 11,156,616 B2
(45) Date of Patent: Oct. 26, 2021

(54) METHODS OF DETECTING THERAPEUTIC EXOSOMES

(75) Inventor: Sai Kiang Lim, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 324 days.

(21) Appl. No.: 13/984,203

(22) PCT Filed: Feb. 10, 2012

(86) PCT No.: PCT/SG2012/000039
§ 371 (c)(1),
(2), (4) Date: Oct. 15, 2013

(87) PCT Pub. No.: WO2012/108842
PCT Pub. Date: Aug. 16, 2012

(65) Prior Publication Data
US 2014/0031256 A1    Jan. 30, 2014

(30) Foreign Application Priority Data

Feb. 11, 2011 (SG) ............................. 201100995-8

(51) Int. Cl.
*G01N 33/53* (2006.01)
*G01N 33/68* (2006.01)
*G01N 33/50* (2006.01)

(52) U.S. Cl.
CPC ......... *G01N 33/68* (2013.01); *G01N 33/5005* (2013.01); *G01N 33/6848* (2013.01); *G01N 2570/00* (2013.01)

(58) Field of Classification Search
None
See application file for complete search history.

(56) References Cited

FOREIGN PATENT DOCUMENTS

| WO | 2001/082958 | | 11/2001 |
|---|---|---|---|
| WO | 2006/007529 | | 1/2006 |
| WO | 2006/007529 | A2 | 1/2006 |
| WO | 2007/015174 | | 2/2007 |
| WO | 2009/100029 | A1 | 8/2009 |
| WO | 2009/105044 | | 8/2009 |
| WO | 2009/105044 | A1 | 8/2009 |
| WO | 2010/056337 | A2 | 5/2010 |
| WO | 2011/000551 | A1 | 1/2011 |

OTHER PUBLICATIONS

Liu et al., Clinic Review Allergic Immunology, 2014, vol. 47, pp. 136-147.*
Frangogiannis et al (Cardiovascular Research, 2002, vol. 53, pp. 31-47).*
Chaput et al., "Exosomes: immune properties and potential clinical implementation", Semin Immunopathol, 33(5): 419-440 (2011).
Chavez-Munoz et al., "Profile of Exosomes Related Proteins Released by Differentiated Human Keratinocytes", 221(1): 221-231 (2009).
Clayton et al., "Analysis of antigen presenting cell derived exosomes, based on immuno-magnetic isolation and flow cytometry", 247(1-2): 163-174 (2001).
Clayton et al., "Antigen-presenting cell exosomes are protected from complement-mediated lysis by expression of CD55 and CD59", Eur J Immunol, 33(2): 522-531 (2003).
Jeong et al., "Identification of heat shock protein 70 in canine reticulocytes and matyre erythrocytes", Japanese Journal of Veterinary Research, 53(1-2): 37-46 (2005).
Mitchell et al., "Can urinary exosomes act as treatment response markers in prostate cancer", J Transl Med, 7(4): 1-13 (2009).
Stefano et al., "The surface-exposed chaperone, Hsp60, is an agonist of the microglial TREM2 receptor", J Neurochem, 110(1): 284-294 (2009).
Anand P.K., "Exosomal membrane molecules are potent immune response modulators", Communicative & Integrative Biology 3(5):405-408 (2010).
R.C. Lai, F. Arslan, M.M. Lee, N.S. Sze, A. Choo, T.S. Chen, M. Saito-Tellez, L. Timmers, C.N. Lee, R.M. El Oakley, G. Pasterkamp, D.P. de Kleijn, S.K. Lim, Exosome secreted by MSC reduces myocardial ischemia/reperfusion injury, Stem Cell Res, 4 (2010) 214-222.
Pan, B.T. & Johnstone, R.M. Fate of the transferrin receptor during maturation of sheep reticulocytes in vitro: selective externalization of the receptor. Cell 33, 967-978 (1983).
Thery, C., Ostrowski, M. & Segura, E. Membrane vesicles as conveyors of immune responses. Nat Rev Immunol9, 581-593 (2009).
Fevrier, B. & Raposo, G. Exosomes: endosomal-derived vesicles shipping extracellular messages. Curr Opin Cell Biol16, 415-421 (2004).
Keller, S., Sanderson, M.P., Stoeck, A. & Altevogt, P. Exosomes: from biogenesis and secretion to biological function. Immunol Lett 107, 102-108 (2006).
Zitvogel, L., et al. Eradication of established murine tumors using a novel cell-free vaccine: Dendritic cell-derived exosomes. Nature Medicine 4, 594-600 (1998).
Wolfers, J. et al, Tumor-derived exosomes are a source of shared tumor rejection antigens for CTL cross-priming. Nature Medicine 7, 297-303 (2001).
Skokos, D., et al. Mast cell-derived exosomes induce phenotypic and functional maturation of dendritic cells and elicit specific immune responses in vivo. Journal of Immunology 170, 3037-3045 (2003).

(Continued)

*Primary Examiner* — Celine X Qian
(74) *Attorney, Agent, or Firm* — Nixon Peabody LLP; Mark J. FitzGerald

(57) ABSTRACT

We describe a method of detecting a therapeutic exosome, the method comprising detecting an activity of an exosome. The activity may be selected from the group consisting of: (a) immunodulatory activity; (b) complement inhibition activity; (c) proteasome activity; (d) glycolytic enzyme activity; (e) anti-oxidative activity; (f) extracellular matrix (ECM) modifying activity; (g) NT5E (CD73) ecto-5'-ectonucleotidase activity; (h) ion homeostasis activity; and (i) chaperone activity. If the exosome is detected as having one or more such activities, the exosome is likely to comprise a therapeutic exosome having therapeutic activity.

3 Claims, 21 Drawing Sheets
Specification includes a Sequence Listing.

(56) References Cited

OTHER PUBLICATIONS

Taylor, D.D. & Gercel-Taylor, C. Tumour-derived exosomes and their role in cancer-associated T-cell signalling defects. British Journal of Cancer 92, 305-311 (2005).
Chen, T.S., et al. Mesenchymal stem cell secretes microparticles enriched in pre-microRNAs. Nucleic Acids Res 38, 215-224 (2010).
Lai, R.C., et al. Derivation and characterization of human fetal MSCs: an alternative cell source for large-scale production of cardioprotective microparticles. J Mol Cell Cardiol 48, 1215-1224 (2010).
Sze, S.K., et al. Elucidating the secretion proteome of human embryonic stem cell-derived mesenchymal stem cells. Mol Cell Proteomics 6, 1680-1689 (2007).
Chen et al., "Enabling a robust scalable manufacturing process for therapeutic exosomes through oncogenic immortalization of human ESC-derived MSCs", J Transl Med, 9:47 (2011).
Obata "In vivo cardiac microdialysis to estimate ectonucleotidase activity", Japanese Journal of Electrocardiology 29:273-280 (2009) (Abstract included).
Abdul-Hai et al., "Improved survival following induction of GVHD following lipopolysaccharide immunization", Exp Hematol 34(4) 549-553 (2008).
Biswas et al., "Endotoxin tolerance: new mechanisms, molecules and clinical significance", Trends Immunol 30(10) 475-487 (2009).
Dalpke et al., "Differential effects of CpG-DNA in Toll-like receptor-2/-4/-9 tolerance and cross-tolerance", Immunology 116(2) 203-212 (2005).
Lorenz et al., "Association of TLR4 mutations and the risk for acute GVHD after HLA-matched-sibling hematopoietic stem cell transplantation", Biol Blood Marrow Transplant 7(7) 384-387 (2001).
Matsushita et al., "Endotoxin tolerance attenuates airway allergic inflammation in model mice by suppression of the T-cell stimulatory effect of dendritic cells", Int Immunol 22(9) 739-747 (2010).
Platzbecker et al., "Induction of Toll-like receptor 2 and 4 expression on CD4+ and CD8+ T cells in G-CSF-mobilized unrelated peripheral blood stem cell grafts during leukapheresis: impact on patient outcome", Leukemia 22(7) 1438-1440 (2008).
Sato et al., "A variety of microbial components induce tolerance to lipopolysaccharide by differentially affecting MyD88-dependent and -independent pathways", Int Immunol 14(7) 783-791 (2002).
Shin et al., "Innate immunity and transplantation tolerance: the potential role of TLRs/NLRs in GVHD", Korean J Hematol 46(2) 69-79 (2011).
West et al., "Endotoxin tolerance: a review", Crit Care Med 30(1 Suppl) S64-S73 (2002).
Clayton et al., "Cancer exosomes express CD73, and support immune suppression through adenosine generation", Immunology 131; 44 (2010). Abstract.

* cited by examiner

METHODS OF DETECTING THERAPEUTIC EXOSOMES

CROSS REFERENCE TO RELATED APPLICATIONS

This application is a 35 U.S.C. § 371 National Phase Entry Application of International Application No. PCT/SG2012/000039 filed Feb. 10, 2012, which designates the U.S., and which claims benefit of Singapore Patent Application No. 201100995-8 filed Feb. 11, 2011, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 14, 2017, is named 049595-078830-US SL.txt and is 3,685 bytes in size.

FIELD

The present invention relates to the fields of medicine, cell biology, molecular biology and genetics. This invention relates to the field of medicine.

BACKGROUND

Exosomes were once thought to be "trash bags" for cells to discard unwanted proteins[1]. However, exosomes are increasingly viewed as having important physiological function particularly in cellular communication.

Exosomes are bi-lipid membrane vesicles of 50-100 ηm that are secreted by many cell types[2]. They belong to a class of secreted cellular products known as microparticles which broadly encompasses all secreted membrane vesicles. Other than exosomes, microparticles include microvesicles (100-1000 ηm), ectosomes (50-200 ηm), membrane particles (50-80 ηm), exosome-like vesicles (20-50 ηm) and apoptotic vesicles (50-500 ηm). The major distinguishing parameter for these different classes of microparticles is their size and the best defined class is the exosomes.

Exosomes have a density in sucrose of 1.10 to 1.19 g/ml, sedimented at 100,000 g, has a cholesterol-rich lipid membrane containing sphingomyelin, ceramide, lipid rafts and exposed phosphatidylserine. The process of exosome biogenesis is complex and involves complex intracellular membrane trafficking and cargo sorting through the biosynthetic and endocytotic pathways. As evidence of this complex biogenesis, the hallmark features of exosomes are markers of the endoplasmic reticulum and the endosomes such as Alix, Tsg101, Rab proteins, etc. Exosomes are stored in multivesicular bodies prior to release via fusion of the multivesicular bodies (MVBs) with the plasma membrane.

Exosomes have been shown to mediate intercellular communication particularly in immune or tumor cells[3-8]. Recently we extended this function to include tissue repair when we reported that exosomes secreted by human ESC-derived MSCs reduced infarct size by about 50% in a mouse model of myocardial ischemia reperfusion (MI/R) injury[9,10]. These exosomes were purified as a population of homogenously sized microparticles of about 50-100 ηm in diameter by size exclusion on HPLC and they carry both protein and RNA load[9,11,12].

However, the mechanism/s underlying this cardioprotective effect by MSC exosomes has yet to be elucidated. Part of the reason could be attributed to a deficiency in our understanding of the biological potency of exosomes in general. Despite extensive proteomic and RNA profiling of exosomes from various cell types and biological fluids, the biological potency of the proteins and RNAs in exosomes remains largely uninvestigated. Most studies to date on the biological potency are limited to the immune responses that are elicited by exosomes from immune cells, particularly the dendritic cells[2] but the molecular or biochemical basis of these biological responses have yet to be elucidated.

SUMMARY

To address this deficiency, we performed a comprehensive proteomic profiling of HPLC-purified exosome to first identify proteins present in these exosomes and then using these proteins to predict the types of biological activity or potential in the exosomes. This was then validated by either biochemical or cellular assays.

A total of 866 unique gene products were detected and they could be functionally clustered into 32 over-represented biological processes indicating that exosomes have the potential to exert a wide spectrum of biochemical or cellular effects. To evaluate this potential, we selected proteins for which assays to assess either their biochemical and/or cellular activities are available and that together, would demonstrate the wide spectrum of biochemical and cellular potential in exosomes, and provide candidate molecular mechanisms for the cardioprotective properties of MSC exosomes.

The proteins investigated here include glycolytic enzymes for the breakdown of glucose to generate ATP and NADH, PFKB3 that increases glycolysis, CD73 that hydrolyses AMP to adenosine capable of activating signaling cascades through adenosine receptors, CD59 that inhibits the formation of membrane attack complex (MAC) and 20S proteasome.

According to a $1^{st}$ aspect of the present invention, we provide a method of detecting a therapeutic exosome. The method may comprise detecting an activity of an exosome. The method may comprise immunodulatory activity. It may comprise complement inhibition activity. It may comprise proteasome activity. It may comprise glycolytic enzyme activity. It may comprise anti-oxidative activity. It may comprise extracellular matrix (ECM) modifying activity. It may comprise NT5E (CD73) ecto-5'-ectonucleotidase activity. It may comprise ion homeostasis activity. It may comprise chaperone activity. It may comprise any one or more of the above.

The activity may comprise immunodulatory activity. The immunodulatory activity may be detected by detecting activity of a protein set out in Table D10.

The activity may comprise complement inhibition activity. The complement inhibition activity may be detected by detecting activity of a protein set out in Table D1.

The activity may comprise proteasome activity. The proteasome activity may be detected by detecting activity of one or more, preferably all, proteins set out in Table D2.

The activity may comprise glycolytic enzyme activity. The glycolytic enzyme activity may be detected by detecting activity of one or more, preferably all, proteins set out in Table D3.

The activity may comprise anti-oxidative activity. The anti-oxidative activity may be detected by detecting activity of one or more, preferably all, proteins set out in Table D4.

The activity may comprise extracellular matrix (ECM) modifying activity. The extracellular matrix (ECM) modifying activity may be detected by detecting activity of one or more, preferably all, proteins set out in Table D5.

The activity may comprise NT5E (CD73) ecto-5'-ecto-nucleotidase activity. The NT5E (CD73) ecto-5'-ectonucleotidase activity may be detected by detecting activity of one or more, preferably all, proteins set out in Table D6.

The activity may comprise ion homeostasis activity. The ion homeostasis activity may be detected by detecting activity of one or more, preferably all, proteins set out in Table D7.

The activity may comprise chaperone activity. The chaperone activity may be detected by detecting activity of one or more, preferably all, proteins set out in Table D8.

The activity may comprise immunomodulatory activity. The immunomodulatory activity may be detected by detecting activity of one or more, preferably all, proteins set out in Table D10.

If an activity is detected, the exosome may be likely to be capable of inhibiting complement mediated cell lysis. It may also, alternatively or in addition, be capable of reducing infarct size for example as assayed in a mouse or pig model of myocardial ischemia and reperfusion injury, or which is capable of reducing oxidative stress for example as assayed in an in vitro assay of hydrogen peroxide ($H_2O_2$)-induced cell death. It may have both the above activities.

If an activity is detected, the exosome may be likely to comprise a therapeutic exosome having therapeutic activity.

The therapeutic activity may comprise cardioprotective activity.

The therapeutic activity may be against one or more diseases selected from the group consisting of: cardiac failure, bone marrow disease, skin disease, burns and degenerative diseases such as diabetes, Alzheimer's disease, Parkinson's disease, cancer, myocardial infarction, a cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterised by initial injury inducing inflammation and immune dysregulation leading to chronic tissue remodeling including fibrosis and loss of function, renal ischemic injury, cystic fibrosis, sinusitis and rhinitis or an orthopaedic disease.

There is provided, according to a $2^{nd}$ aspect of the present invention, a method comprising the steps of: (a) isolating an exosome from a mesenchymal stem cell conditioned medium (MSC-CM), optionally comprising separating the exosome from other components based on molecular weight, size, shape, composition or biological activity, and (b) detecting an activity as set out above in the isolated exosome, preferably by detecting the activity of one or more proteins as set out above.

We provide, according to a $3^{rd}$ aspect of the present invention, a method of producing an exosome, the method comprising: (a) obtaining a mesenchymal stem cell conditioned medium (MSC-CM); (b) concentrating the mesenchymal stem cell conditioned medium, for example by ultrafiltration over a >1000 kDa membrane; (c) subjecting the concentrated mesenchymal stem cell conditioned medium to size exclusion chromatography, such as using a TSK Guard column SWXL, 6×40 mm or a TSK gel G4000 SWXL, 7.8×300 mm column; (d) selecting UV absorbant fractions, for example, at 220 nm, that exhibit dynamic light scattering, such as detected by a quasi-elastic light scattering (QELS); in which step (d) for example comprises collecting fractions which elute with a retention time of 11-13 minutes, such as 12 minutes; and detecting an activity as set out above in the exosome, preferably by detecting the activity of one or more proteins as set out above.

As a $4^{th}$ aspect of the present invention, there is provided a method of detecting whether an exosome comprises therapeutic activity, the method comprising detecting an enzymatic activity as set out above, in which if the enzymatic activity is detected, then the exosome comprises therapeutic activity.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 3A is a schematic diagram of glycolysis.

FIG. 3B is a Western blot analysis of conditioned medium (CM) and exosome (Exo) for geraldehyde phosphate dehydrogenase (GAPDH), phosphoclycerate kinase (PGK), pyruvate kinase m2 isoform ($PKm_2$) and pPFKFB3.

FIG. 3C is a Enzymatic activities of GAPDH, PGK and $PKm_2$ in MSC exosome were determined by the production of ATP or pyruvate using commercially available assay kit. One unit (U) enzyme activity is defined as the activity to generate 1 μmole product per minute at 37° C.

FIG. 3D. Effect of exosome on ATP production in oligomycin-treated cells. H9C2 cardiomyocytes were washed twice with Tyrode's buffer and then incubated in Tyrode's buffer containing 20 μmol of a mitochondrial inhibitor, oligomycin, 6 mmol glucose, and with or without 0.1 μg/ml exosomes for 15, 30 and 60 minutes. Cellular ATP concentration was measured using ATPlite 1 step luminescence ATP detection assay system and normalized to that of sample without exosomes at 15 minutes. *p=0.0173, **p=0.0090

FIG. 4A. Western blot analysis of MSC conditioned medium (CM) and exosome (Exo) using an antibody specific for PMSA 1-7 peptides.

FIG. 4B. Proteasome activity in MSC exosome was determined using a commercially available proteasome activity assay kit (Millipore). Proteasome activity was measured by the rate of degradation of a fluorogenic peptide in the absence or presence of lactacystin, a proteasome inhibitor. One unit (U) enzyme activity is defined as the activity to generate 1 μmole product per minute at 37° C. *p=0.00023

FIG. 5A. Western blot analysis of MSC CM and exosome for CD73 using a specific antibody.

FIG. 5B. CD73 activity in conditioned medium (CM) and exosomes (Exo) was measured by the production of phosphate ion from the hydrolysis of AMP.

FIG. 5C. H9C2 cells were serum starved overnight and then incubated with medium with or without 1 mM theophylline for one hour. The cells were then exposed for 5 min to medium that had been pre-incubated for 30 minutes with 50 μM AMP, 0.1 μg/mL exosome or AMP and exosome. The cells were then harvested and lysed. 10 μg total proteins were immunoblotted using 1:2000 dilution of rabbit anti-pERK 1/2, 1:2000 dilution of rabbit anti ERK1/2, 1:500 dilution rabbit anti-pAKT or 1:500 dilution of rabbit anti AKT.

FIG. 6A. Western blot analysis of MSC conditioned medium (CM) and exosome (Exo) using a CD59-specific antibody.

FIG. 6B. SRBCs were washed and then re-suspended in PBS with C5b6 and C7 in the presence or absence of exosome. The mixture was incubated at 37° C. for 15 min before C8 and C9 were added with or without a blocking CD59 antibody for additional 30 min incubation. The cells were centrifuged and the amount of hemoglobin released by the lysed SRBC in the supernatant was measured by absorbance at 415 nm. The positive control (total hemolysis) was supernatant from cells completely lysed with Triton X-100. The negative control is the sample without addition of complement components. The absorbance value of positive control was normalized to 100%*p=2.8E-06, **p=3.51E-08.

DETAILED DESCRIPTION

Figure 1:
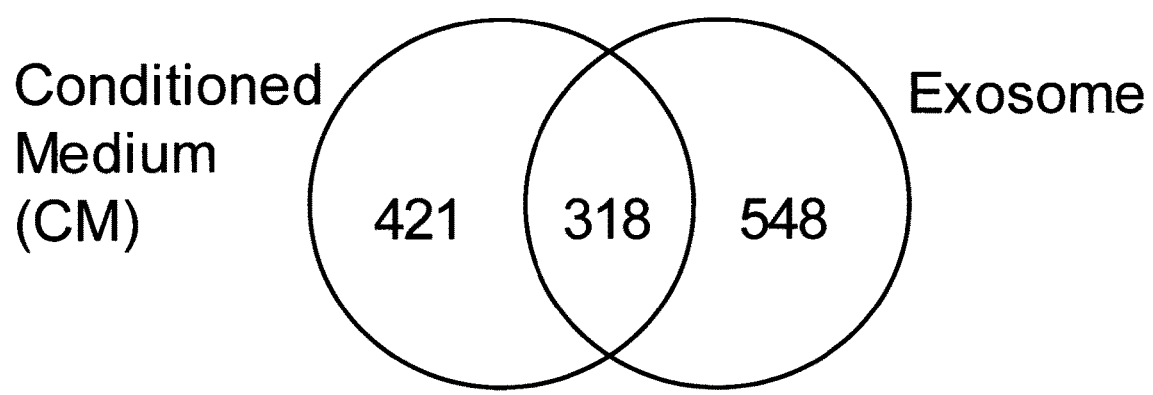
FIG. 1 is a diagram showing the intersection of the 739 proteins previously identified in MSC conditioned medium versus the 866 proteins identified in purified exosomes.

Mammalian cells secrete exosomes that contain proteins and RNAs. Hypothetically, these exosomes could be harvested and purified from healthy cells to be used to replenish and bolster the cellular resources in diseased or distressed cells, and enable these cells to initiate recovery and repair. For example, we have demonstrated that exosomes from human embryonic stem cell-derived mesenchymal stem cells could rescue cardiomyocytes from cell death after acute myocardial ischemia-reperfusion injury. Here we describe the biochemical properties of these exosomes. These properties could be used to identify, select or assess exosome preparation for therapeutic potential in treating diseased or distressed cells.

Cells in distress as a consequence of injury or disease often share similar cellular dysfunctions. They have increased mitochondrial membrane permeability resulting in reduced ATP and NADH production, increased ROS level and loss in ion homeostasis including Na, Ca, K and Cl. There are also accumulation of denatured proteins leading to ER stress and formation of inclusion bodies and excessive innate immune response. To begin the process of recovery and repair, cells must first correct these cellular dysfunctions. Since exosomes are secreted phospholipid vesicles containing proteins and RNAs, they could potentially deliver enzymes and RNA that could rapidly initiate the necessary cellular activities to correct these cellular dysfunctions.

Here we describe the biochemical properties of therapeutic exosomes. These biochemical properties include
 a. Inhibition of complement activity (Table D1 below)
 b. proteasome activity to degrade denature proteins (Table D2 below)
 c. glycolytic enzymes to generate ATP and NADH (Table D3 below)
 d. pentose phosphate pathway enzymes to generate NADPH
 e. anti-oxidative activity (Table D4 below)
 f. MMP/TIMP activity (Table D5 below)
 g. CD73 ecto-5'-ectonucleotidase activity to activate survival signaling pathway (Table D6 below)
 h. ATPase membrane channels or transporters to restore ion homeostasis e.g. calcium, sodium, proton, potassium and chloride channels (Table D7 below)
 i. chaperone activity to maintain protein structural integrity (Table D8 below)

Potentially therapeutic exoosmes should not only have the proteins for these biochemical activies, the proteins must be enzymatically active. The enzymatic activity of these proteins could therefore be surrogate markers for the therapeutic efficacy of an exosome preparation.

We therefore provide a number of biochemical assays to define, identify and assess therapeutic exosomes.

Assays for Therapeutic Exosomes

We describe biological properties, in particular biochemical properties of a particle which is derivable from a mesenchymal stem cell (MSC), for example an exosome.

According to the methods and compositions described here, an exosome which comprises one or more of: (a) complement inhibition activity; (b) proteasome activity; (c) glycolytic enzyme activity; (d) anti-oxidative activity; (e) extracellular matrix (ECM) modifying activity; (f) NT5E (CD73) ecto-5'-ectonucleotidase activity; (g) ion homeostasis activity; (h) chaperone activity, may comprise therapeutic activity; and (i) immunodulatory activity.

An exosome comprising such properties may be therapeutic in nature against a number of diseases, as described below, in other words be a therapeutic exosome. Where the term "exosome" is used in this document, this should be understood to include "therapeutic exosome" as well, where the context permits.

The exosome may be derivable from the MSC by any of several means, for example by secretion, budding or dispersal from the MSC. For example, the exosome may be produced, exuded, emitted or shed from the MSC. Where the MSC is in cell culture, the exosome may be secreted into the cell culture medium.

The exosome may in particular comprise a vesicle. The therapeutic exosomes described here may comprise any one or more of the properties of the exosomes described herein.

The exosomes may comprise vesicles or a flattened sphere limited by a lipid bilayer. The exosomes may comprise diameters of 40-100 nm. The exosomes may be formed by inward budding of the endosomal membrane. The exosomes may have a density of ~1.13-1.19 g/ml and may float on sucrose gradients. The exosomes may be enriched in cholesterol and sphingomyelin, and lipid raft markers such as GM1, GM3, flotillin and the src protein kinase Lyn. The exosomes may comprise one or more proteins present in mesenchymal stem cells or mesenchymal stem cell conditioned medium (MSC-CM), such as a protein characteristic or specific to the MSC or MSC-CM.

We provide a exosomes which comprises one or more genes found in MSCs or medium which is conditioned by culture of MSCs, and which comprises therapeutic activity. Such therapeutic exosomes may be identified by detecting exosomes which display one or more activities selected from the group consisting of: (a) complement inhibition activity; (b) proteasome activity; (c) glycolytic enzyme activity; (d) anti-oxidative activity; (e) extracellular matrix (ECM) modifying activity; (0 NT5E (CD73) ecto-5'-ectonucleotidase activity; (g) ion homeostasis activity; (h) chaperone activity; and (i) immunodulatory activity.

The exosomes may comprise molecules secreted by the MSC. Such an exosome, and combinations of any of the molecules comprised therein, including in particular proteins or polypeptides, may be used to supplement the activity of, or in place of, the MSCs or medium conditioned by the MSCs for the purpose of for example treating or preventing a disease.

The exosomes may comprise a cytosolic protein found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. In particular, the exosomes may comprise one or more tetraspanins. The exosomes may comprise mRNA and/or microRNA.

The term "particle", which includes an exosome, as used in this document may be taken to mean a discrete entity. The particle may be something that is isolatable from a mesenchymal stem cell (MSC) or mesenchymal stem cell conditioned medium (MSC-CM). The particle may be responsible for at least an activity of the MSC or MSC-CM. The particle may be responsible for, and carry out, substantially most or all of the functions of the MSC or MSC-CM. For example, the particle may be a substitute (or biological substitute) for the MSC or MSC-CM.

Where the term "particle" is used in this document, it should be understood as including (and where the context permits) synonymous with, an exosome.

The exosomes may be used for any of the therapeutic purposes that the MSC or MSC-CM may be put to use.

The exosome preferably has at least one property of a mesenchymal stem cell, such as a therapeutic property. The exosome may have a biological property, such as a biological activity. The exosome may have any of the biological activities of an MSC. The exosome may for example have a therapeutic or restorative activity of an MSC.

Media conditioned by MSCs (such as mesenchymal stem cell conditioned media or MSC-CM, as described below) are known to comprise biological activities of MSC and are capable of substituting for the MSCs themselves—see for example WO 2009/105044. The biological property or biological activity of an MSC may therefore correspond to a biological property or activity of an mesenchymal stem cell conditioned medium. Accordingly, the exosome may comprise one or more biological properties or activities of a mesenchymal stem cell conditioned medium (MSC-CM).

Therapeutic exosomes described here may be isolated from Mesenchymal Stem Cell Conditioned Medium (MSC-CM) and tested for the presence of one or more of the following activities: (a) complement inhibition activity; (b) proteasome activity; (c) glycolytic enzyme activity; (d) anti-oxidative activity; (e) extracellular matrix (ECM) modifying activity; (f) NT5E (CD73) ecto-5'-ectonucleotidase activity; (g) ion homeostasis activity; (h) chaperone activity; and (i) immunodulatory activity.

Detection of Activities

Each of the above activities may be detected in therapeutic exosomes by a number of ways, known in the art. For example, the relevant activity may be detected by detection of the presence of the protein or polypeptide responsible for the activity in the therapeutic exosome. This may be achieved for example by use of cognate antibodies and detection of binding between the antibody and the protein, by immunoassays and Western blots, etc as known in the art.

In general, 1 unit (U) of enzyme activity is defined as the activity required for the production of 1 μmole of product per minute.

Western Blot Protocol for Detection of Activities

An example protocol using Western blot hybridization to detect activity via proteins or polypeptides is set out below.

12 μg exosomes were separated on 4-12% SDS-polyacrylamide gels and electroblotted onto a nitrocellulose membrane. The membrane was transferred to the membrane holder of SNAP i.d. system (Millipore, Billerica, Mass.), blocked and incubated with primary anti-human antibodies, which included mouse anti-GAPDH (1:100 dilution), mouse anti-PGK (1:60), mouse anti-PGD (1:60), rabbit anti-PFKFB3 (1:60), mouse anti-pyruvate kinase (PK, 1:200), mouse anti-20S proteasome α1-7 (1:200), mouse anti-CD73

(1:60) and mouse anti-CD59 (1:200). The blot was then incubated with a horseradish peroxidase-coupled secondary antibody. The secondary antibody used was goat anti-mouse IgG (1:1250) or donkey anti-rabbit IgG (1:1250). All antibodies were obtained from Santa Cruz Biotechnology, Santa Cruz, Calif. except mouse anti-PK which was from Abcam Inc., Cambridge, Mass. The blot was then incubated with HRP-enhanced Chemiluminescent substrate (Thermo Fisher Scientific Inc., Waltham, Mass.) and then exposed to X-ray film.

Liquid Chromatography-Mass Spectrometry (LC MS) or Mass Spectrometry (MS)

Other methods such as mass spectrometry may also be used to detect presence of the protein or polypeptide in the exosome. LC MS is described in detail in the document "Basics of LC/MS Primer" (Agilent Technologies) on the World Wide Web at www.chem.agilent.com/Library/Support/Documents/a05296.pdf.

An example protocol using liquid chromatography-mass spectrometry (LC MS) or mass spectrometry (MS) is set out below.

Proteins in two ml of dialyzed exosomes were reduced, alkylated and tryptic digested as described (20). The samples were then desalted by passing the digested mixture through a conditioned Sep-Pak C-18 SPE cartridge (Waters, Milford, Mass., USA), washed twice with a 3% acetonitrile (ACN) (J T Baker, Phillipsburg, N.J.) and 0.1% formic acid (FA) buffer, and eluted with a 70% ACN and 0.1% FA buffer. The eluted samples were then dried to about 10% of their initial volumes by removing organic solvent in a vacuum centrifuge. To reduce sample complexity, offline peptide fractionation was carried out with a HPLC system (Shimadzu, Japan) through a Polysulfoethyl SCX column (200 mm×4.6 mm) (PolyLC, USA). Mobile phase A (5 mM KH4PO4+ 30% acetonitrile) and mobile phase B (5 mM KH4PO4+ 30% acetonitrile+350 mM KCl) at 1 ml/min. Eight fractions were collected and dried with a vacuum centrifuge. Fractionated samples were loaded into the auto sampler of a Shimadzu micro HPLC system coupled online to a LTQ-FT Ultra linear ion trap mass spectrometer (Thermo Electron, Bremem, Germany) fitted with a nanospray source. Injected peptides were trapped and desalted in a Zorvax 300SB-C18 enrichment column (5 mm×03 mm, Agilent Technologies, Germany) and eluted into a nano-bored C18 packed column (75 μm×100 Å, Michrom Bioresources, Auburn, Calif.). A 90 l/min with a splitter to anmminute gradient at a constant flow rate of 20 effective flow rate of 200 ill/min was used to elute the peptides into the mass spectrometer. The LTQ was operated in a data-dependent mode by performing MS/MS scans for the 8 of the most intense peaks from each MS scan in the FTMS. For each experiment, MS/MS (dta) spectra of the eight SCX fractions were combined into a single mascot generic file by a home-written program. Protein identification was achieved by searching the combined data against the IPI human protein database (version 3.34; 69,164 sequences, 29,064,825 residues) via an in-house Mascot server (Version 2.2.04, Matrix Science, UK). The search parameters were: a maximum of 2 missed cleavages using trypsin; fixed modification was carbaminomethylation of cysteine and variable modification was oxidation of methionine. The mass tolerances were set to 10 ppm and 0.8 Da for peptide precursor and fragment ions respectively. Protein identification was accepted as true positive if two different peptides were found to have scores greater than the homology scores.

Complement Inhibition Activity

Complement inhibition activity may be detected in therapeutic exosomes by detection of any one or more of the proteins or their activities, as set out in Table D1, thereby identifying them as therapeutic exosomes.

TABLE D1

Table D1. Complement Inhibition Activity

| Protein | GenBank Accession Number/ NCBI Reference Sequence (RefSeq) | Synonyms |
| --- | --- | --- |
| CD59 | NM_203329.2, NP_976074.1 | |

Alternatively, or in addition, complement-mediated cell lysis activity may be detected by conducting the assay set out below.

Complement-Mediated Cell Lysis Assay

Briefly, sheep red blood cells (SRBCs) were purchased (Innovative Research, Southfield, Mich.) and washed three times with phosphate buffered saline (PBS) before resuspending at $1\times10^8$ cell/ml PBS. Purified complement components, C5b6, C8 and C9 were purchased from Calbiochem (San Diego, Calif.), and C7 from Sigma-Aldrich (St Louis, Mo.). Assembly of intact C5b-9 on SRBCs was initiated by a 15 min incubation (37° C.) with 1 ml each of C5b6 (0.1 μg/ml) and C7 (0.4 μg/ml) in the presence or absence of exosomes at a final concentration of 0.1 μg/ml. The SRBCs were then washed and incubated with 1 ml each of C8 (0.4 μg/ml), plus C9 (0.4 μg/ml) with or without a blocking CD59 antibody at a final concentration of 0.05 μg/ml for an additional 30 min. After that the SRBCs were centrifuged and the amount of hemoglobin released by the lysed SRBCs in the supernatant was measured by absorbance at 415 nm. Total (100%) hemolysis was obtained by treating the cells with 1% (w/v) Triton X-100.

Proteasome Activity

Proteasome activity may be detected in therapeutic exosomes by detection of any one or more of the proteins or their activities, as set out in Table D2, thereby identifying them as therapeutic exosomes.

TABLE D2

Table D2. Proteasome Activity

| Protein | GenBank Accession Number/ Ref seq | Synonyms |
| --- | --- | --- |
| PSMA1 | X61969.1, CAA43961.1 | |
| PSMA2 | D00760.1, BAA00657.1 | |
| PSMA3 | NM_002788.2, NP_002779.1 | |
| PSMA4 | BC005361.1, AAH05361.1 | |
| PSMA5 | X61970.1, CAA43962.1 | |
| PSMA6 | X59417.1, CAA42052.1 | |
| PSMA7 | AF022815.1, AAB81515.1 | |
| PSMB1 | D00761.1, BAA00658.1 | |
| PSMB2 | D26599.1, BAA05646.1 | |
| PSMB3 | BC013008.2, AAH13008.1 | |
| PSMB4 | D26600.1, BAA05647.1 | |
| PSMB5 | D29011.1, BAA06097.1 | |
| PSMB6 | BC000835.2, AAH00835.1 | |
| PSMB7 | AJ420455.1 | |
| 20S core particle | | |
| PSMB8 | NM_004159.4, NP_004150.1 | |
| PSMB9 | NM_148954.2, NP_683756.1 | |
| PSMB10 | Y13640.1, CAA73982.1 | |

Alternatively, or in addition, proteasome activity may be detected by conducting the assay set out below.

20S Proteasome Assay

The proteasome activity was measured using a 20S proteasome activity assay kit (Millipore) based on detection of the fluorophore 7-Amino-4 methylcoumarin (AMC) after cleavage from the labeled substrate LLVY-AMC (SEQ ID NO: 15) by 20S proteasome in the presence or absence of lactacystin, a specific 20S proteasome inhibitor. Briefly, 4 µg of exosome was incubated with a reaction buffer containing LLVY-AMC (SEQ ID NO: 15) in the presence or absence of 25 µM lactacystin. The samples and AMC standards were incubated at 37° C. and fluorescence intensity at Ex/Em=380/460 nm was monitored for 2 hours.

Unit Activity Definition 1 unit enzyme activity of 20S core particle is defined as the activity required for the production of 1 µmole of product per minute.

Exosomes are found to contain 5.0 µU 20S core particle activity/µg protein.

Glycolytic Enzyme Activity

Glycolytic enzyme activity may be detected in exosomes by detection of any one or more of the proteins or their activities, as set out in Table D3, thereby identifying them as therapeutic exosomes.

TABLE D3

Table D3. Glycolytic Enzyme Activity

| Protein | GenBank Accession Number/ NCBI Reference Sequence (RefSeq) | Synonyms |
|---|---|---|
| GAPDH | AF261085.1, AAF99678.1 | |
| PGK | L00159.1, AAA60078.1 | |
| PGM1 | BC019920.1, AAH19920.1 | |
| Enolase2 | BC022545.1, AAH22545.1 | |
| PKm2 | M23725.1, AAA36449.1 | |
| PFKFB3 | CAH73611 | |
| PFKFB3-phosphorylated form | | |
| ATP* | | |
| NADH* | | |

*It is understood that ATP and NADH are not proteins. They may however be detected in order to detect glycolytic enzyme activity in exosomes and accordingly may be used to establish whether an exosome is a therapeutic exosome. Similarly, detection of ATP and NADH roduction (or both) in a cell may be used (see above).

Accordingly, it will be understood in the context of this document, that the term "protein" or "polypeptide" may encompass small molecules such as ATP and NADH. No adverse significance should be attached to such a reference to detection of an entity under a table header "protein" in such a table (or elsewhere in this document), where the entity is not a protein but is in fact some other type of entity, e.g., a small molecule. Accordingly, some table headings and other references in this document (e.g., Table D3) may for the sake of convenience refer to "proteins" but may include references to ATP, NADH, etc (where these are not in fact proteins). These may be detected, as noted above, for determination of therapeutic exosomes.

Furthermore, as glycolytic enzyme activity may be transferred into cells exposed to the exosomes, resulting in increased ATP and NADH production, detection of ATP or NADH production (or both) by the cell may be used as a means of detecting glycolytic enzyme activity in a produced exosome, thereby identifying it as a therapeutic exosome.

Pyruvate Kinase Assay

5 µg of exosome (in 12 µl) was lysed using a cell extraction kit (Biovision, Mountain view, Calif.). The lysed exosome extract was incubated with 50 µl of reaction mix from a commercially available PK assay kit (Biovision). In this assay, pyruvate produced by PK was oxidized by pyruvate oxidase to produce fluorescences (Ex/Em=535/587 nm). The increase in fluorescence intensity is therefore proportional to the amount of pyruvate produced.

GAPDH and PGK Assay

GAPDH and PGK activity were measured based on their downstream product, ATP in the glycolysis reaction using 2 commercially available kits, KDalert GAPDH assay kit (Ambion Inc., Austin, Tex.) and ApoSENSOR ADP/ATP ratio assay kit (Biovision). Briefly, exosomes were lysed using a cell extraction kit (Biovision). To measure GAPDH activity, 10 µg of lysed exosomes was added to KDalert reaction buffer containing D-glyceraldehyde-3-phosphate, NAD+ and Pi to form 1,3-bisphosphoglycerate+NADH+H+. 250 U/ml of PGK and 60 µM ADP were then added to convert 1,3-bisphosphoglycerate and ADP to 3-phosphoglycerate and ATP. The amount of ATP produced which was proportional to GAPDH activity, was then measured using ATP luciferase assay. To measure PGK activity, 10 µg of lysed exosomes was added to the 1,3-bisphosphoglycerate produced from the above assay. ADP was added to allow the formation of ATP. ATP amount which is proportional to PGK activity was then quantified using ATP luciferase assay.

Glycolysis Cell Based Assay

H9C2 cardiomyocytes were plated onto a 96 well plate (poly-lysine coated) at 30,000 cells per well. After 5 hours, the cells were washed twice with Tyrode's buffer before incubating in Tyrode's buffer containing 20 µmol oligomycin (Sigma-Aldrich), 6 mmol glucose, and with or without 0.1 µg/ml exosomes for 15, 30 and 60 minutes. Cellular ATP concentration was measured using ATPlite 1 step luminescence ATP detection assay system (PerkinElmer, Zaventem, Belgium).

Unit Activity Definition 1 unit enzyme activity of GAPDH (AF261085.1) is defined as the activity required for the production of 1 µmole of product per minute.

Exosomes are found to contain 1.1 µU GAPDH activity/µg protein, 3.59 µU PGK (L00159.1) activity/µg protein and 5.5 µU PKm2 (M23725.1) activity/µg protein.

Anti-Oxidative Activity

Anti-oxidative activity may be detected in therapeutic exosomes by detection of any one or more of the proteins or their activities, as set out in Table D4, thereby identifying them as therapeutic exosomes.

TABLE D4

Table D4. Anti-Oxidative Activity

| Protein | GenBank Accession Number/ NCBI Reference Sequence (RefSeq) | Synonyms |
|---|---|---|
| GAPDH | AF261085.1, AAF99678.1 | |
| PGD (6-phosphogluconate dehydrogenase) | BC000368.2, AAH00368.1 | |
| PXDN | AF200348.1, AAF06354.1 | |
| PRDX1 | BC021683.1, AAH21683.1 | |
| PRDX6 | D14662.1, BAA03496.1 | |
| Catalase | AY028632.1, AAK29181.1 | |

Extracellular Matrix (ECM) Modifying Activity

Extracellular matrix (ECM) modifying activity may be detected in therapeutic exosomes by detection of any one or more of the proteins or their activities, as set out in Table D5, thereby identifying them as therapeutic exosomes.

TABLE D5

Table D5. Extracellular Matrix (ECM) Modifying Activity

| Protein | GenBank Accession Number/ NCBI Reference Sequence (RefSeq) | Synonyms |
|---|---|---|
| MMP1 | X54925.1, CAA38691.1 | |
| MMP2 | NM_001127891.1, NP_001121363.1 | |
| MMP3 | X05232.1, X05232.1 | |
| MMP10 | X07820.1, CAA30679.1 | |
| TIMP1 | NM_003254.2, NP_003245.1 | |
| TIMP2 | NM_003255.4, NP_003246.1 | |
| TIMP3 | NM_000362.4, NP_000353.1 | |

NT5E (CD73) Ecto-5'-Ectonucleotidase Activity

NT5E (CD73) ecto-5'-ectonucleotidase activity may be detected in therapeutic exosomes by detection of any one or more of the proteins or their activities, as set out in Table D6, thereby identifying them as therapeutic exosomes.

Furthermore, as exposing cells to exosomes having NT5E (CD73) ecto-5'-ectonucleotidase activity in the presence of AMP will induce phosphorylation of AKT and ERK1/2, detection of phosphorylated AKT (i.e., phosphorylated AKT1, phosphorylated AKT2 or phosphorylated AKT3) or phosphorylated ERK1 or phosphorylated ERK2 (or any combination of these) in or of the exosome, may be used as a means of detecting NT5E (CD73) ecto-5'-ectonucleotidase enzyme activity in the exosome, thereby identifying it as a therapeutic exosome.

TABLE D6

Table D6. NT5E (CD73) ecto-5'-ectonucleotidase Activity

| Protein | GenBank Accession Number/ NCBI Reference Sequence (RefSeq) | Synonyms |
|---|---|---|
| Ecto-5'-ectonucleotidas | X55740.1, CAA39271.1 | NT5E, CD73 |
| Ecto-apyrase | S73813.1, AAB32152.1 | CD39 |
| AKT1, phosphorylated form | NM_001014432, NP_001014431 | |
| AKT2, phosphorylated form | NM_001626, NP_001617 | |
| AKT3, phosphorylated form | NM_005465, NP_005456 | |
| ERK1, phosphorylated form | NM_001040056, NP_001035145 | MAPK3 |
| ERK2, phosphorylated form | NM_002745, NP_002736 | MAPK1 |

CD73 Assay

CD73 (NT5E) enzymatic activity in exosome was determined by incubating 2.5 µg of exosome in 100 µl Tris buffer pH 7.4 containing 50 µM AMP (Sigma-Aldrich, St Louis, Mo.). The amount of phosphate ions released from the hydrolysis of AMP was then determined by Colorlock Gold kit (Innova Biosciences, Cambridge, UK) as per manufacturer's instruction.

Unit Activity Definition 1 unit Ecto-5'-ectonucleotidase enzyme activity is defined as the activity required for the production of 1 mole of product per minute.

Exosomes are found to contain 22.04 µU Ecto-5'-ectonucleotidase activity/µg protein.

Ion Homeostasis Activity

Ion homeostasis activity may be detected in therapeutic exosomes by detection of any one or more of the proteins or their activities, as set out in Table D7, thereby identifying them as therapeutic exosomes.

TABLE D7

Table D7. Ion Homeostasis Activity

| Protein | GenBank Accession Number/ NCBI Reference Sequence (RefSeq) | Synonyms |
|---|---|---|
| PMCA1 | P20020 | |
| PMCA4 | P23634 | |
| Ca2+-dependent ATPase activity ATP2B1 | J04027.1, AAA74511.1 | |
| Ca2+-dependent ATPase activity ATP2B4 | M25874.1, AAA50819.1 | |

Chaperone Activity

Chaperone activity may be detected in therapeutic exosomes by detection of any one or more of the proteins or their activities, as set out in Table D8, thereby identifying them as therapeutic exosomes.

TABLE D8

Table D8. Chaperone Activity

| Protein | GenBank Accession Number/ NCBI Reference Sequence (RefSeq) | Synonyms |
|---|---|---|
| HSP60 | M34664.1, AAA36022.1 | |
| HSP70 | AB023420.1, BAA75062.1 | |
| HSP90 | M27024.1, AAA63194.1 | |

Immunomodulatory Activity

A therapeutic exosome may display immunomodulatory activity.

Regulation of Adaptive Immunity by Innate Immune Cells (Reviewed 1-3)

The immune system exists primarily to protect the organism against disease by destroying non-self cells or tissues, neutralizing infectious or toxic materials and removing cell debris e.g. dead or dying cells. In vertebrates, the immune system consists of the innate and adaptive immune systems. Innate immune cells include dendritic cells, macrophages and neutrophils and these cells are genetically programmed to recognize invariant features of infectious/toxic materials, stress signals, dead/dying cells, or non-self cells. It is evolutionarily conserved and provides the first line of defense. Adaptive immune cells are the T and B lymphocytes. They adapt to each foreign, toxic or non-self agent by generating receptors specific against these materials de novo to target them for neutralization or destruction. On the other hand, innate immune cells recognize conserved molecular signatures within microbial pathogens referred to commonly as pathogen-associated molecular patterns and stress signals through germline-encoded pattern recognition receptors (PPRs) such as include Toll-like receptors (TLRs), retinoic acid-inducible gene 1-like RNA helicases, nucleotide binding oligomerisation domain-like receptors, and C-type lectin receptors. The activation of adaptive immune cells to generate specific receptors against infectious or toxic agents is complex and modulated by the innate immune cells. Among the PPRs, the TLRs are the best characterized PPRs with regards to modulation of adaptive immune responses such as production of IgM, IgG and IgA antibody, and activation of $T_H1$, $T_H17$ CD4⁺, and CD8⁺ T cells.

TLRs are highly conserved type 1 integral membrane glycoproteins. In human, ten TLRs have been identified to date. All TLRs, except TLR3, signal through the MyD88-dependent pathway either directly or in combination with TIRAP, ultimately leading to activation and nuclear translocation of NFκB, activating protein 1 (AP 1), or both of these, leading to the production of inflammatory cytokines. TLR3 and TLR4 initiate the MyD88-independent, TRIF-dependent signalling pathway leading to the activation and nuclear translocation of either NFκB or IRF3 to produce inflammatory cytokines and type 1 interferon, respectively. Different TLRs recognise different classes of pathogen-associated molecular patterns, e.g. TLR4 recognises bacterial cell-surface lipopolysaccharides, TLR1 and TLR2 recognise peptidoglycans, TLR2 and TLR6 recognise lipoproteins, TLR3 recognises viral double-stranded RNA, TLR7 and TLR8 recognise viral single-stranded RNA, TLR9 recognises bacterial and viral CpG, TLR5 recognises flagellin.

Endogenous Ligands of TLRs (Reviewed 4)

Despite the overwhelming importance of TLRs in mediating host immunity against infectious agents and their products, activation of TLR signaling by endogenous ligands to trigger a sterile inflammatory response is increasingly viewed as an important function of TLRs. To date, numerous endogenous ligands for the different TLRs have been identified (Table D9 below). TLRs have been implicated in ischemia and reperfusion injury, tissue repair and regeneration, autoimmune diseases, and tumorigenesis and tumour progression.

TABLE D9

TLRs and their endogenous ligands. Highlighted ligands are also found to be present in MSC exosomes.

| | |
|---|---|
| TLR2 | Biglycan, endoplasmin, HMGB1, HSP60, HSP70, human cardiac myosin, hyaluronan and monosodium urate crystals |
| TLR3 | mRNA |
| TLR4 | Biglycan, CD138, α-crystallin A chain, β-defensin2, endoplasmin, fibrinogen, fibronectin, heparan sulphate, HMGB1, HSP22, HSP60, HSP70, HSP72, hyaluronan, monosodium urate crystals, OxPAPC, resistin, S100 proteins, surfactant protein A and tenascin-C |
| TLR7 | RNA and small interfering RNA (siRNA) |
| TLR8 | Human cardiac myosin and small interfering RNA (siRNA) |
| TLR9 | DNA and HMGB1 |

Immune Modulatory Activities of MSCs

MSCs display immunomodulatory properties in vitro such as inhibition of T-cell proliferation induced by alloantigens, mitogens and CD3-ligation, inhibit the proliferation of B cells, and the activity of natural killer cells[5]. Clinical trials testing the therapeutic efficacy of MSC-based intervention for human GVHD[6] and Crohn's disease[7] have been encouraging. However the underlying mechanism for the immunomodulatory properties of MSCs remains poorly understood. Increasingly, it is thought that these properties are mediated by paracrine secretion from MSCs[8].

In 2008, our group demonstrated that culture medium conditioned by human embryonic stem cell-derived MSCs (hESC-MSCs) reduced relative infarct size in a pig and mouse model of ischemia/reperfusion injury[9] and improved cardiac function in pig model of chronic ischemia[10], and the active component has a presumptive diameter of 50-200 nm. This component was subsequently purified by HPLC and identified as an exosome[11]. Proteomic analysis revealed that these exosomes contained endogenous ligands for TLR2 and TLR4 (table 1). Therefore, MSC exosomes have the potential to activate TLR2 and TLR4 and contribute to the immunomodulatory activities of MSCs.

Immunomodulatory activity may be detected in therapeutic exosomes by detection of any one or more of the proteins or their activities, as set out in Table D10, thereby identifying them as therapeutic exosomes.

TABLE D10

| Variant | | GenBank Accession Number | NCBI Reference Sequence (RefSeq) |
|---|---|---|---|
| Biglycan | | AK092954 | NM_001711 |
| Endoplasmin | | AY040226 | NM_003299 |
| HSP60 | | M34664.1, AAA36022.1 | |
| HSP70 | | AB023420.1, BAA75062.1 | |
| β-defensin 2 | | AJ000152 | NM_004942 |
| Fibrinogen | alpha | | NM_021871 |
| | beta | | NM_001184741 |
| | gamma | | NM_000509 |
| Fibronectin | | | NM_212482 |
| Tenascin-C | | | NM_002160 |
| S100 proteins | S100A11 | D38583 | NM_005620 |
| | S100A13 | AK097132 | NM_001024212 |
| | S100A8 | BC005928 | NM_002964 |
| | S100A9 | BC047681 | NM_002965 |
| | S100P | X65614 | NM_005980 |

Mesenchymal Stem Cell Conditioned Medium (MSC-CM)

The conditioned cell culture medium such as a Mesenchymal Stem Cell Conditioned Medium (MSC-CM) may be obtained by culturing a mesenchymal stem cell (MSC), a descendent thereof or a cell line derived therefrom in a cell culture medium; and isolating the cell culture medium. The mesenchymal stem cell may be produced by a process comprising obtaining a cell by dispersing a embryonic stem (ES) cell colony. The cell, or a descendent thereof, may be propagated in the absence of co-culture in a serum free medium comprising FGF2.

The exosome may be produced or isolated in a number of ways. Such a method may comprise isolating the exosome from a mesenchymal stem cell (MSC). Such a method may comprise isolating the exosome from an mesenchymal stem cell conditioned medium (MSC-CM). The exosome may be isolated for example by being separated from non-associated components based on any property of the exosome. For example, the exosome may be isolated based on molecular weight, size, shape, composition or biological activity. For example, filtration with a membrane of a suitable molecular weight or size cutoff, as described in the Assays for Molecular Weight elsewhere in this document, may be used. One or more biological activities of the exosome may be used to track its activity during fractionation of the mesenchymal stem cell conditioned medium (MSC-CM).

Immunomodulatory Activity Assay

Immunomodulatory activity of exosomes may be assessed by using THP-1 cells and genetically modified THP-cell line/HEK reporter cell lines. Such cell lines are described in the Examples below.

Immunomodulatory activity of exosomes may be assessed using unmodified THP-1, by assaying the ability of the exosome to induce cytokine production. This is described in detail at Example 23 below. Alternatively cytokine production may be assessed using surrogate reporter cell lines as described in the Examples. For example, a THP1-XBlue with a stably transfected secreted embryonic alkaline phosphatase (SEAP) reporter gene under the transcriptional control of NF-kB promoter or a THP1-XBlue-defMYD that is deficient in MyD88 activity may be used, as described in Example 19.

Immunomodulatory activity of exosomes may also be assayed by their ability to inhibit proliferation of Concanavalin A-activated lymphocytes. This is described in detail in Example 28.

Other methods of assaying immunomodulatory activity of exosomes may be used. These include exposing CD4+ T cells to exosome-treated monocytes e.g. THP-1 to determine if they enhance Tregs or Th17 production. This is described in detail in Example 26.

Exosome Properties

The property of a mesenchymal stem cell may comprise a property of a medium conditioned by a mesenchymal stem cell (MSC-CM). Methods of producing such a mesenchymal stem cell conditioned medium are described known in the art and are described for example in Example 1 of WO 2009/105044.

The property may comprise a biological property such as a biological activity. Examples of biological activities include cardioprotection, reduction of oxidative stress and reduction of infarct size.

Cardioprotection

The exosome, in particular a therapeutic exosome, may have a property of mesenchymal stem cells and/or mesenchymal stem cell conditioned medium (MSC-CM) comprising cardioprotection The cardioprotection may comprise restoration or maintenance of cardiac function during ischemia and/or reperfusion.

Assay for Cardioprotection

Cardioprotection may for example be assayed using any one or more of the methods described in Examples 5, 10, 14 and 20 of WO 2009/105044.

Oxidative Stress

The exosome, in particular a therapeutic exosome, may have a property of mesenchymal stem cells and/or mesenchymal stem cell conditioned medium (MSC-CM) comprising the ability to reduce oxidative stress (or cytoprotection).

Assay for Oxidative Stress

The reduction of oxidative stress may for example be assayed using an in vitro assay of hydrogen peroxide ($H_2O_2$)-induced cell death. In summary, hydrogen peroxide ($H_2O_2$)— mediated oxidative stress is induced in human leukemic CEM cells and cell viability is monitored by Trypan blue-exclusion. Human leukemic CEM cells are incubated with exosome, conditioned medium or mesenchymal stem cell (with saline as a control) and treated with 50 µM $H_2O_2$ to induce oxidative stress. Cell viability is assessed using Trypan Blue exclusion at 12, 24, 36 and 48 hours after $H_2O_2$ treatment.

The reduction of oxidative stress may further be assayed using an in vivo assay of DNA oxidation. In vivo oxidative stress may also be assayed as follows. Pigs are treated with the exosome, conditioned medium or mesenchymal stem cell (with saline as a control). Tissue sections of pig heart are obtained. Nuclear oxidative stress in tissue sections of treated and untreated pigs is quantified by 8-OHdG immunostaining for oxidized DNA. The tissue sections are assayed for intense nuclear staining indicative of DNA oxidation and oxidative stress.

Infarct Size

The exosome, in particular a therapeutic exosome, may have a property of mesenchymal stem cells and/or mesenchymal stem cell conditioned medium (MSC-CM) comprising the ability to reduce infarct size.

Assay for Infarct Size

Infarct size may for example be assayed using any one or more of the methods described in Examples 6 and 13 of WO 2009/105044.

Exosome Size

The exosome may have a molecular weight of greater than 100 kDa. It may have a molecular weight of greater than 500 kDa. For example, it may have a molecular weight of greater than 1000 kDa.

The molecular weight may be determined by various means. In principle, the molecular weight may be determined by size fractionation and filtration through a membrane with the relevant molecular weight cut-off. The exosome size may then be determined by tracking segregation of component proteins with SDS-PAGE or by a biological assay.

Assay of Exosome Size by HPLC Dynamic Light Scattering

The instrument setup consisted of a liquid chromatography system with a binary pump, an auto injector, a thermostated column oven and a UV-visible detector operated by the Class VP software from Shimadzu Corporation (Kyoto, Japan). The Chromatography columns used were TSK Guard column SWXL, 6×40 mm and TSK gel G4000 SWXL, 7.8×300 mm from Tosoh Corporation (Tokyo, Japan). The following detectors, Dawn 8 (light scattering), Optilab (refractive index) and QELS (dynamic light scattering) were connected in series following the UV-visible detector. The last three detectors were from Wyatt Technology Corporation (California, USA) and were operated by the ASTRA software. The components of the sample were separated by size exclusion i.e. the larger molecules will elute before the smaller molecules. The eluent buffer used was 20 mM phosphate buffer with 150 mM of NaCl at pH 7.2. This buffer was filtered through a pore size of 0.1 µm and degassed for 15 minutes before use. The chromatography system was equilibrated at a flow rate of 0.5 ml/min until the signal in Dawn 8 stabilized at around 0.3 detector voltage units. The UV-visible detector was set at 220 ηm and the column was oven equilibrated to 25° C. The elution mode was isocratic and the run time was 40 minutes. The volume of sample injected ranged from 50 to 100 ml. The % area of the exosome peak vs. all other peaks was integrated from the UV-visible detector. The hydrodynamic radius, Rh was computed by the QELS and Dawn 8 detectors. The highest count rate (Hz) at the peak apex was taken as the Rh. Peaks of the separated components visualized at 220 ηm were collected as fractions for further characterization studies.

Assay of Molecular Weight by SDS-PAGE

The exosome may have a molecular weight of greater than 100 kDa. For example, the exosome may be such that most proteins of the exosome with less than 100 kDa molecular weight segregate into the greater than 100 kDa molecular weight retentate fraction, when subject to filtration. Similarly, when subjected to filtration with a membrane with a 500 kDa cut off, most proteins of the exosome with less than 500 kDa molecular weight may segregate into the greater than 500 kDa molecular weight retentate fraction. This indicates that the exosome may have a molecular weight of more than 500 kDa.

Assay of Molecular Weight by Biological Activity

The exosome may have a molecular weight of more than 1000 kDa. For example, the exosome may be such that when subject to filtration with a membrane with a molecular weight cutoff of 1000 kDa, the relevant biological activity substantially or predominantly remains in the retentate fraction. Alternatively or in addition, biological activity may be absent in the filtrate fraction. The biological activity may comprise any of the biological activities of the exosome described elsewhere in this document.

Assay of Molecular Weight by Infarct Size

For example, the biological activity may comprise reduction of infarct size, as assayed in any suitable model of myocardia ischemia and reperfusion injury. For example, the biological activity may be assayed in a mouse or pig model, such as described in the Examples of WO 2009/105044.

In summary, myocardial ischemia is induced by 30 minutes left coronary artery (LCA) occlusion by suture ligation and reperfusion is initiated by removal of suture. Mice are treated with liquid containing the exosome (such as unfractionated MSC-CM), filtrate (such as <100 or 1,000 kD fraction), retentate (such as >1000 kD retentate) or saline intravenously via the tail vein, 5 minutes before reperfusion. 24 hours later, the hearts are excised. Before excision, the Area At Risk (AAR) is determined by religating the LCA and then perfusing Evans blue through the aorta.

AAR is defined as the area not stained by the dye and is expressed as a percentage of the left ventricular wall area. Infarct size is assessed 24 hours later using Evans blue and TTC. Where the relative infarct size is significantly reduced in animals treated with mesenchymal stem cell conditioned medium (MSC-CM) and the retentate (such as a >1000 kD) fraction when compared to saline, this indicates that the exosome has a molecular weight which is higher than the relevant cutoff of the membrane (e.g., greater than 1000 kDa).

Exosome Molecular Weight

The exosome may have a size of greater than 2 ηm. The exosome may have a size of greater than 5 ηm, 10 ηm, 20 ηm, 30 ηm, 40 ηm or 50 ηm. The exosome may have a size of greater than 100 ηm, such as greater than 150 ηm. The exosome may have a size of substantially 200 ηm or greater.

The exosome or exosomes may have a range of sizes, such as between 2ηm to 20 μm, 2 ηm to 50 ηm, 2 ηm to 100 ηm, 2 ηm to 150 ηm or 2 ηm to 200 ηm. The exosome or exosomes may have a size between 20 ηm to 50 ηm, 20 ηm to 100 ηnm, 20 ηm to 150 ηm or 20 ηm to 200 ηm. The exosome or exosomes may have a size between 50 ηm to 100 ηm, 50 ηm to 150 ηm or 50 ηm to 200 ηm. The exosome or exosomes may have a size between 100 ηm to 150 ηm or 100 ηm to 200 ηm. The exosome or exosomes may have a size between 150 ηm to 200 ηm.

The size may be determined by various means. In principle, the size may be determined by size fractionation and filtration through a membrane with the relevant size cutoff. The exosome size may then be determined by tracking segregation of component proteins with SDS-PAGE or by a biological assay.

The size may also be determined by electron microscopy, as described in Example 21 of WO 2009/105044.

Composition

The exosome may comprise one or more proteins secreted by a mesenchymal stem cell. The exosome may comprise one or more proteins present in mesenchymal stem cell conditioned medium (MSC-CM).

For example, the exosome may comprise 10% or more, 20% or more, 30% or more, 40% or more, 50% or more, 60% or more or 70% or more of these proteins. The exosome may comprise substantially about 75% of these proteins. The proteins may be defined by reference to a list of proteins or gene products of a list of genes.

Proteins and gene products which may be comprised in an exosome are described in for example WO 2009/105044.

Exosome

The active component in the secretion such as an exosome that confers cardioprotection against the reperfusion injury may be isolated by means known in the art and described for example in WO 2009/105044. The active component may comprise an exosome secreted by the mesenchymal stem cells (MSCs).

Exosomes are small membrane vesicles formed in late endocytic compartments (multivesicular bodies) first described to be secreted by reticulocytes in 1983 and subsequently found to be secreted by many cells types including various haematopoietic cells, tumours of haematopoietic or non-haematopoietic origin and epithelial cells. They are distinct entities from the more recently described 'ribonuclease complex' also named exosome.

Exosomes may be defined by morphological and biochemical parameters. Accordingly, the exosomes described here may comprise one or more of these morphological or biochemical parameters.

Exosomes are classically defined as "saucer-like" vesicles or a flattened sphere limited by a lipid bilayer with diameters of 40-100 nm and are formed by inward budding of the endosomal membrane. Like all lipid vesicles and unlike protein aggregates or nucleosomal fragments that are released by apoptotic cells, exosomes have a density of ~1.13-1.19 g/ml and float on sucrose gradients. Exosomes are enriched in cholesterol and sphingomyelin, and lipid raft markers such as GM1, GM3, flotillin and the src protein kinase Lyn suggesting that their membranes are enriched in lipid rafts.

The molecular composition of exosomes from different cell types and of different species has been examined. In general, exosomes contain ubiquitous proteins that appear to be common to all exosomes and proteins that are cell-type specific. Also, proteins in exosomes from the same cell-type but of different species are highly conserved. The ubiquitous exosome-associated proteins include cytosolic proteins found in cytoskeleton e.g. tubulin, actin and actin-binding proteins, intracellular membrane fusions and transport e.g. annexins and rab proteins, signal transduction proteins e.g. protein kinases, 14-3-3 and heterotrimeric G proteins, metabolic enzymes e.g. peroxidases, pyruvate and lipid kinases, and enolase-1 and the family of tetraspanins e.g. CD9, CD63, CD81 and CD82. The tetraspannins are highly enriched in exosomes and are known to be involved in the organization of large molecular complexes and membrane subdomains.

Examples of cell-type specific proteins in exosomes are MHC class II molecules in exosomes from MHC class II-expressing cells, CD86 in dendritic cell-derived exosomes, T-cell receptors on T-cell-derived exosomes etc. Notably, exosomes do not contain proteins of nuclear, mitochondrial, endoplasmic-reticulum or Golgi-apparatus origin. Also, highly abundant plasma membrane proteins are absent in exosomes suggesting that they are not simply fragments of the plasma membrane. Many of the reported ubiquitous exosome-associated proteins are also present in the proteomic profile of the hESC-MSC secretion.

Exosomes are also known to contain mRNA and microRNA, which can be delivered to another cell, and can be functional in this new location. The physiological functions of exosome remain poorly defined. It is thought to help eradicate obsolete proteins, recycle proteins, mediate transmission of infectious particles such as prions and viruses, induce complement resistance, facilitate immune cell-cell communication and transmit cell signaling. Exosomes have been used in immunotherapy for treatment of cancer.

Uses of Therapeutic Exosomes from Mesenchymal Stem Cells

The exosomes including therapeutic exosomes may be used as a substitute for an MSC or MSC-CM, as described above and below.

In particular, the therapeutic exosomes may be used for any of the therapeutic purposes that MSCs or MSC-CMs are currently being used, or in the future may be used.

It will be evident that the methods and compositions described here enable the production of therapeutic exosomes from mesenchymal stem cells. Thus, any uses of mesenchymal stem cells will equally attach to therapeutic exosomes from mesenchymal stem cells.

Mesenchymal stem cells and differentiated cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer. Accordingly, therapeutic exosomes from MSCs may be used to treat such diseases.

Therapeutic exosomes from mesenchymal stem cells such as those made according to the methods and compositions described here may be used for a variety of commercially important research, diagnostic, and therapeutic purposes.

The therapeutic exosomes from mesenchymal stem cells may in particular be used for the preparation of a pharmaceutical composition for the treatment of disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Mesenchymal stem cells made by the methods and compositions described here have similar or identical properties to bone marrow derived mesenchymal stem cells (BM-MSCs). Therefore, the mesenchymal stem cells, and any differentiated cells made from these, as well as therapeutic exosomes derived therefrom, may be used in any of the applications for which BM-MSCs are known to be used, or in which it is possible for them to be used.

Diseases Treatable by Exosomes from Mesenchymal Stem Cells

Analysis of the proteome of MSCs shows that the proteins expressed are involved in three biological processes: metabolism, defense response, and tissue differentiation including vascularization, hematopoiesis and skeletal development. Accordingly, the therapeutic exosomes from MSCs described here may be used to treat diseases which these functions may have a role in, or whose repair or treatment involves any one or more of these biological processes. Similarly, the proteins expressed by the MSCs, singly or in combination, preferably in the form of therapeutic exosomes as described here, may be used to supplement the activity of, or in place of, the MSCs, or media conditioned by the MSCs, for the purpose of for example treating or preventing such diseases.

The 201 gene products expressed by the MSCs are shown to activate important signalling pathways in cardiovascular biology, bone development and hematopoiesis such as Jak-STAT, MAPK, Toll-like receptor, TGF-beta signalling and mTOR signaling pathways. Accordingly, the therapeutic exosomes from the MSCs, etc, may be used to prevent or treat a disease in which any of these signalling pathways is involved, or whose aetiology involves one or more defects in any one or more of these signalling pathways.

Accordingly, such therapeutic exosomes may be used to treat cardiac failure, bone marrow disease, skin disease, burns and degenerative diseases such as diabetes, Alzheimer's disease, Parkinson's disease and cancer.

Such therapeutic exosomes may also be used to treat myocardial infarction, a cutaneous wound, a dermatologic disorder, a dermatological lesion, dermatitis, psoriasis, condyloma, verruca, hemangioma, keloid, skin cancer, atopic dermatitis, Behcet disease, chronic granulomatous disease, cutaneous T cell lymphoma, ulceration, a pathological condition characterised by initial injury inducing inflammation and immune dysregulation leading to chronic tissue remodeling including fibrosis and loss of function, renal ischemic injury, cystic fibrosis, sinusitis and rhinitis or an orthopaedic disease.

The therapeutic exosomes may be used to aid wound healing, scar reduction, bone formation, a bone graft or bone marrow transplantation in an individual.

Unless the context dictates otherwise, the term "conditioned medium" should be taken to include not only cell culture medium exposed to MSCs as well as such a composition comprising one or more, preferably substantially all, the polypeptides which are present in the conditioned medium.

The therapeutic exosomes may also be used as sources for any of the proteins secreted or expressed by the MSCs. We therefore provide for a method of producing a polypeptide as comprised in an therapeutic exosome, the method comprising obtaining a therapeutic exosome as described, and isolating the polypeptide from the therapeutic exosome.

Delivery of Therapeutic Exosomes

The therapeutic exosomes as described in this document may be delivered to the human or animal body by any suitable means.

We therefore describe a delivery system for delivering a therapeutic exosome as described in this document to a target cell, tissue, organ, animal body or human body, and methods for using the delivery system to deliver therapeutic exosomes to a target.

The delivery system may comprise a source of therapeutic exosomes, such as a container containing the therapeutic exosomes. The delivery system may comprise a dispenser for dispensing the therapeutic exosomes to a target.

Accordingly, we provide a delivery system for delivering a therapeutic exosome, comprising a source of therapeutic exosomes as described in this document together with a dispenser operable to deliver the therapeutic exosomes to a target.

We further provide for the use of such a delivery system in a method of delivering a therapeutic exosome to a target.

Delivery systems for delivering fluid into the body are known in the art, and include injection, surgical drips, cathethers (including perfusion cathethers) such as those described in U.S. Pat. No. 6,139,524, for example, drug delivery catheters such as those described in U.S. Pat. No. 7,122,019.

Delivery to the lungs or nasal passages, including intranasal delivery, may be achieved using for example a nasal spray, puffer, inhaler, etc as known in the art (for example as shown in U.S. Design patent D544,957.

Delivery to the kidneys may be achieved using an intra-aortic renal delivery catheter, such as that described in U.S. Pat. No. 7,241,273.

It will be evident that the particular delivery should be configurable to deliver the required amount of therapeutic exosomes at the appropriate interval, in order to achieve optimal treatment.

The therapeutic exosomes may for example be used for the treatment or prevention of atherosclerosis. Here, perfusion of therapeutic exosomes may be done intravenously to stabilize atherosclerotic plaques or reduce inflammation in the plaques. The therapeutic exosomes may be used for the treatment or prevention of septic shock by intravenous perfusion.

The therapeutic exosomes may be used for the treatment or prevention of heart failure. This may be achieved by chronic intracoronary or intramyocardially perfusion of therapeutic exosomes to retard remodeling or retard heart failure. The therapeutic exosomes may be used for the treatment or prevention of lung inflammation by intranasal delivery.

The therapeutic exosomes may be used for the treatment or prevention of dermatological conditions e.g. psoriasis. Long term delivery of therapeutic exosomes may be employed using transdermal microinjection needles until the condition is resolved.

It will be evident that the delivery method will depend on the particular organ to which the therapeutic exosomes is to be delivered, and the skilled person will be able to determine which means to employ accordingly.

As an example, in the treatment of cardiac inflammation, the therapeutic exosomes may be delivered for example to the cardiac tissue (i.e., myocardium, pericardium, or endocardium) by direct intracoronary injection through the chest wall or using standard percutaneous catheter based methods under fluoroscopic guidance for direct injection into tissue such as the myocardium or infusion of an inhibitor from a stent or catheter which is inserted into a bodily lumen.

Any variety of coronary catheter, or a perfusion catheter, may be used to administer the compound. Alternatively the therapeutic exosomes may be coated or impregnated on a stent that is placed in a coronary vessel.

Tissue Regeneration

Mesenchymal stem cells and differentiated cells made according to the methods and compositions described here, and therapeutic exosomes derived therefrom, may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Mesenchymal stem cells and differentiated cells and therapeutic exosomes derived therefrom may be used for tissue engineering, such as for the growing of skin grafts. Modulation of stem cell differentiation may be used for the bioengineering of artificial organs or tissues, or for prosthetics, such as stents.

Cancer

Mesenchymal stem cells and differentiated cells made by the methods and compositions described here and therapeutic exosomes derived therefrom may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

The mesenchymal stem cells and differentiated cells made according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino)benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Caminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Obtaining Mesenchymal Stem Cells (MSC)

The exosomes, including therapeutic exosomes, described here may be isolated or produced from mesenchymal stem cell conditioned medium (MSC-CM). MSCs suitable for use in the production of conditioned media and exosomes may be made by any method known in the art.

In particular, MSCs may be made by propagating a cell obtained by dispersing a embryonic stem (ES) cell colony, or a descendent thereof, in the absence of co-culture in a serum free medium comprising FGF2. This is described in detail in the sections below.

The prior art methods of obtaining mesenchymal stem cells (MSC) or MSC-like cells from hESCs involve either transfection of a human telomerase reverse transcriptase (hTERT) gene into differentiating hESCs (Xu et al., 2004) or coculture with mouse OP9 cell line (Barberi et al., 2005). The use of exogenous genetic material and mouse cells in these derivation protocols introduces unacceptable risks of tumorigenicity or infection of xenozootic infectious agents.

The exosomes may therefore be made from MSCs derived by the use of a clinically relevant and reproducible protocol for isolating similar or identical (such as homogenous) MSC populations from differentiating hESCs. In general, the method comprises dispersing a embryonic stem (ES) cell colony into cells. The cells are then plated out and propagated. The cells are propagated in the absence of co-culture in a serum free medium comprising fibroblast growth factor 2 (FGF2), in order to obtain mesenchymal stem cells (MSCs).

Thus, the protocol does not require serum, use of mouse cells or genetic manipulations and requires less manipulations and time, and is therefore highly scalable. The protocol may be used for the isolation of MSCs from two different hESC lines, HuES9 and H-1 and also a third one, Hes-3. Human ES cell derived MSCs (hESC-MSCs) obtained by the methods and compositions described here are remarkably similar to bone-marrow derived MSCs (BM-MSCs).

The embryonic stem cell culture may comprise a human embryonic stem cell (hESC) culture.

In a one embodiment, a method of generating mesenchymal stem cells (MSC) comprises trypsinizing and propagating hESCs without feeder support in media supplemented with FGF2 and optionally PDGF AB before sorting for CD105+CD24− cells.

The method may comprise sorting for CD105+, CD24− cells from trypsinized hESCs one week after feeder-free propagation in a media supplemented with FGF2 and optionally PDGF AB will generate to generate a hESC-MSC cell culture in which at least some, such as substantially all, or all cells are similar or identical (such as homogenous) to each other The MSCs produced by this method may be used to produce mesenchymal stem cell conditioned medium (MSC-CM), from which the exosomes may be isolated.

Disaggregating Embryonic Stem Cell Colonies

One method of producing mesenchymal stem cells may comprise dispersing or disaggregating an embryonic stem cell colony into cells.

The embryonic stem cell colony may comprise a huES9 colony (Cowan C A, Klimanskaya I, McMahon J, Atienza J, Witmyer J, et al. (2004) *Derivation of embryonic stem-cell lines from human blastocysts*. N Engl J Med 350: 1353-1356) or a H1 ESC colony (Thomson J A, Itskovitz-Eldor J, Shapiro S S, Waknitz M A, Swiergiel J J, et al. (1998) *Embryonic Stem Cell Lines Derived from Human Blastocysts*. Science 282: 1145-1147).

The cells in the colony may be disaggregated or dispersed to a substantial extent, i.e., at least into clumps. The colony may be disaggregated or dispersed to the extent that all the cells in the colony are single, i.e., the colony is completely disaggregated.

The disaggregation may be achieved with a dispersing agent.

The dispersing agent may be anything that is capable of detaching at least some embryonic stem cells in a colony from each other. The dispersing agent may comprise a reagent which disrupts the adhesion between cells in a colony, or between cells and a substrate, or both. The dispersing agent may comprise a protease.

The dispersing agent may comprise trypsin. The treatment with trypsin may last for example for 3 minutes or thereabouts at 37 degrees C. The cells may then be neutralised, centrifuged and resuspended in medium before plating out.

The method may comprise dispersing a confluent plate of human embryonic stem cells with trypsin and plating the cells out.

The disaggregation may comprise at least some of the following sequence of steps: aspiration, rinsing, trypsinization, incubation, dislodging, quenching, re-seeding and aliquoting. The following protocol is adapted from the Hedrick Lab, UC San Diego (http://hedricklab.ucsd.edu/Protocol/COSCell.html).

In the aspiration step, the media is aspirated or generally removed from the vessel, such as a flask. In the rinsing step, the cells are rinsed with a volume, for example 5-10 mls, of a buffered medium, which is may be free from $Ca^{2+}$ and $Mg^{2+}$. For example, the cells may be rinsed with calcium and magnesium free PBS. In the trypsinization step, an amount of dispersing agent in buffer is added to the vessel, and the vessel rolled to coat the growing surface with the dispersing agent solution. For example, 1 ml of trypsin in Hank's BSS may be added to a flask.

In the incubation step, the cells are left for some time at a maintained temperature. For example, the cells may be left at 37° C. for a few minutes (e.g., 2 to 5 minutes). In the dislodging step, the cells may be dislodged by mechanical action, for example by scraping or by whacking the side of the vessel with a hand. The cells should come off in sheets and slide down the surface.

In the quenching step, a volume of medium is added to the flask. The medium may comprise a neutralizing agent to stop the action of the dispersing agent. For example, if the dispersing agent is a protease such as trypsin, the medium may contain a protein, such as a serum protein, which will mop up the activity of the protease. In a particular example, 3 ml of serum containing cell culture medium is added to the flask to make up a total of 4 mls. The cells may be pipetted to dislodge or disperse the cells.

In the re-seeding step, the cells are re-seeded into fresh culture vessels and fresh medium added. A number of re-seedings may be made at different split ratios. For example, the cells may be reseeded at 1/15 dilution and 1/5 dilution. In a particular example, the cells may be re-seeded by adding 1 drop of cells into a 25 cm² flask and 3 drops into another to re-seed the culture, and 7-8 mls media is then added to each to provide for 1/15 dilution and 1/5 dilution from for example a 75 cm² flask. In the aliquoting step, the cells may be aliquoted into new dishes or whatever split ratio is desired, and media added.

In a specific embodiment, the method includes the following steps: human ES cells are first grown suspended in non-adherent manner to form embryoid bodies (EBs). 5-10 day old EBs are then trypsinized before plating as adherent cells on gelatine coated tissue culture plates.

Maintenance as Cell Culture

The disaggregated cells may be plated and maintained as a cell culture.

The cells may be plated onto a culture vessel or substrate such as a gelatinized plate. Crucially, the cells are grown and propagated without the presence of co-culture, e.g., in the absence of feeder cells.

The cells in the cell culture may be grown in a serum-free medium which is supplemented by one or more growth factors such as fibroblast growth factor 2 (FGF2) and optionally platelet-derived growth factor AB (PDGF AB), at for example 5 ng/ml. The cells in the cell culture may be split or subcultured 1:4 when confluent, by treatment with trypsin, washing and replating.

Absence of Co-Culture

The cells may be cultured in the absence of co-culture. The term "co-culture" refers to a mixture of two or more different kinds of cells that are grown together, for example, stromal feeder cells.

Thus, in typical ES cell culture, the inner surface of the culture dish is usually coated with a feeder layer of mouse embryonic skin cells that have been treated so they will not divide. The feeder layer provides an adherent surface to enable the ES cells to attach and grow. In addition, the feeder cells release nutrients into the culture medium which are required for ES cell growth. In the methods and compositions described here, the ES and MSC cells may be cultured in the absence of such co-culture.

The cells may be cultured as a monolayer or in the absence of feeder cells. The embryonic stem cells may be cultured in the absence of feeder cells to establish mesenchymal stem cells (MSC).

The dissociated or disaggregated embryonic stem cells may be plated directly onto a culture substrate. The culture substrate may comprise a tissue culture vessel, such as a Petri dish. The vessel may be pre-treated. The cells may be plated onto, and grow on, a gelatinised tissue culture plate.

An example protocol for the gelatin coating of dishes follows. A solution of 0.1% gelatin in distilled water is made and autoclaved. This may be stored at room temp. The bottom of a tissue culture dish is covered with the gelatin solution and incubated for 5-15 min. Remove gelatin and plates are ready to use. Medium should be added before adding cells to prevent hypotonic lysis.

Serum Free Media

The dissociated or disaggregated embryonic stem cells may be cultured in a medium which may comprise a serum-free medium.

The term "serum-free media" may comprise cell culture media which is free of serum proteins, e.g., fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may comprise or be supplemented with 10% serum replacement media from Invitrogen-Gibco (Grand Island, N.Y.).

Growth Factor

The serum-free medium in which the dissociated or disaggregated embryonic stem cells are cultured may comprise one or more growth factors. A number of growth factors are known in the art, including PDGF, EGF, TGF-a, FGF, NGF, Erythropoietin, TGF-b, IGF-I and IGF-II.

The growth factor may comprise fibroblast growth factor 2 (FGF2). The medium may also contain other growth factors such as platelet-derived growth factor AB (PDGF AB). Both of these growth factors are known in the art. The method may comprise culturing cells in a medium comprising both FGF2 and PDGF AB.

Alternatively, or in addition, the medium may comprise or further comprise epidermal growth factor (EGF). Use of EGF may enhance growth of MSCs. EGF may be used at any suitable concentration, for example 5-10 ng/ml EGF. EGF may be used in place of PDGF. EGF is a protein well known in the art, and is referred to as symbol EGF, Alt. Symbols URG, Entrez 1950, HUGO 3229, OMIM 131530, RefSeq NM_001963, UniProt P01133.

Thus, we disclose the use of media comprising (i) FGF2, (ii) FGF2 and PDGF and (iii) FGF2 and EGF and other combinations.

FGF2 is a wide-spectrum mitogenic, angiogenic, and neurotrophic factor that is expressed at low levels in many tissues and cell types and reaches high concentrations in brain and pituitary. FGF2 has been implicated in a multitude of physiologic and pathologic processes, including limb development, angiogenesis, wound healing, and tumor growth. FGF2 may be obtained commercially, for example from Invitrogen-Gibco (Grand Island, N.Y.).

Platelet Derived Growth Factor (PDGF) is a potent mitogen for a wide range of cell types including fibroblasts, smooth muscle and connective tissue. PDGF, which is composed of a dimer of two chains termed the A chain and B chain, can be present as AA or BB homodimers or as an AB heterodimer. Human PDGF-AB is a 25.5 kDa homodimer protein consisting of 13.3 kDa A chain and 12.2 B chain. PDGF AB may be obtained commercially, for example from Peprotech (Rocky Hill, N.J.).

The growth factor(s), such as FGF2 and optionally PDGF AB, may be present in the medium at concentrations of about 100 pg/ml, such as about 500 pg/ml, such as about 1 ng/ml, such as about 2 ng/ml, such as about 3 ng/ml, such as about 4 ng/ml, such as about 5 ng/ml. In some embodiments, the medium contains FGF2 at about 5 ng/ml. The medium may also contain PDGF AB, such as at about 5 ng/ml.

Splitting Cells

Cells in culture will generally continue growing until confluence, when contact inhibition causes cessation of cell division and growth. Such cells may then be dissociated from the substrate or flask, and "split", subcultured or passaged, by dilution into tissue culture medium and replating.

The methods and compositions described here may therefore comprise passaging, or splitting during culture. The cells in the cell culture may be split at a ratio of 1:2 or more, such as 1:3, such as 1:4, 1:5 or more. The term "passage" designates the process consisting in taking an aliquot of a confluent culture of a cell line, in inoculating into fresh medium, and in culturing the line until confluence or saturation is obtained.

Selection, Screening or Sorting Step

The method may further comprise a selection or sorting step, to further isolate or select for mesenchymal stem cells.

The selection or sorting step may comprise selecting mesenchymal stem cells (MSC) from the cell culture by means of one or more surface antigen markers. The use of a selection or sorting step further enhances the stringency of sorting and selection specificity for MSCs and furthermore potentially reduces possible contamination from embryonic stem cells such as hESCs and other hESC-derivatives from the starting material. This would then further reduce the risk of teratoma formation and further increase the clinical relevance of the protocol we describe.

A number of methods are known for selection or sorting based on antigen expression, and any of these may be used in the selection or sorting step described here. The selection or sorting may be achieved by means of fluorescence activated cell sorting (FACS). Thus, as known in the art, FACS involves exposing cells to a reporter, such as a labelled antibody, which binds to and labels antigens expressed by the cell. Methods of production of antibodies and labelling thereof to form reporters are known in the art, and described for example in Harlow and Lane. The cells are then passed through a FACS machine, which sorts the cells from each other based on the labelling. Alternatively or in addition, magnetic cell sorting (MACS) may be employed to sort the cells.

We have realised that while a number of candidate surface antigens known to be associated with MSCs e.g. CD105, CD73, ANPEP, ITGA4 (CD49d), PDGFRA, some of the MSC associated surface antigens e.g. CD29 and CD49e are also highly expressed in ES cells such as hESCs and their expression are verified by FACS analysis. The association of a surface antigen with MSCs may not be sufficient to qualify the antigen as a selectable marker for isolating MSCs from ES cells such as hESC. Accordingly, the selection or sorting step may employ antigens which are differentially expressed between MSCs and ES cells.

The selection or sorting step of our method may positively select for mesenchymal stem cells based on the expression of antigens. Such antigens may be identified by, for example, comparing the gene expression profiles of hESCs and hES-CMSCs. In particular embodiments, the selection or sorting may specifically make use of any of the antigens shown in Table E1A and E1B below.

The selection or sorting step of our method may positively select for mesenchymal stem cells based on the expression of antigens which are identified as expressed on MSCs, but not expressed on ES cells such as hESCs.

CD73 is highly expressed on MSCs, while being not highly expressed on hESCs. Both CD73 and CD105 are highly expressed surface antigens in MSCs and are among the top 20 highly expressed surface antigens in hESC-MSCs relative to hESC, the use of either CD73 or CD105 (or both) as selectable marker for putative MSCs will be equally effective in sorting for putative MSCs generated by differentiating hESCs.

Alternatively, or in addition, the selection or sorting step may negatively select against antigens based on surface antigens that are highly expressed as surface antigen on embryonic stem cells (ES cells) such as hESCs, and not mesenchymal stem cells e.g., hESC-MSC. Selection or sorting may be based on known or previously identified hESC-specific surface antigens such as MIBP, ITGB1BP3 and PODXL, and CD24.

FACS analysis confirms the expression of CD24 on hESC but not hESC-MSCs. Therefore, CD24 may be used as a negative selection or sorting marker either on its own, or in conjunction with CD105 as a positive selectable marker for isolating putative MSCs from differentiating hESC cultures.

EXAMPLES

Example 1

Materials and Methods—Preparation of Exosomes

Exosomes were purified from huES9.E1 derived MSCs conditioned media (CM) using HPLC as described earlier. In brief, CM collected from MSCs culture was concentrated 50× by tangential flow filtration (TFF) using a membrane with a 100 kDa MWCO (Sartorius, Goettingen, Germany).

After that, CM was passed through chromatography columns (TSK Guard column SWXL, 6×40 mm and TSK gel G4000 SWXL, 7.8×300 mm, Tosoh Corp., Tokyo, Japan).

Exosomes were collected from the first peak of the elution, concentrated using 100 kDa MWCO filter (Sartorius). Exosomes were filtered with a 0.22 μm filter before storage or use.

Example 2

Materials and Methods—LC MS/MS

Proteins in two ml of dialyzed exosomes were reduced, alkylated and tryptic digested as described (20).

The samples were then desalted by passing the digested mixture through a conditioned Sep-Pak C-18 SPE cartridge (Waters, Milford, Mass., USA), washed twice with a 3% acetonitrile (ACN) (J T Baker, Phillipsburg, N.J.) and 0.1% formic acid (FA) buffer, and eluted with a 70% ACN and 0.1% FA buffer.

The eluted samples were then dried to about 10% of their initial volumes by removing organic solvent in a vacuum centrifuge.

To reduce sample complexity, offline peptide fractionation was carried out with a HPLC system (Shimadzu, Japan) through a Polysulfoethyl SCX column (200 mm×4.6 mm) (PolyLC, USA).

Mobile phase A (5 mM KH4PO4+30% acetonitrile) and mobile phase B (5 mM KH4PO4+30% acetonitrile+350 mM KCl) at 1 ml/min.

Eight fractions were collected and dried with a vacuum centrifuge.

Fractionated samples were loaded into the auto sampler of a Shimadzu micro HPLC system coupled online to a LTQ-FT Ultra linear ion trap mass spectrometer (Thermo Electron, Bremem, Germany) fitted with a nanospray source.

Injected peptides were trapped and desalted in a Zorvax 300SB-C18 enrichment column (5 mm×03 mm, Agilent Technologies, Germany) and eluted into a nano-bored C18 packed column (75 μm×100 Å, Michrom Bioresources, Auburn, Calif.).

A 90 minute gradient at a constant flow rate of 20 μl/min with a splitter to an effective flow rate of 200 ηl/min was used to elute the peptides into the mass spectrometer.

The LTQ was operated in a data-dependent mode by performing MS/MS scans for the 8 of the most intense peaks from each MS scan in the FTMS.

For each experiment, MS/MS (dta) spectra of the eight SCX fractions were combined into a single mascot generic file by a home-written program.

Protein identification was achieved by searching the combined data against the IPI human protein database (version 3.34; 69,164 sequences, 29,064,825 residues) via an in-house Mascot server (Version 2.2.04, Matrix Science, UK).

The search parameters were: a maximum of 2 missed cleavages using trypsin; fixed modification was carbaminomethylation of cysteine and variable modification was oxidation of methionine.

The mass tolerances were set to 10 ppm and 0.8 Da for peptide precursor and fragment ions respectively.

Protein identification was accepted as true positive if two different peptides were found to have scores greater than the homology scores.

Example 3

Materials and Methods—Antibody Array

500 µl of non-conditioned media and exosomes from 3 independent preparations were assayed for the presence of cytokines and other proteins using RayBio® Biotin Label-based Human Antibody Array I according to manufacturer's instructions (RayBio, Norcross, Ga.).

The cytokines and other proteins were considered to be present in the exosomes if the signal intensity is 2 fold higher ($p<0.05$) than that in non-conditioned medium.

Example 4

Materials and Methods—Western Blot Hybridization

12 µg exosomes were separated on 4-12% SDS-polyacrylamide gels and electroblotted onto a nitrocellulose membrane.

The membrane was transferred to the membrane holder of SNAP i.d. system (Millipore, Billerica, Mass.), blocked and incubated with primary anti-human antibodies, which included mouse anti-GAPDH (1:100 dilution), mouse anti-PGK (1:60), mouse anti-PGD (1:60), rabbit anti-PFKFB3 (1:60), mouse anti-pyruvate kinase (PK, 1:200), mouse anti-20S proteasome α1-7 (1:200), mouse anti-CD73 (1:60) and mouse anti-CD59 (1:200).

The blot was then incubated with a horseradish peroxidase-coupled secondary antibody.

The secondary antibody used was goat anti-mouse IgG (1:1250) or donkey anti-rabbit IgG (1:1250).

All antibodies were obtained from Santa Cruz Biotechnology, Santa Cruz, Calif. except mouse anti-PK which was from Abcam Inc., Cambridge, Mass.

The blot was then incubated with HRP-enhanced Chemiluminescent substrate (Thermo Fisher Scientific Inc., Waltham, Mass.) and then exposed to X-ray film.

Example 5

Materials and Methods—Enzyme Assays—Pyruvate Kinase Assay

5 µg of exosome (in 12 µl) was lysed using a cell extraction kit (Biovision, Mountain view, Calif.).

The lysed exosome extract was incubated with 50 µl of reaction mix from a commercially available PK assay kit (Biovision).

In this assay, pyruvate produced by PK was oxidized by pyruvate oxidase to produce fluorescences (Ex/Em=535/587 nm).

The increase in fluorescence intensity is therefore proportional to the amount of pyruvate produced.

Example 6

Materials and Methods—Enzyme Assays—GAPDH and PGK Assay

GAPDH and PGK activity were measured based on their downstream product, ATP in the glycolysis reaction using 2 commercially available kits, KDalert GAPDH assay kit (Ambion Inc., Austin, Tex.) and ApoSENSOR ADP/ATP ratio assay kit (Biovision).

Briefly, exosomes were lysed using a cell extraction kit (Biovision).

To measure GAPDH activity, 10 µg of lysed exosomes was added to KDalert reaction buffer containing D-glyceraldehyde-3-phosphate, NAD$^+$ and P$_i$ to form 1,3-bisphosphoglycerate+NADH+H.

250 U/ml of PGK and 60 µM ADP were then added to convert 1,3-bisphosphoglycerate and ADP to 3-phosphoglycerate and ATP.

The amount of ATP produced which was proportional to GAPDH activity, was then measured using ATP luciferase assay.

To measure PGK activity, 10 µg of lysed exosomes was added to the 1,3-bisphosphoglycerate produced from the above assay.

ADP was added to allow the formation of ATP.

ATP amount which is proportional to PGK activity was then quantified using ATP luciferase assay.

Example 7

Materials and Methods—Enzyme Assays—20S Proteasome Assay

The proteasome activity was measured using a 20S proteasome activity assay kit (Millipore) based on detection of the fluorophore 7-Amino-4 methylcoumarin (AMC) after cleavage from the labeled substrate LLVY-AMC (SEQ ID NO: 15) by 20S proteasome in the presence or absence of lactacystin, a specific 20S proteasome inhibitor.

Briefly, 4 µg of exosome was incubated with a reaction buffer containing LLVY-AMC (SEQ ID NO: 15) in the presence or absence of 25 µM actacystin.

The samples and AMC standards were incubated at 37° C. and fluorescense intensity at Ex/Em=380/460 nm was monitored for 2 hours.

Example 8

Materials and Methods—Enzyme Assays—CD73 Assay

CD73 (NT5E) enzymatic activity in exosome was determined by incubating 2.5 µg of exosome in 100 µl Tris buffer pH 7.4 containing 50 µM AMP (Sigma-Aldrich, St Louis, Mo.).

The amount of phosphate ions released from the hydrolysis of AMP was then determined by Colorlock Gold kit (Innova Biosciences, Cambridge, UK) as per manufacturer's instruction.

Example 9

Materials and Methods—Cell Assays—Glycolysis

H9C2 cardiomyocytes were plated onto a 96 well plate (poly-lysine coated) at 30,000 cells per well.

After 5 hours, the cells were washed twice with Tyrode's buffer before incubating in Tyrode's buffer containing 20 µmol oligomycin (Sigma-Aldrich), 6 mmol glucose, and with or without 0.1 µg/ml exosomes for 15, 30 and 60 minutes.

Cellular ATP concentration was measured using ATPlite 1 step luminescence ATP detection assay system (PerkinElmer, Zaventem, Belgium).

Example 10

Materials and Methods—Cell Assays—Adenosine-Mediated Signaling

H9C2 cardiomyocytes were plated onto a 6 well plate at 200,000 cells per well and serum starved overnight.

The cells were then incubated with fresh serum-free medium with or without 1 mM theophylline for another hour.

In the meantime, two series of serum-free media were prepared.

One series contained no supplement, 50 μM AMP alone, 0.1 μg/ml exosomes alone or a combination of 50 μM AMP and 0.1 μg/ml exosomes.

The second series was similar to the first except that the media contained 1 mM theophylline.

Both series were incubated at 37° C. for 30 minutes.

The first series was used to replace medium of the cells that were being cultured in serum-free medium alone and the second series to those cells that were being cultured in theophylline-containing medium.

After five minutes, the cells were harvested and lysed using a commercially available mammalian cell extraction kit (BioVision) in the presence of a protease and phosphatase inhibitor cocktail 1 (Sigma Aldrich).

Protein concentration was determined by standard Bradford assay.

10 μg of the total proteins were analysed by western blot hybridization using 1:2000 dilution of rabbit anti-pERK 1/2 (Cell Signaling, 9101S), 1:2000 dilution of rabbit anti-AKT (Cell Signaling, 9271S), 1:500 dilution of rabbit anti-ERK1 (Santa Cruz, sc-94) and 1:500 dilution of rabbit anti-AKT (Cell Signaling, 9272S).

Example 11

Materials and Methods—Cell Assays—Complement-Mediated Cell Lysis

Briefly, sheep red blood cells (SRBCs) were purchased (Innovative Research, Southfield, Mich.) and washed three times with phosphate buffered saline (PBS) before resuspending at $1 \times 10^8$ cell/ml PBS.

Purified complement components, C5b6, C8 and C9 were purchased from Calbiochem (San Diego, Calif.), and C7 from Sigma-Aldrich (St Louis, Mo.).

Assembly of intact C5b-9 on SRBCs was initiated by a 15 min incubation (37° C.) with 1 ml each of C5b6 (0.1 μg/ml) and C7 (0.4 μg/ml) in the presence or absence of exosomes at a final concentration of 0.1 μg/ml.

The SRBCs were then washed and incubated with 1 ml each of C8 (0.4 μg/ml), plus C9 (0.4 μg/ml) with or without a blocking CD59 antibody at a final concentration of 0.05 μg/ml for an additional 30 min.

After that the SRBCs were centrifuged and the amount of hemoglobin released by the lysed SRBCs in the supernatant was measured by absorbance at 415 nm.

Total (100%) hemolysis was obtained by treating the cells with 1% (w/v) Triton X-100.

Example 12

Results—Proteomic Profiling of Exosome

Exosome was purified from culture medium conditioned by HuES9.E1, a human ESC-derived mesenchymal stem cells[13] by HPLC as previously described[9,10]. Proteomic profiling using mass spectrometry and antibody approaches was performed as previously described[9-11] on 3 independently prepared batches of HPLC-purified exosomes. A total of 866 proteins were detected and these proteins were denoted by their gene symbol to facilitate analysis (Table E1). Of these, 318 gene products were found in the 739 proteins previously identified in the unfractionated conditioned medium[9,10] (FIG. 1).

Based on data analysis of 15 proteomic analyses carried out on exosomes purified from cultured cells and from biological fluids, Thery et al. had observed that a set of about 17 proteins, namely glyceraldehyde 3-phosphate dehydrogenase (GAPDH), pyruvate kinase (PK), eukaryotic translation elongation factor 1A 1 (EEF1A 1), milk fat globule EGF factor 8 protein (MFGE8), tetraspanins, 14-3-3 proteins, Gα proteins, clathrin, Alix (PDCD6IP), MHC class1, annexins (ANX), Rab proteins, ezrin (VIL2), radixin (RDX) and moesin (MSN)(ERM), actin, tubulin, HSP70 and HSP90 were found to be present in at least 50% of the exosomes that were characterized[2]. Not unexpectedly, most of these proteins were also found in the proteome of the HPLC-purified MSC exosomes (Table E1). Also consistent with the endosomal origin of exosomes, we detected the presence of endosome-associated proteins such as Alix (PDCD6IP) and Rab (Table E1).

TABLE E1

Proteomic profile of 3 independently prepared exosomes as determined by LC MS/MS and antibody arrays.

| A2M | BSG | COMP | FBLN1 | HMGCS2 | KRT15 | MMP2 | PRR4 | RPS4X | TGFB1 |
|---|---|---|---|---|---|---|---|---|---|
| AB13BP | C11orf59 | COPB1 | FBN1 | HNRNPA1 | KRT16 | MMP3 | PRSS23 | RPS5 | TGFB2 |
| ACAA2 | C1orf78 | COPS3 | FBN2 | HP | KRT17 | MOS | PSMA1 | RPSA | TGFB1 |
| ACAT2 | C1R | COPS4 | FBXW8 | HPX | KRT18 | MPO | PSMA2 | RRAS2 | TGM2 |
| ACLY | C1S | COPS8 | FEN1 | HRSP12 | KRT19 | MPZL1 | PSMA3 | RTN4 | TGOLN2 |
| ACSL1 | C20orf114 | CPS1 | FERIL3 | HSP90AA1 | KRT2 | MRC2 | PSMA4 | RUVBL1 | THBS1 |
| ACTA1 | C3 | CREG1 | FGA | HSP90AB1 | KRT27 | MSN | PSMA5 | S100A11 | THBS2 |
| ACTA2 | C5orf24 | CRIPT | FGB | HSP90B1 | KRT28 | MSTN | PSMA6 | S100A13 | THY1 |
| ACTB | C9orf19 | CRTAP | FGF16 | HSPA1A | KRT3 | MXRA5 | PSMA7 | S100A8 | TIMP1 |
| ACTG2 | C9orf91 | CSF1 | FGF18 | HSPA1L | KRT4 | MYADM | PSMB1 | S100A9 | TIMP2 |
| ACTN1 | CACNA2D1 | CSF2 | FGF19 | HSPA5 | KRT5 | MYCBPAP | PSMB10 | S100P | TIMP3 |
| ACTN2 | CACNA2D4 | CSF3 | FGFRL1 | HSPA6 | KRT6A | MYH14 | PSMB2 | SAA4 | TKT |
| ACTN3 | CALR | CSPG4 | FGG | HSPA8 | KRT6B | MYH9 | PSMB3 | SASS6 | TLN1 |
| ACTN4 | CAND1 | CST4 | FLG2 | HSPB1 | KRT6C | MYL6B | PSMB4 | SCAMP3 | TMBIM1 |
| ACTR1A | CAP1 | CTA-221G9.4 | FLJ13197 | HSPD1 | KRT7 | MYO1C | PSMB5 | SCGB2A1 | TMED10 |

TABLE E1-continued

Proteomic profile of 3 independently prepared exosomes as determined by LC MS/MS and antibody arrays.

| ACTR2 | CAPNS1 | CTBP2 | FLJ22184 | HSPG2 | KRT72 | NBL1 | PSMB6 | SCYE1 | TMED9 |
|---|---|---|---|---|---|---|---|---|---|
| ACTR3 | CAPZA1 | CTNNA1 | FLJ32784 | HTRA1 | KRT73 | NEFH | PSMB7 | SDC1 | TMEM16B |
| ADAM10 | CASP14 | CTNNA2 | FLNA | HY1 | KRT74 | NEK10 | PSMB8 | SDC2 | TMEM2 |
| ADAM9 | CAT | CTNNB1 | FLNB | ICAM1 | KRT76 | NID1 | PSMB9 | SDC4 | TMEM47 |
| ADAMTS12 | CAV1 | CTNND1 | FLNC | ICAM5 | KRT77 | NLRP8 | PSMC5 | SDCBP | TMEM51 |
| AEBP1 | CCDC129 | CTSG | FLOT1 | IDH3B | KRT78 | NME1 | PSMD11 | SEC14L4 | TNC |
| AFM | CCDC64B | CXCL16 | FLOT2 | IFITM2 | KRT79 | NOMO1 | PSMD14 | SEMA5A | TNFRSF11B |
| AGRN | CCL20 | CXCL2 | FLT1 | IFNG | KRT8 | NRAS | PSMD6 | SEPT2 | TNFRSF12A |
| AHCY | CCL28 | CXorf39 | FN1 | IFRD1 | KRT80 | NRG2 | PSMD7 | SEPT7 | TNFRSF1A |
| AHNAK2 | CCL7 | CYBRD1 | FREM3 | IFT140 | KRT84 | NRP1 | PTGFRN | SERINC5 | TNFSF18 |
| AHSG | CCR4 | DBF4B | FST | IGF2R | KRT9 | NT5E | PTK7 | SERPINA1 | TPBG |
| AKR1B1 | CCR5 | DCD | FTL | IGFBP3 | LACRT | NTF4 | PTPRK | SERPINB3 | TPI1 |
| AKR7A2 | CCT5 | DCHS2 | FUCA2 | IGFBP4 | LAMA4 | NUSAP1 | PTRF | SERPINE1 | TRAP1 |
| ALB | CCT6A | DCLK2 | GALNT5 | IGFBP6 | LAMB1 | OBFC1 | PTTG11P | SERPINE2 | TREM1 |
| ALCAM | CD109 | DCN | GANAB | IGFBP7 | LAMC1 | ODZ3 | PTX3 | SERPINF1 | TREML2P |
| ALDH2 | CD151 | DCTN1 | GAPDH | IGHA1 | LAMP1 | OFD1 | PXDN | SFN | TRIM40 |

| ALDH3A2 | CD248 | DECR1 | GAPDHS | IGHA2 | LAMP2 | OPRM1 | PZP | SFRP1 | TRIM41 |
|---|---|---|---|---|---|---|---|---|---|
| ALDH6A1 | CD276 | DEFA1 | GARS | IGHG1 | LAP3 | OSM | QPCTL | SFRP4 | TSN |
| ALDH7A1 | CD40LG | DIP2B | GAS6 | IGHG2 | LCN1 | OTC | QSOX1 | SHANK3 | TSNAX |
| ALDH9A1 | CD44 | DIRAS2 | GDF1 | IGHG4 | LCN2 | OXNAD1 | RAB10 | SLAIN1 | TSPAN14 |
| ALDOA | CD47 | DKFZp686D0972 | GDF11 | IGHM | LDHA | OXTR | RAB11B | SLC16A1 | TSPAN4 |
| ALDOB | CD59 | DKK1 | GDF15 | IGJ | LDHAL6B | P4HB | RAB14 | SLC16A3 | TSPAN6 |
| ALDOC | CD63 | DKK3 | GDF3 | IGKC | LDHB | PAICS | RAB15 | SLC1A4 | TSPAN9 |
| ALOX12P2 | CD81 | DMBT1 | GDF5 | IGKV1-5 | LEPRE1 | PAN3 | RAB1A | SLC1A5 | TSTA3 |
| AMH | CD82 | DNASE1L1 | GDF9 | IGL@ | LGALS1 | PAPPA | RAB1B | SLC22A2 | TTLL3 |
| ANG | CD9 | DNPEP | GDI1 | IGLV4-3 | LGALS3 | PARP10 | RAB2A | SLC25A10 | TTN |
| ANGPTL2 | CDC2L5 | DPYS | GDI2 | IGSF8 | LGALS3BP | PARP16 | RAB33B | SLC25A13 | TTYH3 |
| ANGPTL4 | CDC42 | DPYSL2 | GFRA3 | IL10 | LGALS8 | PARVG | RAB35 | SLC2A1 | TUBA1A |
| ANPEP | CDH13 | DSP | GLDC | IL11 | LGR6 | PC | RAB39B | SLC2A3 | TUBA1B |
| ANXA1 | CDIPT | DULLARD | GLUD1 | IL13 | LIF | PCOLCE | RAB5A | SLC38A2 | TUBA1C |
| ANXA11 | CDK5R2 | ECM1 | GNA13 | IL15RA | LMNA | PDCD6 | RAB5B | SLC38A3 | TUBB |

| ANXA2 | CEACAM8 | EDA | GNA12 | IL17B | LOC124220 | PDCD6IP | RAB5C | SLC39A14 | TUBB2A |
|---|---|---|---|---|---|---|---|---|---|
| ANXA2P1 | CFB | EDG2 | GNAL | IL17RA | LOC283523 | PDGFA | RAB6A | SLC3A2 | TUBB2C |
| ANXA3 | CF1 | EDIL3 | GNAS | IL19 | LOC284297 | PDFGC | RAB7A | SLC44A1 | TUBB3 |
| ANXA4 | CFL1 | EEA1 | GNAT3 | IL1F9 | LOC388344 | PDGFRB | RAB8A | SLC44A2 | TUBB6 |
| ANXA5 | CFL2 | EEF1A1 | GNB1 | IL1RAP | LOC389827 | PDIA3 | RAB8B | SLC7A10 | UBA52 |
| ANXA6 | CFTR | EEF1G | GNB2 | IL1RAPL1 | LOC442497 | PEBP1 | RAC1 | SLC7A5 | UBB |
| ANXA7 | CHMP2A | EEF2 | GNB4 | IL1RL2 | LOC653269 | PFAS | RAC2 | SMAD4 | UBE1 |
| AP1S1 | CHRDL1 | EFEMP2 | GNG12 | IL22RA1 | LOC727942 | PFKFB3 | RAD21 | SMARCA4 | UBE2N |
| APEH | CHST12 | EHD1 | GNPDA1 | IL23A | LOC728320 | PFN1 | RALA | SMC1A | UGP2 |
| APOA1 | CITED1 | EHD2 | GOT2 | IL3 | LOC728378 | PFN2 | RAN | SORT1 | UNC13B |
| APOE | CLASP2 | EHD4 | GPC1 | IL5 | LOC730013 | PGAM2 | RAP1A | SOS1 | UNC45A |
| APP | CLDN1 | EIF4A1 | GPC5 | IL6 | LOXL2 | PGD | RAP1B | SPACA1 | VAMP3 |
| ARF1 | CLEC11A | EMILIN1 | GP1 | IL6ST | LRP1 | PGK1 | RAP1B | SPARC | VANGL1 |
| ARF4 | CLIC1 | ENC1 | GPR112 | IL7 | LRP6 | PGLYRP2 | RAP2C | SPOCK1 | VASN |

| ARF5 | CLIC6 | ENG | GREM1 | IL8 | LRRF1P2 | PIGR | RARRES1 | SPRY4 | VAT1 |
|---|---|---|---|---|---|---|---|---|---|
| ARHGAP18 | CLPX | ENO1 | GRM2 | INHBA | LTBP1 | PIP | RASA1 | SPTAN1 | VCAN |
| ARHGAP23 | CLSTN1 | ENO2 | GRM3 | INHBB | LTBP2 | PITX3 | RASA4 | SPTBN1 | VCL |
| ARHGD1A | CLTA | ENO3 | GRM7 | INSR | LTF | PKM2 | RB1CC | SPTBN4 | VCP |
| ARHGEF1 | CLTC | ENTPD4 | GSN | IQGAP1 | LYAR | PLAU | RCOR2 | SRGN | VEGFC |
| ARL6IP5 | CLTCL1 | EPB41L3 | GSTM1 | ITGA11 | LYZ | PLEC1 | RDH5 | SRI | VIL1 |
| ARMS2 | CLU | EPHA2 | GSTM2 | ITGA2 | MAMDC2 | PLEKHG3 | RFTN1 | SRPX2 | VIL2 |
| ARPC3 | CM1P | EPO | GSTM5 | ITGA3 | MAP1A | PLOD1 | RGN | ST6GALNAC6 | VIM |
| ARPC4 | CNGB1 | EPX | GSTO1 | ITGA4 | MAP2K6 | PLOD2 | RHOC | STAT1 | VTI1A |
| ARPC5 | CNOT6 | ESM1 | GSTP1 | ITGA5 | MAP3K1 | PLOD3 | RMND5A | STC1 | VTN |
| ASH1L | CNTN1 | ETFB | GTPBP2 | ITGAL | MARCKS | PLP2 | RNF123 | STC2 | WDR49 |
| ASL | COL12A1 | F2R | GYLTL1B | ITGAV | MARCKSL1 | PLSCR3 | RNF40 | STOM | WDR52 |
| ATP1A1 | COL14A1 | F3 | GZMA | ITGB1 | MAT1A | PLTP | RPL10A | STOML3 | WNT5A |
| ATP1B3 | COL18A1 | F8 | H2AFV | ITGB5 | MBD3 | PLUNC | RPL12 | STX12 | YBX1 |

TABLE E1-continued

Proteomic profile of 3 independently prepared exosomes as determined by LC MS/MS and antibody arrays.

| ATP2B1 | COL1A1 | FADD    | H2AFX     | IT1H2   | MCC    | PNO1   | RPL15 | STX2   | YWHAB  |
|--------|--------|---------|-----------|---------|--------|--------|-------|--------|--------|
| ATP2B4 | COL1A2 | FAH     | HBB       | IT1H4   | MCM10  | PODN   | RPL18 | SURF4  | YWHAE  |
| ATP5A1 | COL2A1 | FAM108A1| HBE1      | ITPR2   | MDH1   | POLN   | RPL23 | SVEP1  | YWHAG  |
| ATP5B  | COL3A1 | FAM129B | HDAC5     | JUP     | MDH2   | POSTN  | RPL29 | SYT1   | YWHAQ  |
| ATP8B3 | COL4A1 | FAM29A  | HERC5     | KIAA0146| ME1    | POTE2  | RPL35A| SYT9   | YWHAZ  |
| ATRN   | COL4A2 | FAM3B   | HGF       | KIAA0256| MECP2  | PP1A   | RPLP0 | TAAR2  | ZBTB4  |
| ATXN1  | COL4A3 | FAM64A  | HISPPD2A  | KIAA0467| MET    | PP1B   | RPS10 | TAGLN  | ZNF134 |
| AXL    | COL5A1 | FAM71F1 | HIST1H2AE | KIAA1881| MFAP4  | PPME1  | RPS16 | TALDO1 | ZNF503 |
| BASP1  | COL5A2 | FAP     | HIST1H2BA | KPNB1   | MFGE8  | PPP1CC | RPS18 | TAS2R60| ZNF614 |
| BDNF   | COL6A1 | FASN    | HIST1H2BL | KRT1    | MFSD2  | PRDM16 | RPS2  | TCN1   |        |
| BGN    | COL6A2 | FAT     | HIST1H4H  | KRT10   | MIF    | PRDX1  | RPS24 | TF     |        |
| BHMT2  | COL6A3 | FAT2    | HIST2H2BE | KRT13   | MMP1   | PRDX6  | RPS27A| TFG    |        |
| BRMS1  | COL7A1 | FAT4    | HLAA      | KRT14   | MMP10  | PRNP   | RPS3  | TFRC   |        |

Black font - Identified by LC MS/MS.
Underline - Identified by antibody arrays.
Grey shade - Identified by LC MS/MS and was found to be present in at least 50% of exosomes characterized[2]

Example 13

Results—Computational Analysis of Exosome Proteome

Figure 2:
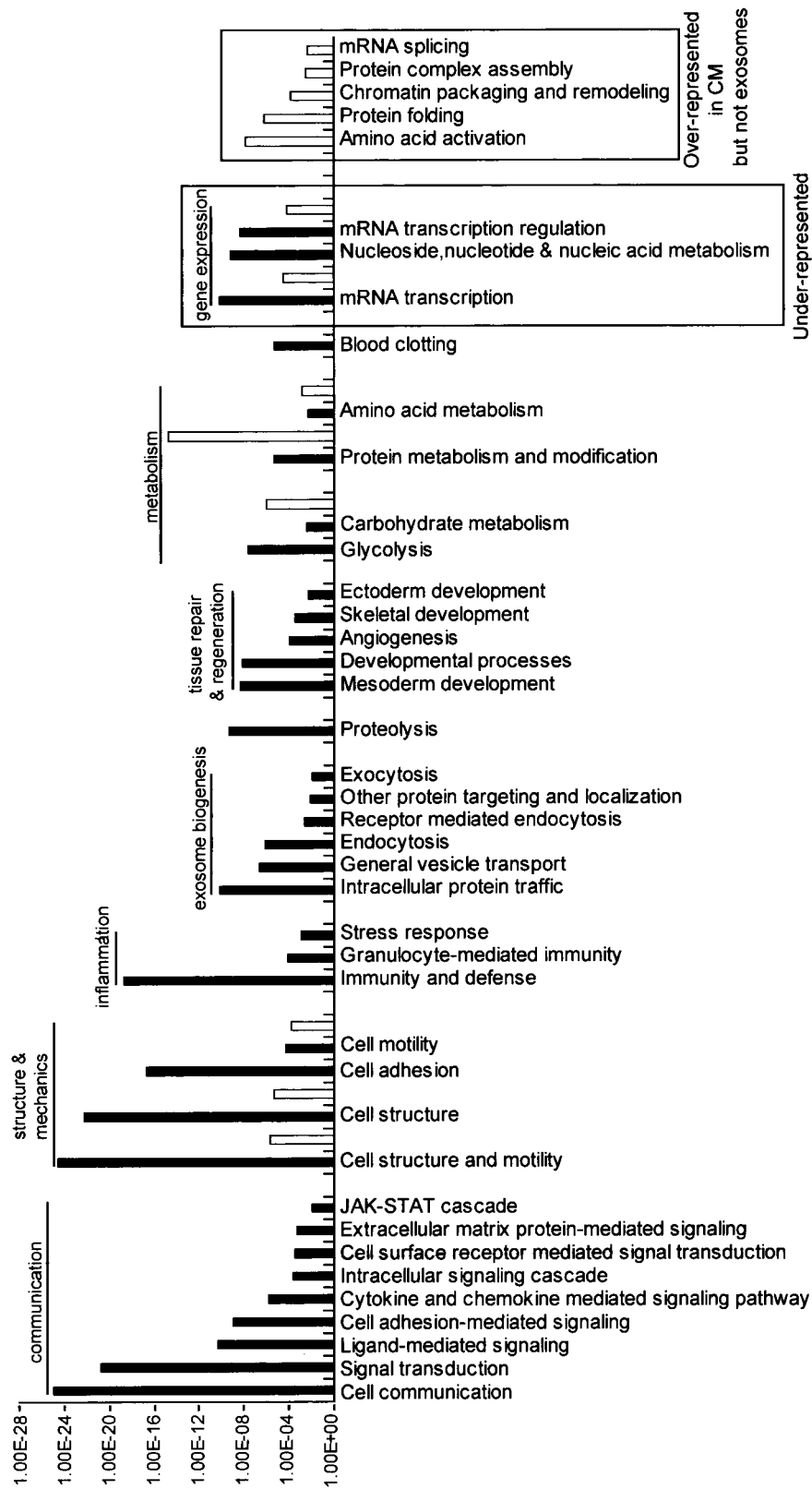
FIG. 2 is a diagram showing proteomic analysis of exosome proteins. The 866 gene products in exosomes were functionally clustered into 32 over-represented and three under-represented biological processes (p<0.001). The 421 proteins found in the conditioned medium (CM) but not in the exosome were functionally clustered into 11 over-represented and 2 under-represented biological processes. Black bars represent processes for gene products in the exosomes and white bars represent processes for gene products in the CM but not exosomes.

To better understand the biological significance of the proteins in the exosomes, functional clustering of the 866 proteins into biological processes was performed using PANTHER (Protein ANalysis THrough Evolutionary Relationships) analytical software[14,15]. The observed frequency of genes from the exosome proteome in each biological process was compared with the reference frequency of genes in the NCBI database for that biological process. The 866 gene products could be clustered into 32 biological processes that were over-represented (p<0.001) and 3 that were under-represented (p<0.001) (FIG. 2).

These biological processes could be further classified into several activities associated with exosome biology e.g. communication, cellular motility, inflammation and exosome biogenesis. As exosomes are generally postulated to function as vehicles of intercellular communication and morphogen signaling[4,16] and mediators of immune activity[2], the involvement of exosome proteins in signal transduction pathways, cell structure, cell motility and immune responses was not unexpected. A fourth class of processes that we tentatively termed as "exosome biogenesis" essentially reflected the biogenesis and release of exosomes through the involvement of endosomes, ESCRT-mediated sorting and the formation of multivesicular bodies, and fusion with the plasma membrane. Therefore, proteins such as those involved in trans-golgi network, intracellular protein traffic, general vesicle transport, endocytosis, receptor-mediated endocytosis, other protein targeting and localization and exocytosis are not unexpectedly enriched in exosomes. Other biological processes that we classified as tissue repair and regeneration include those that are involved in the development and differentiation of mesodermal and ectodermal tissues including skeletal development and angiogenesis. These biological processes are consistent with the differentiation potential of mesenchymal stem cells[17] and reflected the cellular origin of the exosomes. In our classification of metabolism, we included processes involved in catabolic or anabolic metabolisms that produce energy and building blocks for growth and regeneration. Blood clotting was also a significantly over-represented biological process that we postulated may be important in ameliorating tissue injury. All three under-represented biological processes were not unexpectedly involved in regulating gene expression at the transcriptional level. Most proteins involved in these processes tend to be transported efficiently into the nucleus, making them less likely to be associated with exosomes. We also observed that 421 proteins found in the conditioned medium (CM) were not present in the exosome (FIG. 1) and these proteins could be functionally clustered into eleven over-represented and two under-represented biological processes. Of the over-represented processes, six were also found in the clustering of the 866 proteins found in exosomes while the remaining five, namely amino acid activation, protein folding, chromatic packaging and remodeling, protein complex assembly and mRNA splicing were not. The two under-represented biological processes were also found to be under-represented for the exosome proteins. The diverse array of proteins in MSC exosomes indicated that they have the potential to participate in a wide spectrum of biochemical and cellular activities. To test this hypothesis, we selected those proteins for which assays to test their biochemical and cellular activities are available, and that together would provide an indication for the wide diversity in activities of exosomes.

Example 14

Results—Exosome Enhanced Cellular ATP Production Through Glycolysis

Figure 3A:
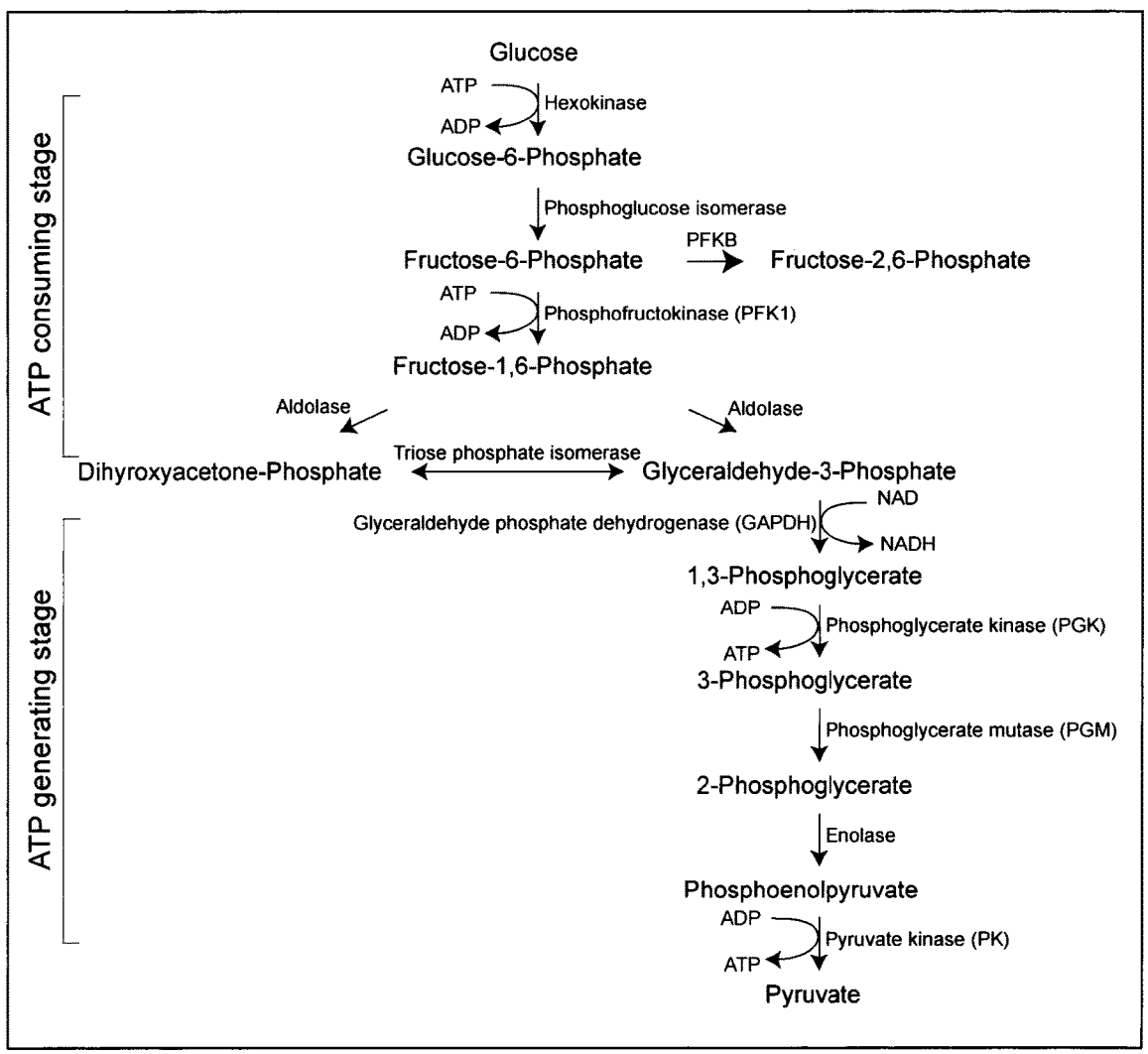
FIGS. 3A to 3D are diagrams showing that exosomes regulate glycolysis.
Figure 3B:
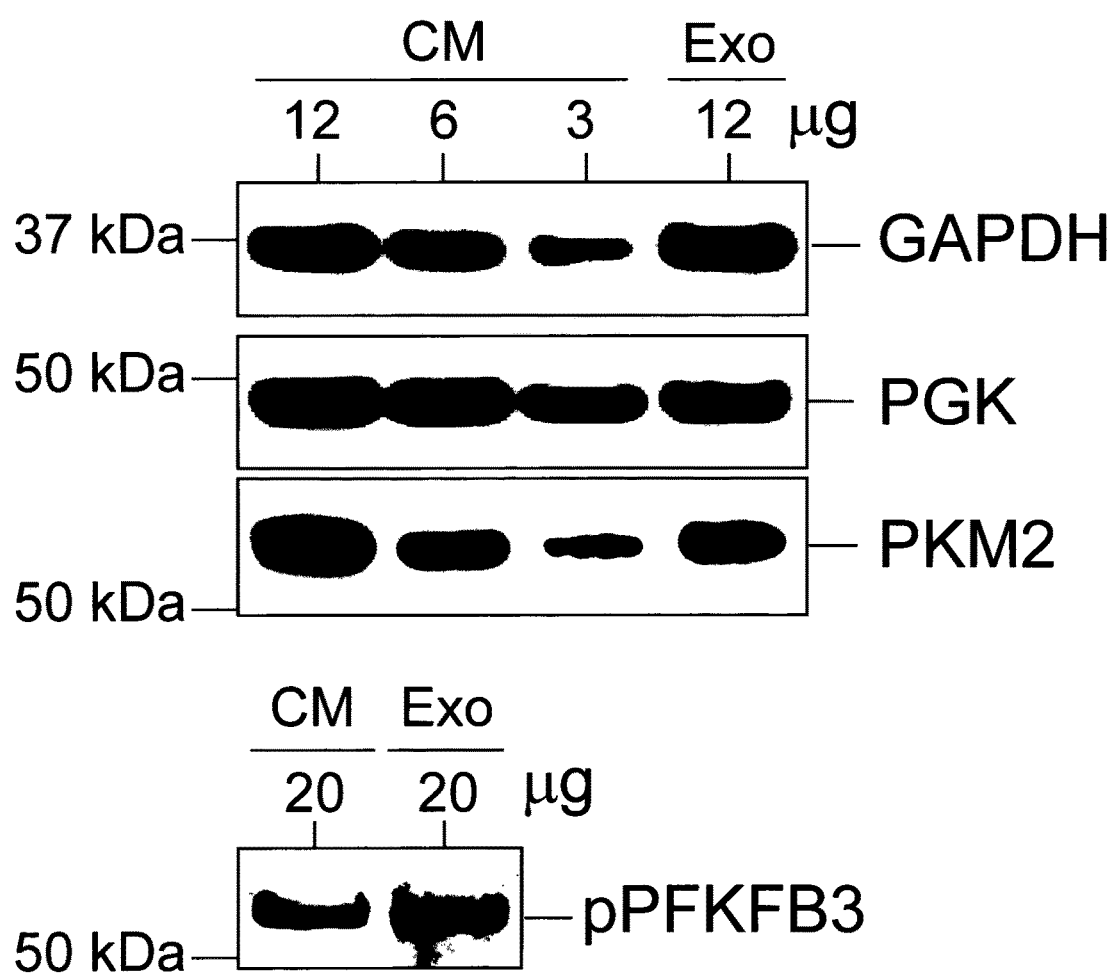
Figure 3C:
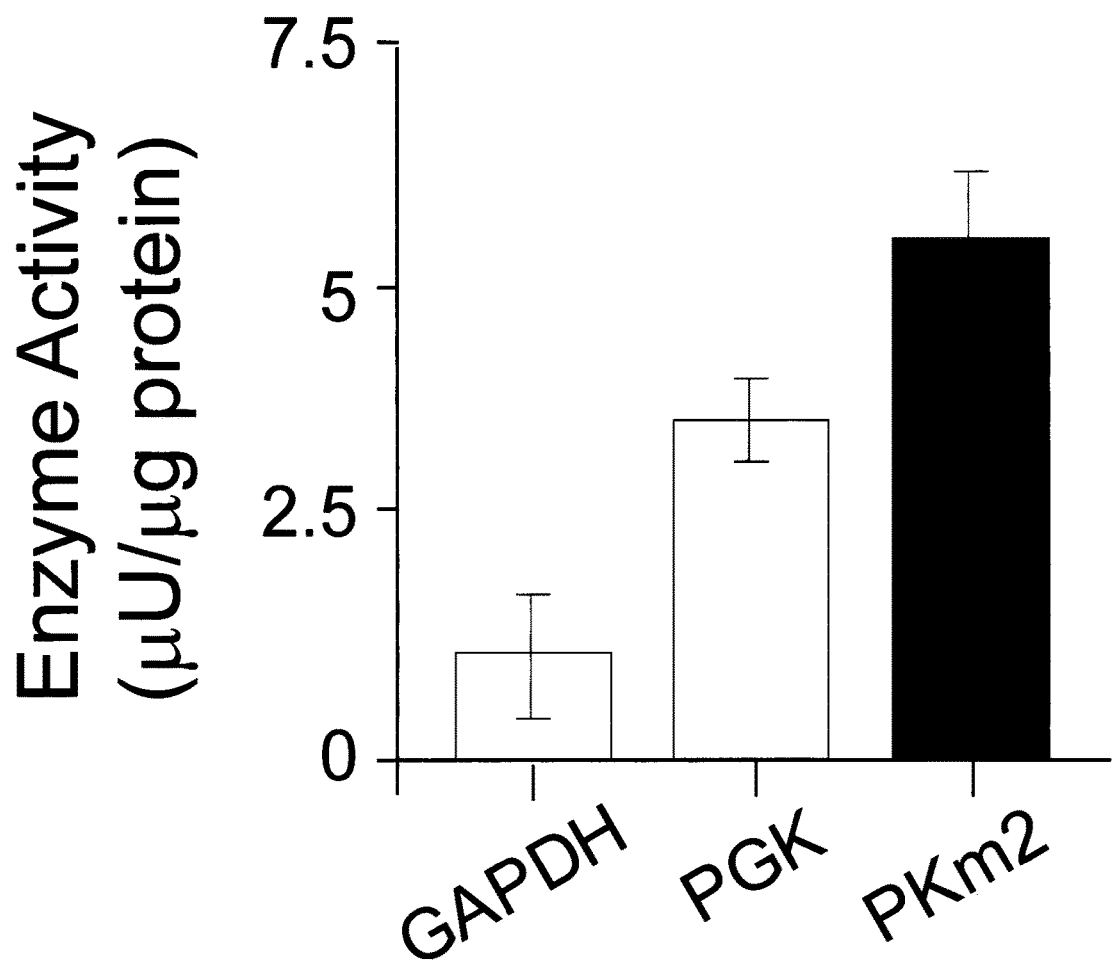
Figure 3D:
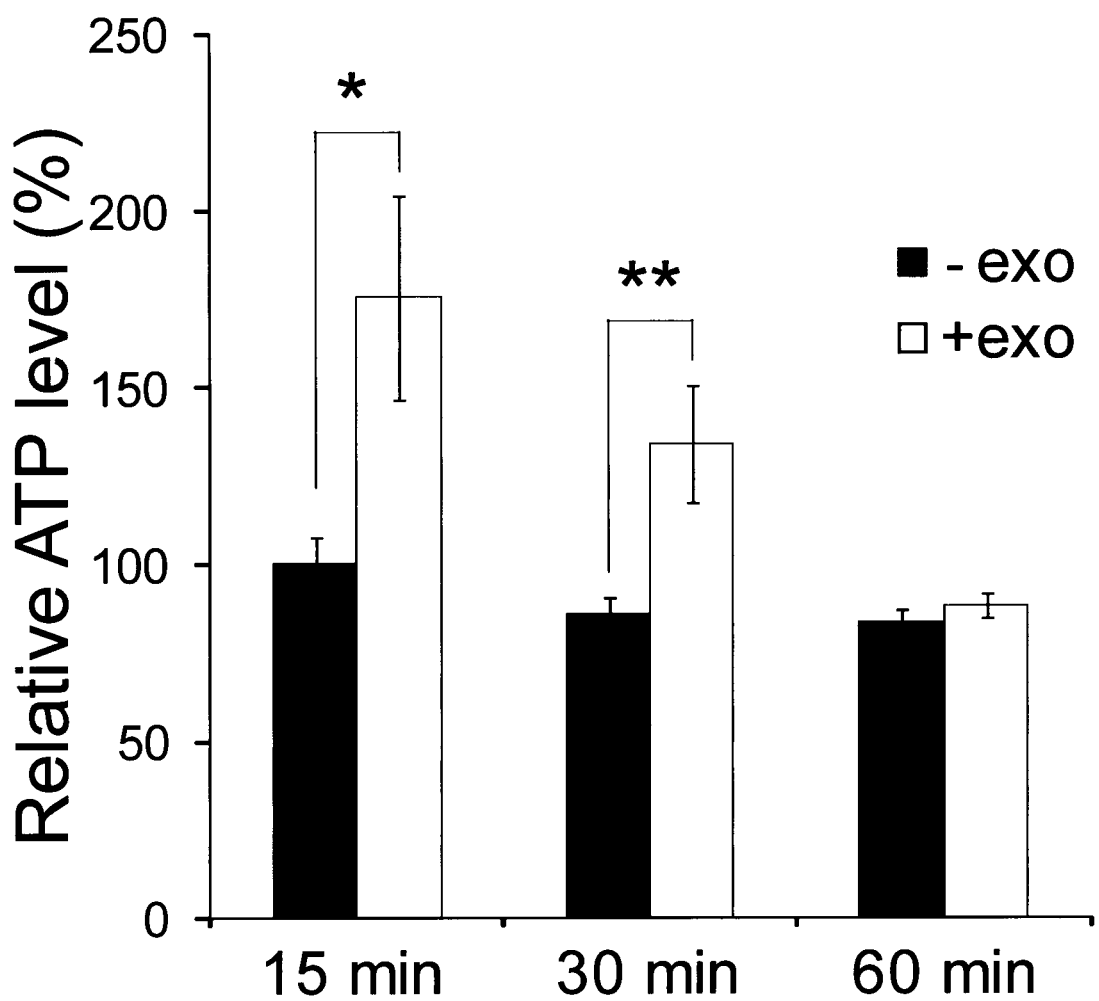

One prominent feature of the exosome proteome was the presence of all five enzymes in the ATP generating stage of the glycolysis (FIG. 3A): glyceraldehyde 3-phosphate dehydrogenase (GAPDH), phosphoglycerate kinase (PGK), phosphoglucomutase (PGM), enolase (ENO) and pyruvate kinase m2 isoform (PKm2). Of these, the three enzymes that generate either ATP or NADH namely GAPDH, PGK, and PKm2 were further confirmed to be present by immunoblotting (FIG. 3B). Their enzymatic activities were determined to be 1.1 µU, 3.59 µU and 5.5 µU per µg protein respectively (FIG. 3C) where 1 unit (U) of enzyme activity is defined as the activity required for the production of 1 µmole of product per minute.

In addition, exosome contains PFKFB3 which converts fructose 6-phosphate to fructose 2,6-bisphosphate. PFKFB3 is one of four PFKFB isoforms encoded by four different genes, PFKFKB1, 2, 3 and 4. PFKFBs are responsible for maintaining the cellular level of fructose-2,6-bisphosphate, a powerful allosteric activator of phosphofructokinase[18] which catalyses the commitment to glycolysis. They are thought to be responsible for the high glycolytic rate or "Warburg effect" in cancer cells[19]. The kinase activity of PFKFB3 is upregulated by phosphorylation by protein kinases such as cAMP-dependent protein kinase and protein kinase C. Mass spectrometry analysis revealed the presence of PFKFB3 in the exosome and immunoblotting further demonstrated that this enzyme was phosphorylated (FIG. 3A).

The presence of ATP-generating glycolytic enzymes and phosphorylated PFKFB3 in exosomes predicted that exposure of cells to exosome could increase glycolytic flux and increase ATP production. To test this, we determined if these exosomes could increase ATP synthesis in oligomycin-treated H9C2 cells. Since oligomycin inhibits mitochondrial ATPase[20], oligomycin-treated cells would have to utilize glycolysis as their major source of cellular ATP. Consistent with the presence of glycolytic enzymes and PFKFB3, and our previous demonstration that H9C2 cells could internalize MSC exosomes[12], exosomes increased ATP level in oligomycin-treated cells by 75.5±28.8% or 55.8±16.5% in 15 to 30 minutes of exposure to exosomes respectively through increased glycolysis.

Example 15

Results—20S Proteasome in Exosome is Enzymatically Active

Figure 4A:
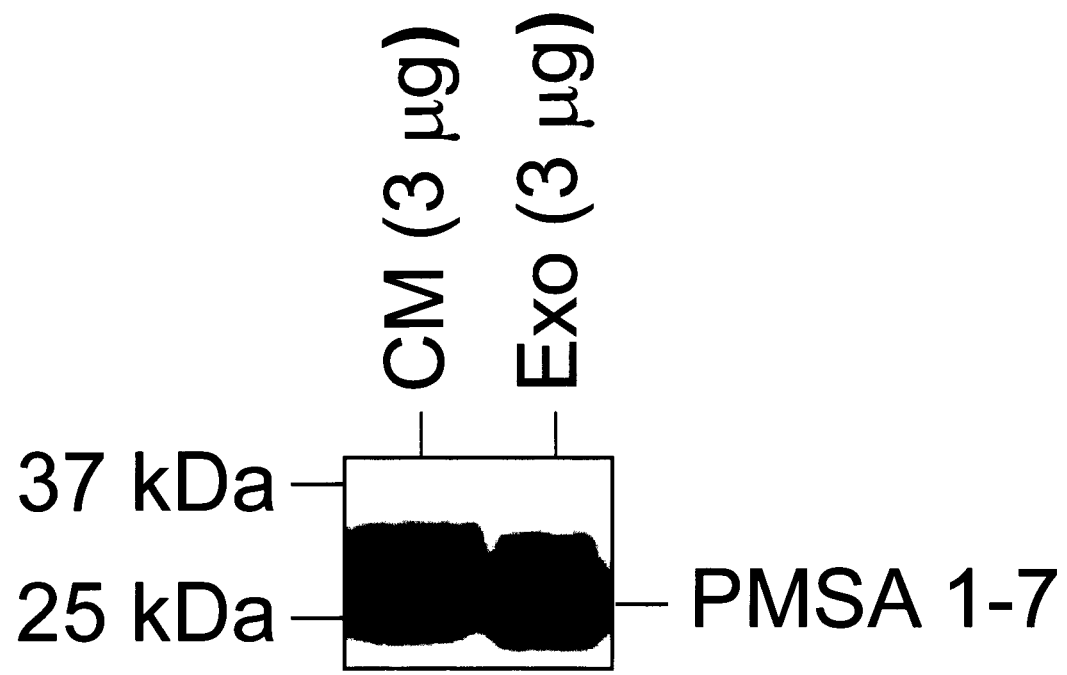
FIGS. 4A and 4B are diagrams showing 20S proteasome in exosome.

Mass spectrometry analysis of MSC exosomes not only detected the presence of all seven α- (PMSA1-7) and all seven β-subunits (PMSB1-7) of the 20S core particle, but also the three beta subunits of "immunoproteasome", PMSB8 (β5i or LMP7), PMSB9 (β1i or LMP2), PMSB10 (β2i or LMP10) gene product[21]. The presence of some of the 20S proteasome peptides was further confirmed by western blot hybridization (FIG. 4A). The presence of all seven α- and all seven β-subunits of the 20S core particle suggest that MSC exosomes contain intact 20S proteasome complexes and therefore potentially possess 20S proteasome enzymatic activity.

Figure 4B:
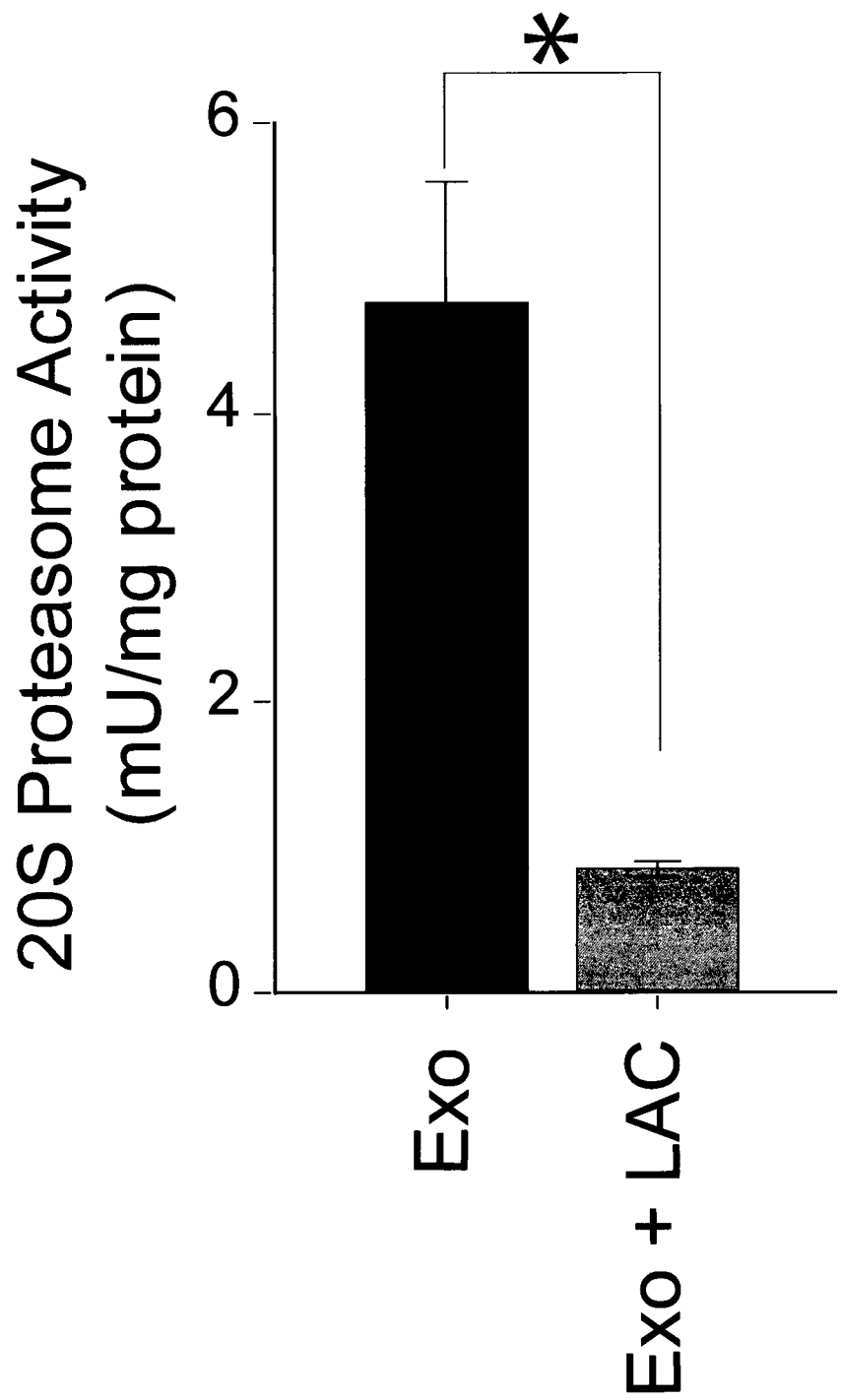

Consistent with this, MSC exosome was able to degrade short fluorogenic peptides with an enzymatic activity of 5.00 μU/μg protein and this degradation was inhibited by lactacystin, a specific proteasome inhibitor (FIG. 4B). We also observed that unlike the glycolytic enzyme assays described above, 20S proteasome activity in the exosomes could be detected without lysing the exosomes. This suggested that the 20S proteasome may be present on the surface and not in the lumen of exosomes It was previously observed that 20S proteasome preferentially assembles in an "end-on" configuration on phosphatidylinositol lipid monolayer, ER and Golgi lipid films[22] such that entrance to 20S proteasome is perpendicular to membrane. Therefore, this together with our observations suggests that 20S proteasomes in the exosomes were attached to external membrane surface and their entrances were perpendicular to the exosome membrane.

Example 16

Results—Exosome Phosphorylated ERK and AKT Via NT5E (CD73) Ecto-5'-Ectonucleotidase Ecto-5'-nucleotidase (NT5E or CD73) together with ectoapyrase (CD39) enzymatically convert precursor nucleotides into adenosine. During cellular injury, cells release ATP and ADP[23]. CD39 hydrolyzes extracellular ATP and ADP to AMP which is then degraded to adenosine by ecto-5'-nucleotidase.

Adenosine has a half-life of ten seconds in human blood. It is a powerful vasodilator but is not used clinically as a vasodilator as it is very short acting. It is used for the rapid treatment of supraventricular tachycardias. Adenosine is an endogenous purine nucleoside that modulates many physiological processes through four known adenosine receptor subtypes (A1, A2A, A2B, and A3)[24].

Figure 5A:
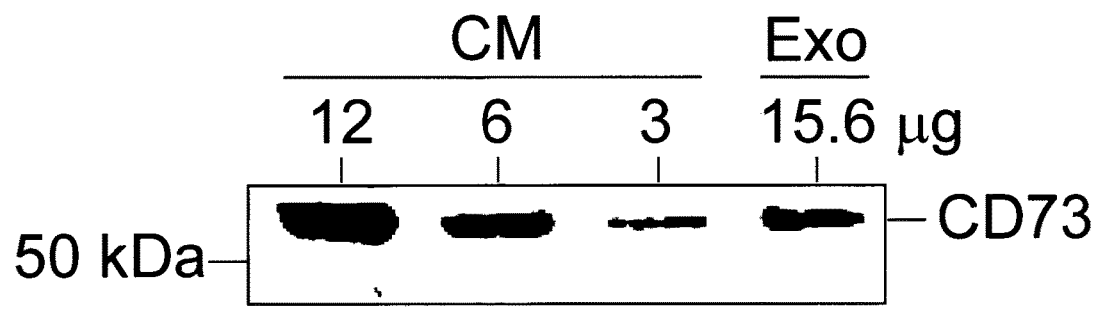
FIGS. 5A to 5C are diagrams showing exosome phosphorylated ERK and AKT via NT5E (ecto-5'-ectonucleotidase CD73).
Figure 5B:
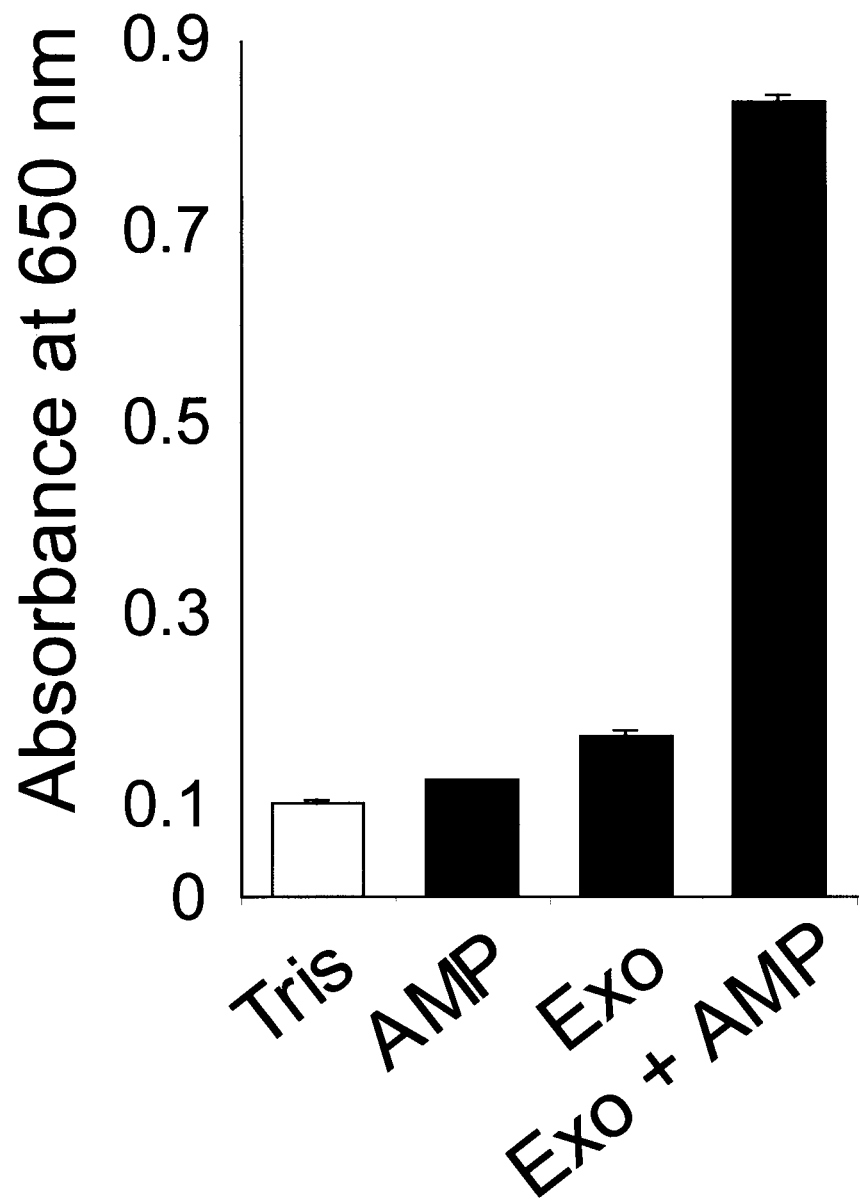
Figure 5C:
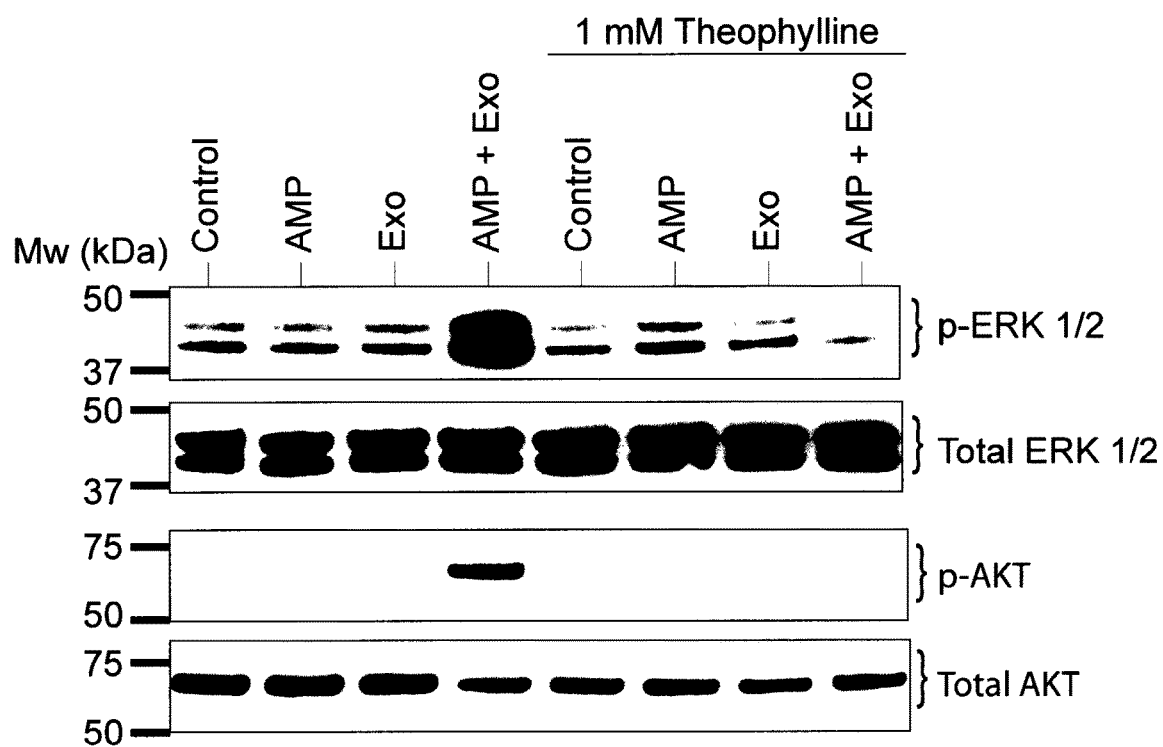

NT5E was found to be present in the MSC exosomes by mass spectrometry analysis and confirmed by immunoblotting (FIG. 5A). Their enzyme activities were determined to be 22.04 μU/μg protein. To determine if exosomes could activate adenosine signaling in cells via CD73-mediated hydrolysis of AMP, H9C2 cardiomyocytes were serum starved overnight and then exposed to exosomes and AMP. Cell lysates were then analyzed for phosphorylation of ERK1/2 and AKT (FIG. 5B, FIG. 5C).

After overnight serum starvation, exposure to exosomes and AMP induced phosphorylation of ERK1/2 and AKT. The phosphorylation of ERK1/2 and AKT was abolished in the presence of theophylline, a non-selective adenosine receptor antagonist, antagonized A1, A2A, A2B, and A3 receptors[25].

Example 17

Results—Exosome Inhibited the Formation of Membrane Attack Complex

The complement system is a part of the innate immune system which complements the function of antibodies. Upon activation, a biochemical cascade is initiated to generate several key products: C3b which binds to the surface of pathogens and enhance phagocytosis of these pathogens; C5a which helps to recruit inflammatory cells by chemotaxis; and C5b which initiates formation of the MAC consisting of C5b, C6, C7, C8, and polymeric C9. MAC deposited on the target cell forms a transmembrane channel which causes subsequent cell lysis. Aberrant activation of the complement pathway is thought to play a deleterious role in ischemia reperfusion injury[26].

Figure 6A:
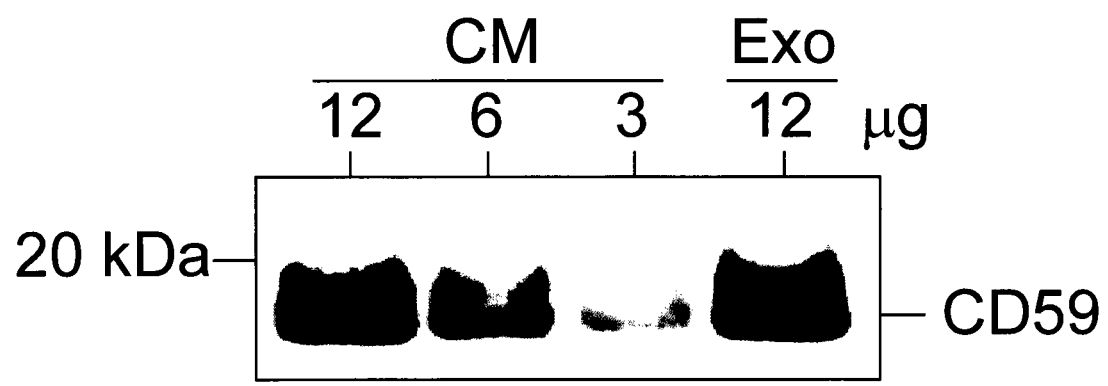
FIGS. 6A to 6B are diagrams showing exosome inhibited the formation of membrane attack complex (MAC).
Figure 6B:
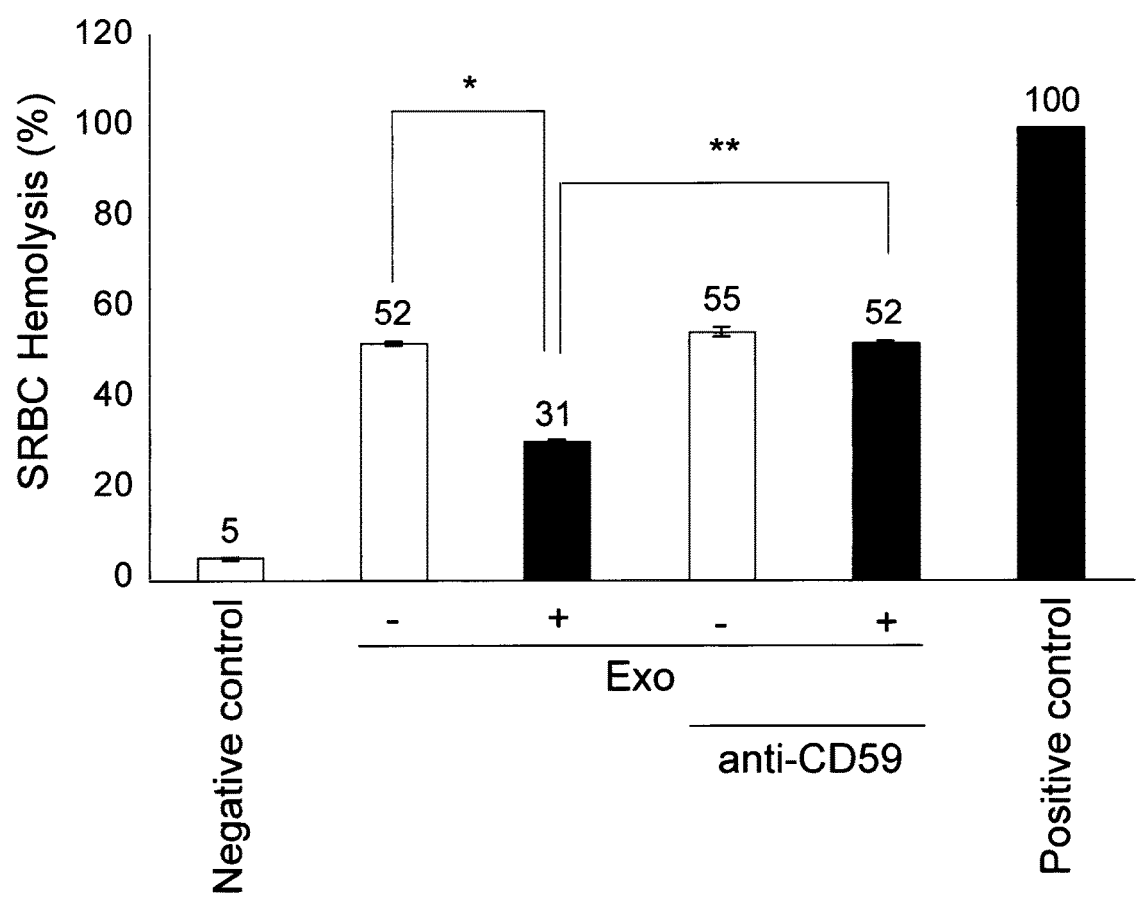

MSC exosome was found to contain CD59 by mass spectrometry analysis and this was confirmed by immunoblotting (FIG. 6A). Since CD59 inhibits formation of MAC[27], this suggested that exosomes may inhibit complement activation and subsequent complement-mediated cell lysis. Consistent with this hypothesis, exosome inhibited complement-mediated lysis of sheep red blood cells (SRBCs) (FIG. 6B). This inhibition was abolished when a CD59 blocking antibody was used to pre-treat the exosomes, showing that CD59 of exosomes is directly involved in the inhibition of complement lysis.

Example 18

Discussion (for Examples 1 to 17)

In this report, we profiled the proteome of 3 independently prepared, HPLC-purified ESC-derived MSC exosome using mass spectrometry and cytokine array and identified 866 proteins. These proteins included many proteins commonly found in other exosomes.

Clustering of these proteins according to their functions suggested that the exosome has the potential to drive many biological processes. To evaluate this hypothetical biological potential, we examined a set of proteins selected on the basis that assays for their biochemical and cellular activities are available, and that as a group, they would illustrate the wide ranging diversity in activities. More importantly, the biochemical and cellular activities of these selected proteins could potentially ameliorate tissue injury in acute myocardial ischemia/reperfusion injury.

The proteome of MSC exosomes contained a diverse array of proteins. A significant fraction are proteins that are involved in the highly regulated and complex intracellular membrane trafficking and sorting through the biosynthetic and endocytotic pathways[28] and the presence of these proteins are probably a reflection of the biogenesis of exosomes which are essentially small bi-lipid membrane vesicles secreted by many cell types. It was previously observed that exosomes from different cellular sources carry a common set of proteins, many of which are reflective of their biogenesis[29]. The complexity in the biogenesis of exosome and selective loading of the protein and RNA cargo load suggest a heavy investment of cellular resources and such commitment must be underpinned by important physiological functions.

Although exosomes have been discovered for more than 30 years, the biological significance of exosome is just starting to be uncovered. It has been implicated in an increasing number of important physiological and pathological processes such as disposal of unwanted protein[1], antigen presentation[30], genetic exchange[31], immune responses[32,33] and tumor metastasis[32-37]. Together, these observations suggest that as a group or individually, exosomes may modulate many biological processes. The latter possibility is supported by the wide array of proteins and RNAs that has been found in exosomes[12,38]. In addition to the functions of exosomes listed above, we have recently observed that exosomes secreted by MSCs could reduce infarct size in a mouse model of acute myocardial ischemia/reperfusion injury[9]. To investigate and elucidate the underlying molecular mechanism, we undertook a systematic proteomic interrogation of the MSC exosomes to reveal the cellular and biochemical potential of these exosomes and to identify candidate biological activities that could ameliorate tissue injury in acute myocardial ischemia/reperfusion injury[9].

We first determined that the glycolytic enzymes that are responsible for generating ATP and NADH[18], were not only present in the exosomes but were also biochemically active. In addition, the exosomes also contained the active phosphorylated form of PFKB3 that catalyzed the formation of fructose-2,6-bisphosphate, a powerful allosteric activator of phosphofructokinase These observations indicated that MSC exosomes have the potential to restore cellular ATP and NADH through glycolysis, independent of mitochondrial function. Besides being the major site of ATP production, mitochondria is also the major organelle in regulating cell death[39]. Loss of mitochondrial function and subsequent depletion of ATP generally represent the early steps in the cascade leading to cell death during pathological conditions such as acute myocardial ischemia/reperfusion injury. ATP deficiency, a major index of cell viability, is the key consequence of mitochondrial dysfunction. Since MSC exosomes could be internalized by cells[12], exosome has the potential to restore cellular ATP level by increasing cellular content of glycolytic enzymes or phosphorylated PFKB3 in cells with mitochondrial damage. Indeed, when mitochondrial ATPase in H9C2 cells was inhibited by oligomycin, exosomes could increase ATP production in these cells.

The presence of all seven α and β subunits that together constitute the 20S proteasome and the subsequent validation of 20S proteasome enzymatic activity in the exosomes suggested that the therapeutic activity of MSC exosomes could be partly attributed to the presence of 20S proteasome. 20S proteasome is responsible for the degradation of about 90% of all intracellular oxidatively damaged proteins[40] and reduced proteasomal activity has been postulated to be a contributing factor in the pathogenesis of aging-related neurodegenerative diseases such as Alzheimer's disease and Parkinson's disease[41,42] or cardiovascular disease[43-45].

The biochemical potential of MSC exosomes to hydrolyze AMP to adenosine by CD73 and to subsequently induce phosphorylation of AKT and ERK1/2 through the adenosine receptor illustrated the capacity of MSC exosomes to hydrolyze AMP released by distressed cells and stimulated survival signaling pathways. A recent position paper from the European Society of Cardiology highlighted the activation of adenosine receptor and phosphorylation of the pro-survival kinases such as PI3 kinase-AKT and ERK1/2 as possibly having a role in the limiting reperfusion injury[46]. Therefore, the activation of adenosine receptor which has been shown to be cardioprotective[46,47] may also be a molecular mechanism mediating the amelioration of reperfusion injury by exosomes.

The inhibition of complement-mediated lysis of red blood cells by CD59 on exosomes represents yet another candidate mechanism for the cardioprotective effect of the exosome. Complement activation is a known mediator of ischemia/reperfusion injury in tissues such as intestines, heart and kidney, and its attenuation or inhibition has been shown to ameliorate tissue injury[48-50].

In summary, our interrogation and biochemical validation of the exosome proteome have uncovered a diverse range biochemical and cellular activities, and identified several candidate pathways for the cardioprotective effect of the exosome. Further validation studies in appropriate animal models will be required to determine if one or more of these candidate pathways contributed to the efficacy of MSC exosome in reducing reperfusion injury in the treatment of acute myocardial injury[51]. The multitude of biochemical potentials in MSC exosomes provides for the possibility of simultaneously targeting more than one mediator of tissue injury and potentially inducing a therapeutic synergy similar to that observed in combination drug therapy. This possibility of being able to target multiple mediators of injury is further enhanced by the use of enzymes to drive these targeting activities. Since enzyme activities are dictated by their microenvironment e.g. substrate concentration or pH, the enzyme-based therapeutic activities of exosomes could be activated or attenuated in proportion to the severity of disease-precipitating microenvironment. Consequently, the efficacy of exosome-based therapeutics could be highly responsive to and yet limited by the disease precipitating micro-environment. Together, these features could render exosome-based therapeutics intrinsically safer and more efficacious.

Example 19

Results—Activation of TLRs by MSC Exosomes

MSC exosomes were first assessed for their potential to activate TLRs using two cell lines derived from THP-1, a human acute monocytic leukemia cell line known to express most of the human TLRs. The first line is THP1-XBlue with a stably transfected secreted embryonic alkaline phosphatase (SEAP) reporter gene under the transcriptional control of NF-kB promoter. The second line is THP1-XBlue-defMYD that is deficient in MyD88 activity such that the activation of THP1-XBlue and not THP1-XBlue-def-MYD indicates the presence of TLR ligands. At 0.1 µg/ml, MSC exosomes activated THP1-XBlue to the same extent as 0.01 µg/ml LPS and this activation unlike that of LPS was not abolished by polymyoxin B, ruling out LPS contamination in the MSC exosome preparation. Both MSC exosomes and LPS failed to activate THP1-XBlue-defMYD indicating that the activation of THP1-XBlue was mediated solely by activation of some of the TLRs present on THP-1 cells (FIG. 6).

Figure 7:
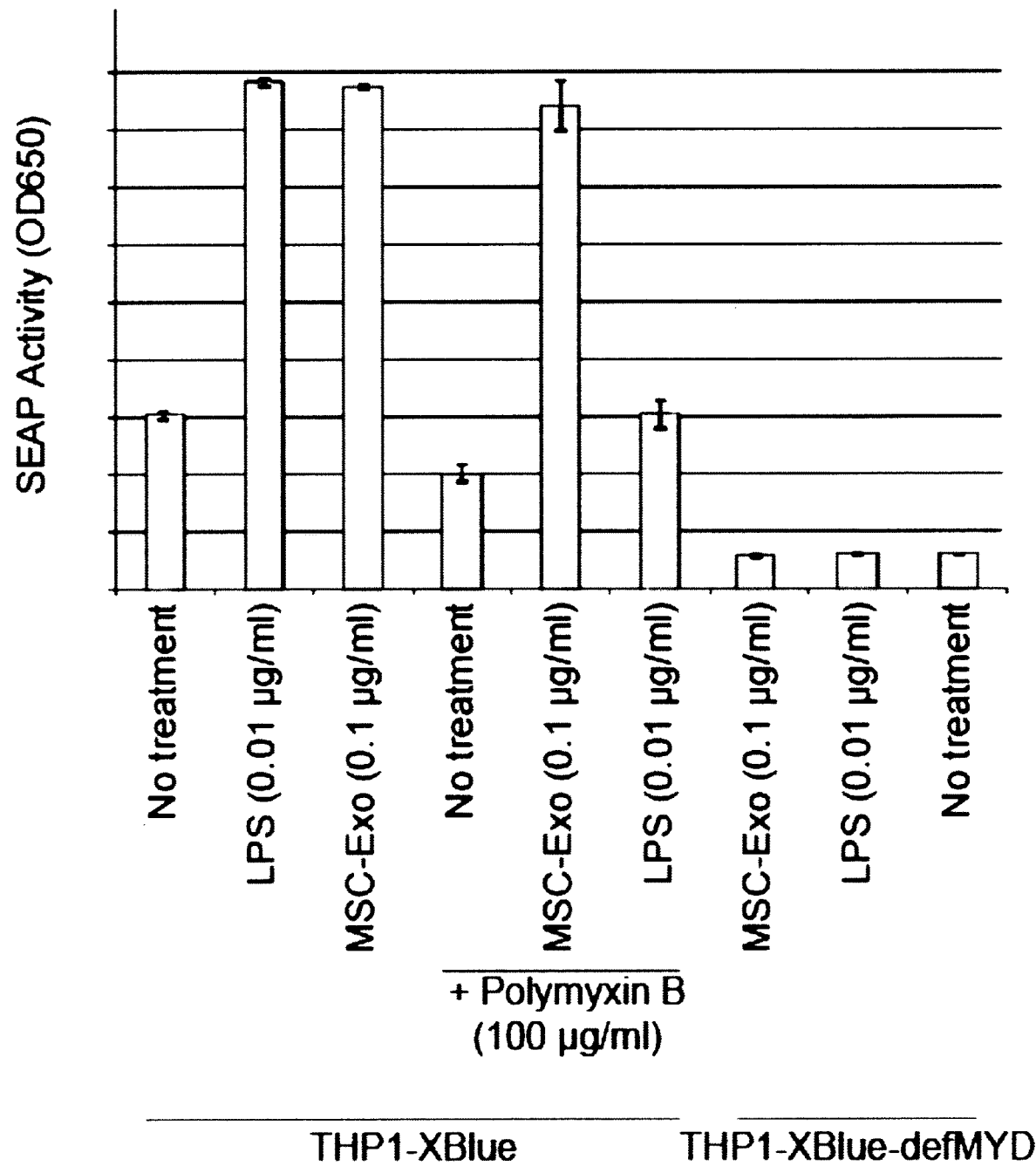
FIG. 7 is a diagram showing that MSC exosome has TLR ligands.
Figure 8:
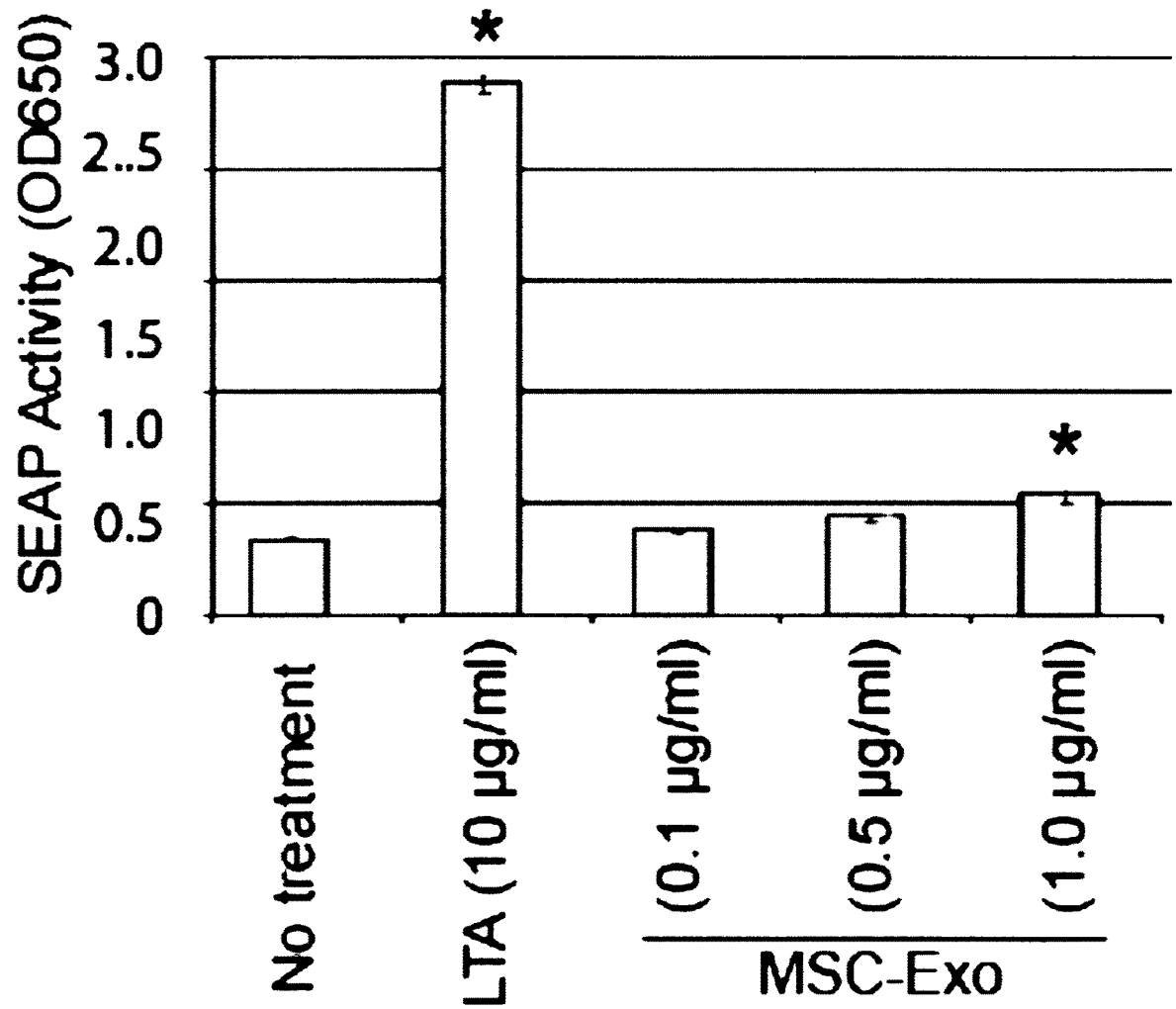
FIG. 8 is a diagram showing that MSC exosome does not activate TLR2.

Since MSC exosomes contain putative ligands for TLR2 and TLR4, they were tested for the potential to activate these receptors using HEK reporter cell lines that are stably transfected with either human TLR2 or TLR4, and a SEAP reporter system (FIG. 7 and FIG. 8). Although MSC exosomes contained endogenous ligands for both TLR2 and TLR4, only TLR4 was activated at 0.1 µg/ml exosomes. There were some small but significant (p<0.01) activation of TLR2 at 1.0 µg/ml exosomes indicating that the capacity for TLR2 activation by MSC exosomes was at least 10 times lower. As TLR4 activation by exosome was not abolished by polymyoxin B, this ruled out LPS contamination in the MSC exosome preparation. Therefore MSC exosomes can activate TLR4 but not TLR2.

Example 20

MSC Exosome Has TLR Ligands—Method

The presence of TLR ligands on MSC exosomes was determined using two cell lines derived from THP-1, a human acute monocytic leukemia cell line known to express most of the human TLRs. The first line is THP1-XBlue with a stably transfected secreted embryonic alkaline phosphatase (SEAP) reporter gene under the transcriptional control of NF-kB promoter. The second line is THP1-XBlue-defMYD that is deficient in MyD88 activity. 105 cells/well were seeded in a 96-well plate and incubated for 24 hours with 10 ηg/ml LPS (*E. coli* 026:B6, Sigma) or 0.1 µg/ml MSC derived exosome (MSC-Exo) with or without polymyoxin B, an antibiotic that binds and inactivates LPS. SEAP level was assayed using a Quanti-Blue (InvivoGen), a fluorescent substrate for alkaline phosphatase.

The results are shown in FIG. 7.

Example 21

MSC Exosome does not Activate TLR2—Methods

The TLR2 activation potential of MSC exosome was assessed using a commercially available HEK293 cell line that has been stably co-transfected with human TLR2, MD2 and CD 14 and an optimized secreted embryonic alkaline phosphatase (SEAP) reporter gene under the control of the NF-κB promoter. This cell line, HEK-Blue-hTLR2 (Invitrogen) was seeded in a 96-well plate at 104 cells/well and incubated for 24 hours with 10 µg/ml lipoteichoic acid (LTA, *Staphylococcus aureus*, Sigma) or 0.1, 0.5 and 1.0 µg/ml MSC derived exosome (MSC-Exo). SEAP level was assayed using a Quanti-Blue (InvivoGen), a fluorescent substrate for alkaline phosphatase.

The results are shown in FIG. 8.

Example 22

MSC Exosome Activates TLR4—Methods

The TLR4 activation potential of MSC exosome was assessed using a commercially available HEK293 cell line that has been stably co-transfected with human TLR4, MD2 and CD 14 and an optimized secreted embryonic alkaline phosphatase (SEAP) reporter gene under the control of the NF-κB promoter. This cell line, HEK-Blue-hTLR4 (Invitrogen) was seeded in a 96-well plate at 104 cells/well and incubated for 24 hours with 10 ηg/ml LPS (*E. coli* 026:B6, Sigma) or 0.1 µg/ml MSC derived exosome (MSC-Exo) with or without polymyoxin B, an antibiotic that binds and inactivates LPS. SEAP level was assayed using a Quanti-Blue (InvivoGen), a fluorescent substrate for alkaline phosphatase.

Figure 9:
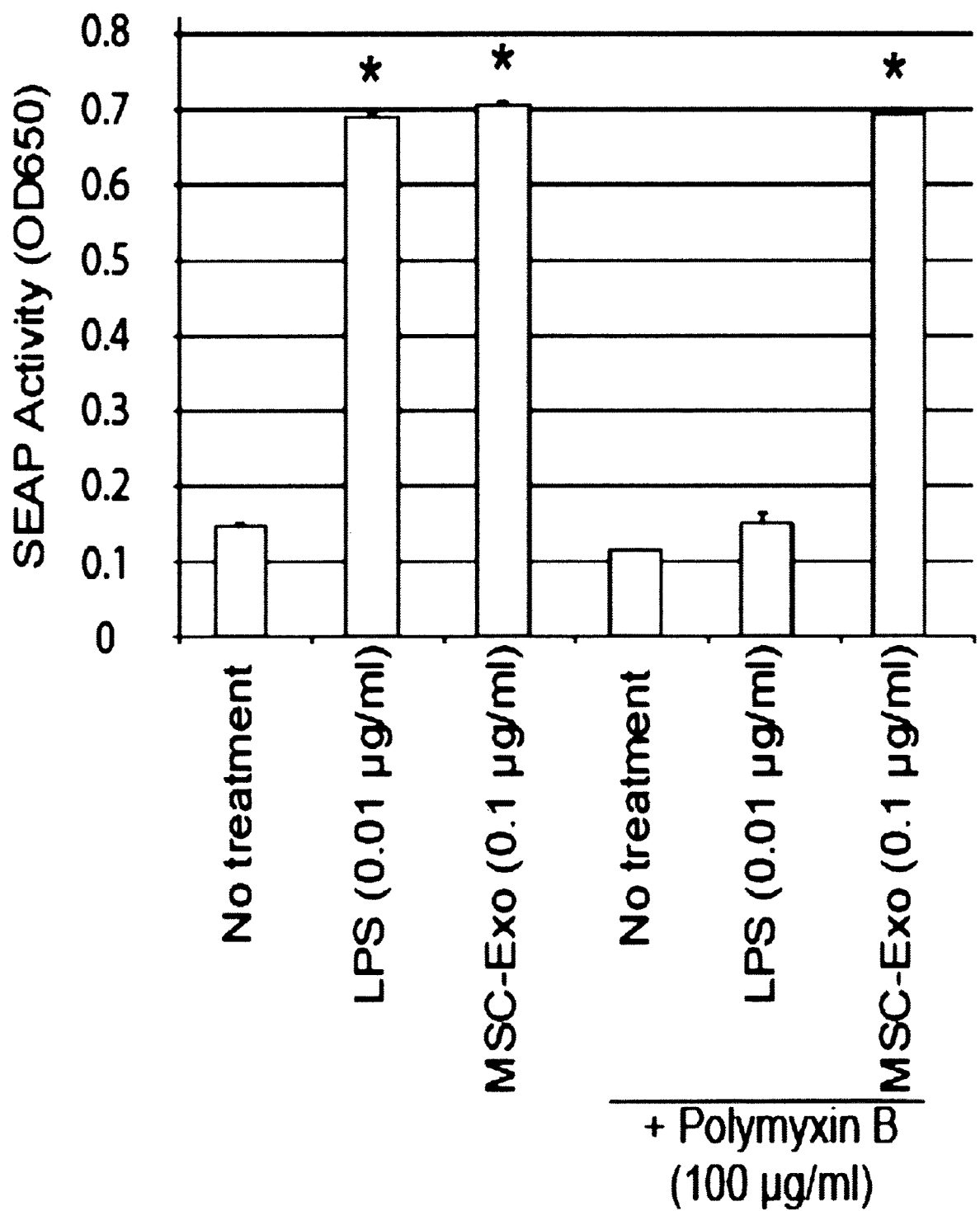
FIG. 9 is a diagram showing that MSC exosome activates TLR4.

The results are shown in FIG. 9.

Example 23

MSC Exosomes Induce Production of Pro- and Anti-Inflammatory Cytokines by THP-1 Cells Methods THP-1 cells were seeded into 24-well culture plates at a concentration of 1×106 cells/ml, stimulated with 10 ηg/ml LPS or 0.1 µg/ml MSC-Exo for 0.5, 1, 3, 6, 12, 24, 48, 72, 96, and 120 hours. The cells were harvested and analysed for cytokine production by real-time quantitative RT-PCR. Total RNA was extracted using the RNeasy Mini kit (QIAGEN) and reverse transcribed using the High Capacity cDNA Reverse Transcription Kit (ABI P/N. 4368813). PCR was performed on a StepOnePlus™ Real-Time PCR Systems (ABI P/N. 4376592) at a total volume of 20 µl in the presence of 10 µl of 2×Fast SYBR® Green Master Mix (ABI, P/N 4385612) reaction buffer, 1 µl of cDNA, and 1 µl Oligonucleotide primers with an initial denaturation step at 95° C. for 10 min followed by 40 cycles of denaturation at 95° C. for 3 s, annealing and elongation at 60° C. for 30 s. The primers used were as follows: IL-1(3 (FW: 5'-CCTGTCCTGCGTGTTGAAAGA-3' (SEQ ID NO: 1); RV: 5'-GGGAACTGGGCAGACTCAAA-3' (SEQ ID NO: 2)), TNF-α (FW: 5'-CCCCAGGGACCTCTCTCTAATC-3' (SEQ ID NO: 3); RV: 5'-GGTTTGCTACAACATGGGC-TACA-3' (SEQ ID NO: 4)), IL-6 (FW: 5'-TCGAGCC-CACCGGGAACGAA-3' (SEQ ID NO: 5); RV: 5'-GCAACTGGACCGAAGGCGCT-3' (SEQ ID NO: 6)), IL-12p40 (FW: 5'-CATGGTGGATGCCGTTCA-3' (SEQ ID NO: 7); RV: 5'-ACCTCCACCTGCCGAGAAT-3' (SEQ ID NO: 8)), IL-10 (FW: 5'-GTGATGCCCCAAGCTGAGA-3' (SEQ ID NO: 9); RV: 5'-CACGGCCTTGCTCTTGTTTT-3' (SEQ ID NO: 10)), TGF-(31 (FW: 5'-CAGCAACAAT-TCCTGGCGATA-3' (SEQ ID NO: 11); RV: 5'-AAGGCGAAAGCCCTCAATTT-3' (SEQ ID NO: 12)), GAPDH (FW: 5'-GTCTTCACCACCATGGAGAAGGCT-3' (SEQ ID NO: 13); RV: 5'-CATGCCAGT-GAGCTTCCCGTTCA-3' (SEQ ID NO: 14)). For each sample, mRNA content was normalized to that of human GAPDH mRNA and is illustrated as n-fold expression in comparison with untreated controls. Each sample was tested in triplicate. Data were analyzed using the comparative ACT method and Applied Biosystems StepOne software Version 2.0.1, according to the manufacturer's instructions.

Results
Effect of MSC Exosomes on Cytokine Production by THP-1 Cells.

Figure 10:
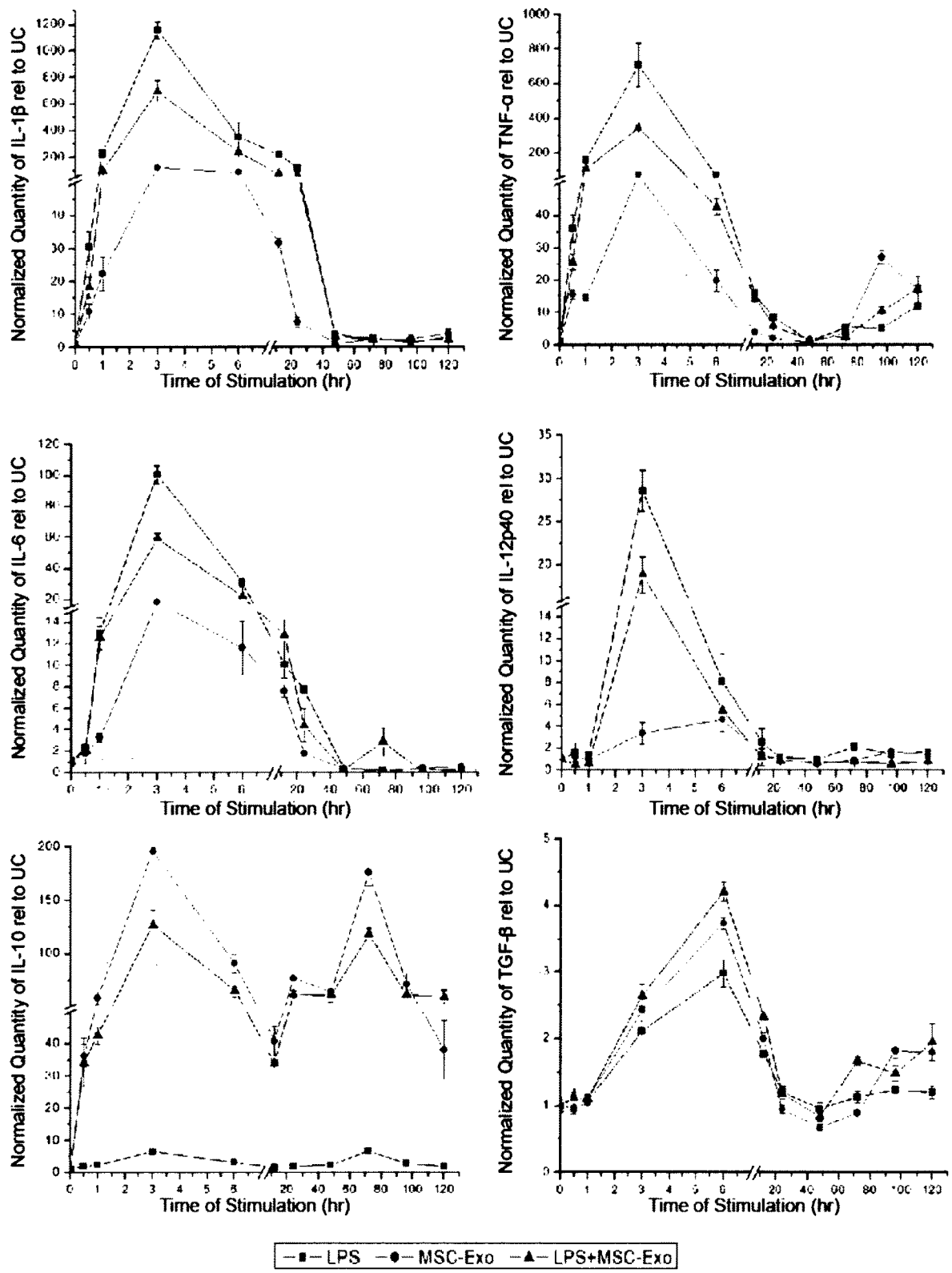
FIG. 10 is a diagram showing that MSC exosome induce production of pro- and anti-inflammatory cytokines by THP-1 cells.

Since TLRs are a major class of receptors that regulate activation of the innate immunity and MSC exosomes can activate TLRs in human monocytic cells, we determined if this activation leads to production of cytokines (FIG. 10).

MSC exosomes induced a biphasic production of pro- and anti-inflammatory cytokines that peaked at 3 and 72-96 hours, respectively.

Example 24

Modulation of Adaptive Immunity by MSC Exosome

The activation of TLRs and induction of pro- and anti-inflammatory cytokines by MSC exosome suggest that MSC exosomes could modulate adaptive immunity. Specifically, we examine if MSC exosomes have any effects on Treg or Th17 differentiation. Treg refers to a subpopulation of T cells known as Regulatory T cells or suppressor T cells[12]. They downregulate the immune system and maintain tolerance to self-antigens. These cells have been used in immunotherapy for immune diseases such as allergy and asthma, diabetes, transplant rejection etc 13 14. Th17 cells are CD4+ memory T cells and are defined by their signature secretion of IL-17 cytokines. They are thought to be central to the pathogenesis of autoimmune disease[15].

Figure 11A:
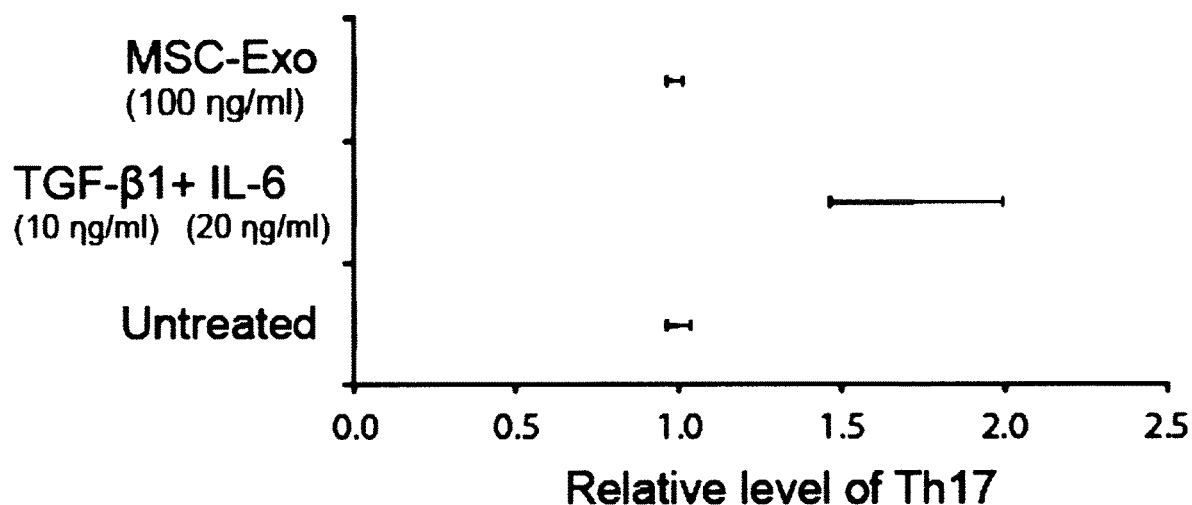
FIG. 11 is a diagram showing that inducing differentiation of CD4+ mouse T cells into either Treg (a) or Th17 cells (b).
Figure 11B:
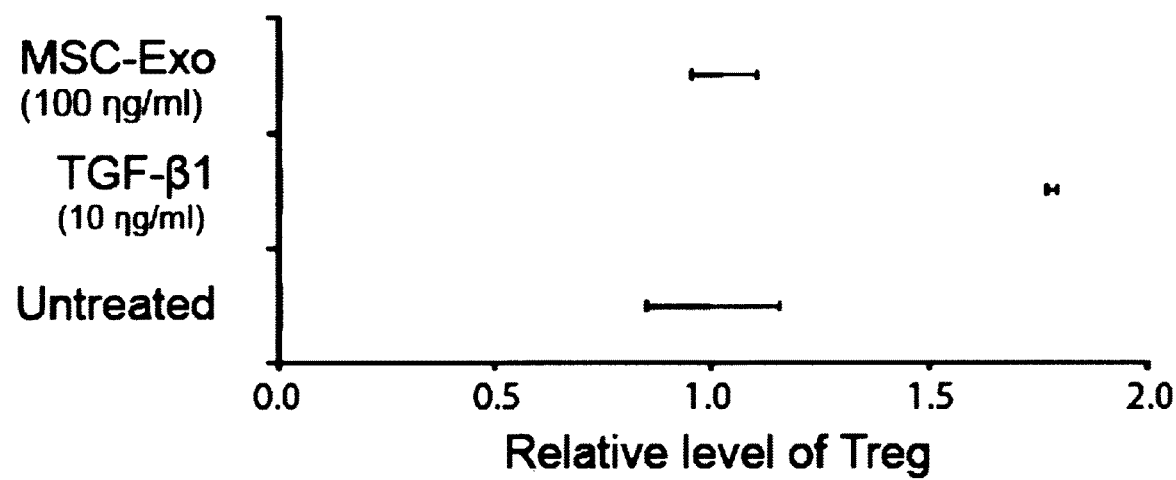

To test the effects of MSC exosomes on differentiation of CD4+ mouse T cells into either Treg or Th17 cells, CD4+ mouse cells were incubated with MSC exosomes. As positive controls, CD4+ mouse cells were induced to differentiate into Treg cells by TGF-β1 and into Th17 cells by IL-6 & TGF-β1 either exerted no effects on the differentiation of CD4+ mouse T cells into either CD4+CD25+Foxp3+ Treg or Th17 cells (FIG. 11).

Example 25

Inducing Differentiation of CD4+ Mouse T Cells into Either Treg (a) or Th17 Cells (b)

Murine splenocytes were prepared from 6 to 8-week-old BALB/C mice as previously described[16]. Briefly, mouse spleens were removed, minced and strained. Erythrocytes were then lysed. CD4+ cells were harvested using a FITC-conjugated Rat anti-mouse CD4 antibody with the EasySep FITC Selection Kit (StemCell Technologies) and the purity was verified by flow cytometry to be >95%. Purified CD4$^+$ T cells were activated using anti-CD3 mAb and 5 μg/ml anti-CD28 mAb.

a) For Treg differentiation: the culture medium was supplemented with 10 ηg/ml rhTGF-β1 or 0.1 μg/ml MSC-Exo. After 6 days, the number of Treg cells defined as CD4+, CD25+ and mouse Foxp3+ cells were determined by FACS using standard antibody staining techniques.

b) For Th17 differentiation, the culture medium was supplemented with 20 ηg/ml rIL-6 & 1 ηg/ml rhTGF-β1 or 0.1 μg/ml MSC-Exo. After 6 days, the number of Th17 cells defined as CD4+, IL17a+ cells were determined by FACS using standard antibody staining techniques.

Treg and Th17 cells in a and b were normalized to the untreated cells.

Example 26

Modulation of Adaptive Immunity by MSC Exosome

Figure 12A:
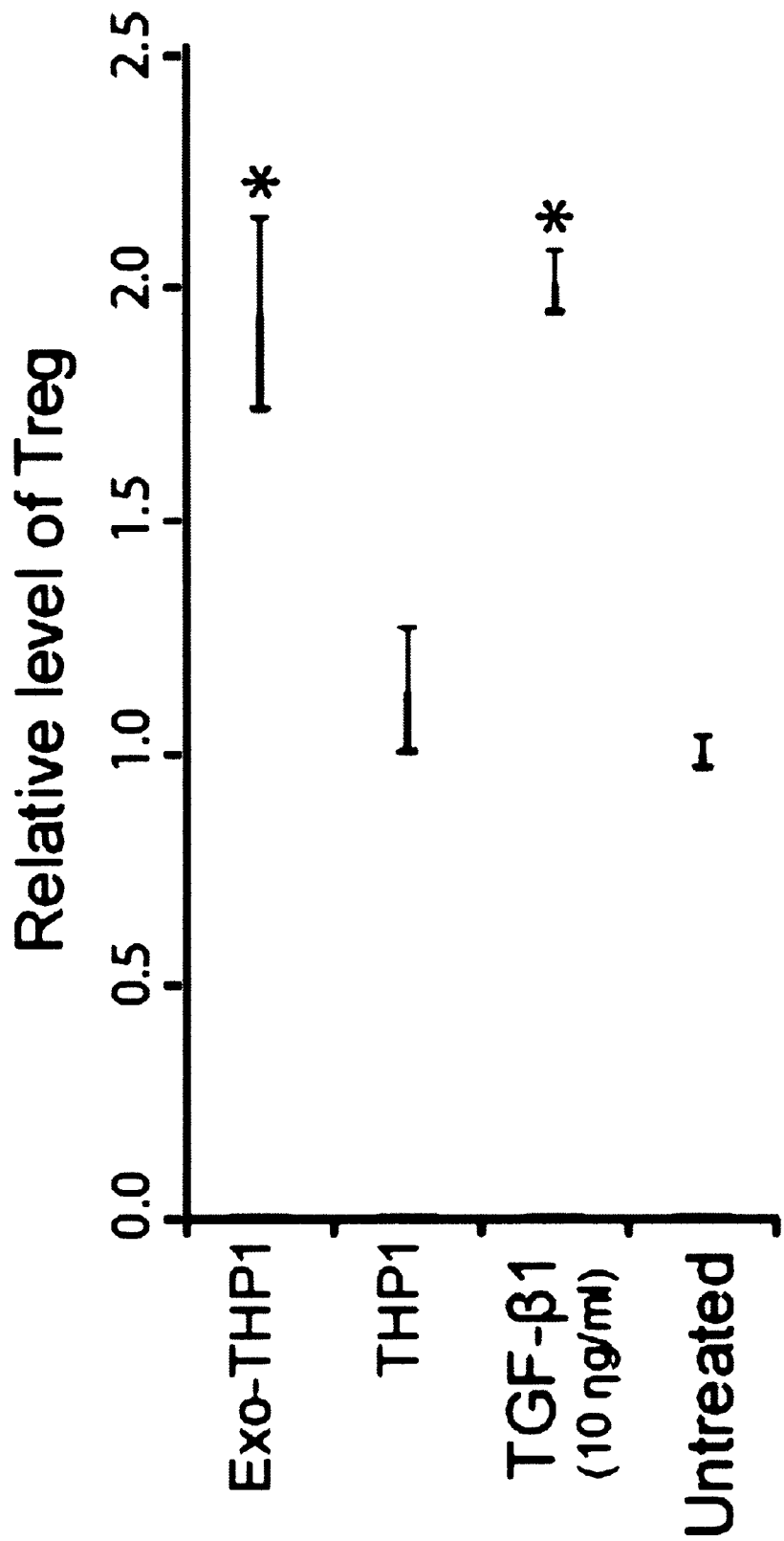
FIG. 12A and FIG. 12B are diagrams showing modulating adaptive immunity via innate immunity.
Figure 12B:
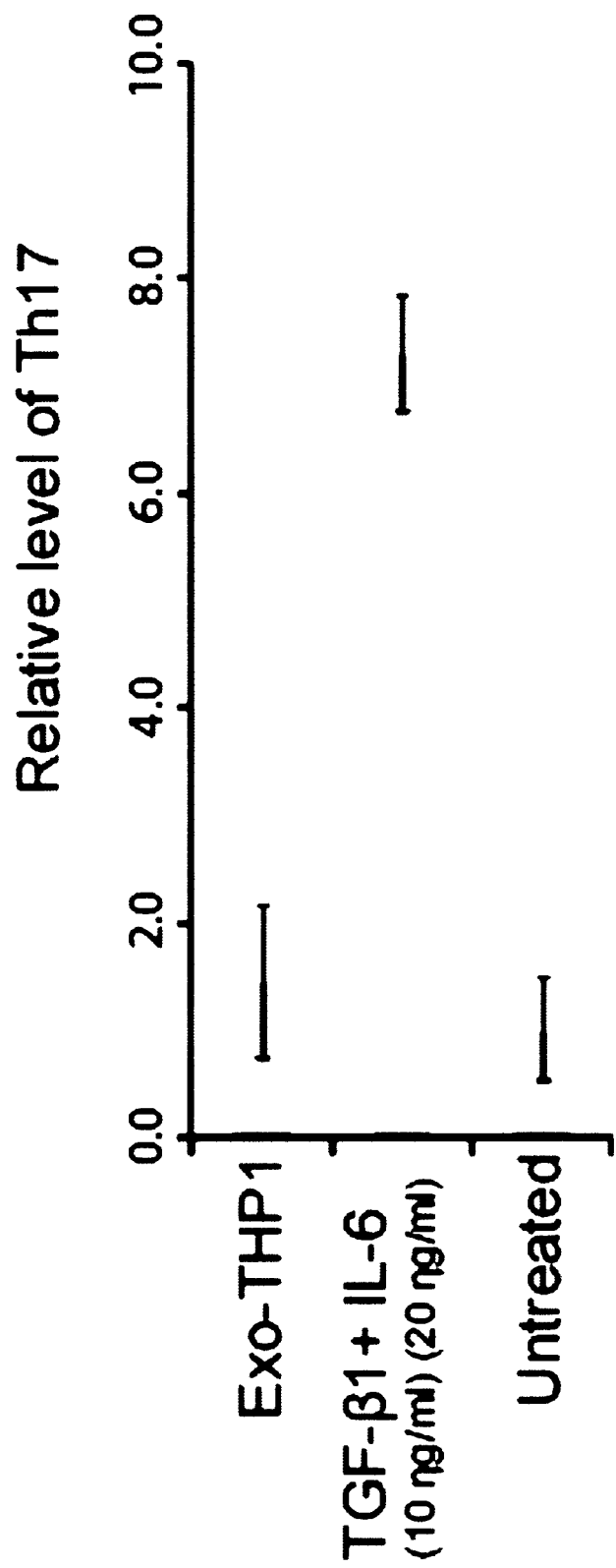

Since MSC exosomes exert a profound activation effect on THP-1 cells and innate immunity plays a central role in modulating adaptive immune response, we hypothesized that exosome could modulate adaptive immunity via its effects on innate immunity. To test this hypothesis, we repeated the experiment described in FIG. 11 with some modifications. During differentiation of the CD4+ T cells to either Treg or TH17 cells, the T cells were incubated with THP-1 cells that had been exposed to exosomes for 6 days (FIG. 12). As positive controls, the T cells were incubated with TGF-β1 or rIL-6+ TGF-β1, respectively. THP-1 cells that had been exposed to MSC exosomes for 48 hours induced T cell differentiation into Tregs but not TH17 cells, suggesting that MSC exosomes could induce an immunosuppressive but not a pro-inflammatory T cell response.

Example 27

Modulating Adaptive Immunity Via Innate Immunity

CD4$^+$ mouse T cells were purified and activated as described in FIG. 11.

a) For Treg differentiation: the culture medium was supplemented with 10 ηg/ml rhTGF-β1, THP-1 cells or THP-1 cells exposed to 0.1 μg/ml MSC exosomes for 48 hours. The THP-1 cells added at a ratio of 1 THP-1 to 1000 CD4$^+$ mouse T cells. After 6 days, the number of Treg cells defined as CD4+, CD25+ and mouse Foxp3+ cells were determined by FACS using standard antibody staining techniques.

b) For Th17 differentiation, the culture medium was supplemented with 20 ηg/ml rIL-6 & 1 ηg/ml rhTGF-β1 or THP-1 cells exposed to 0.1 μg/ml MSC exosomes for 48 hours. The THP-1 cells added at a ratio of 1 THP-1 to 1000 CD4$^+$ mouse T cells. After 6 days, the number of Th17 cells defined as CD4+, IL17a+ cells were determined by FACS using standard antibody staining techniques.

Treg and Th17 cells in a and b were normalized to the untreated cells.

Example 28

MSC Exosome Concanavalin A-activated Lymphocyte Proliferation Assay

Figure 13:
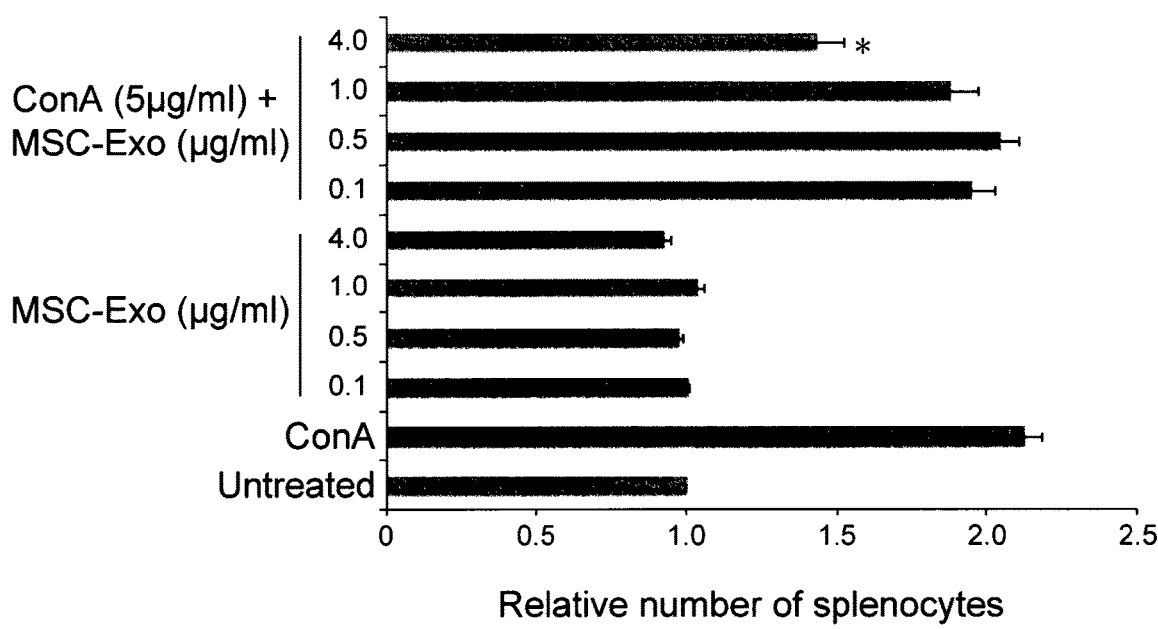
FIG. 13 is a diagram showing a concanavalin A-activated lymphocyte proliferation assay for exosomes.

MSC exosomes may be assessed by their ability to inhibit proliferation of Concanavalin A-activated lymphocytes. See FIG. 13.

Mouse splenocytes were isolated and labeled with carboxyfluorescein succinimidyl ester (CFSE). The CFSE-labeled splenocytes were incubated with different concentration of MSC exosomes (0.1, 0.5, 1 and 4 μg/ml) in the presence or absence of 5 μg/ml Concanavalin A (ConA) for 3 days.

MSC exosomes were prepared as previously described (Lai et al, below). The number of fluorescent cells for each treatment group was quantitated by FACS. Data were normalized to the untreated control and presented as mean (±SD) of triplicate samples.

MSC-Exo did not affect proliferation of splenocytes (p>0.05) and 4.0 µg/ml MSC-Exo significantly inhibited ConA-stimulated splenocytic proliferation (* p<0.01).

Reference is made to R. C. Lai, F. Arslan, M. M. Lee, N. S. Sze, A. Choo, T. S. Chen, M. Salto-Tellez, L. Timmers, C. N. Lee, R. M. El Oakley, G. Pasterkamp, D. P. de Kleijn, S. K. Lim, Exosome secreted by MSC reduces myocardial ischemia/reperfusion injury, Stem Cell Res, 4 (2010) 214-222.

Example 29

Conclusions (for Examples 19 to 28)

MSC exosomes can activate pro- and anti-inflammatory innate immune responses but can induce suppressive adaptive immune responses only indirectly via the innate immune system. They do not activate inflammatory adaptive immune responses directly or indirectly.

Therefore MSC exosomes could be used to enhance tissue repair and inhibit disease progression in autoimmune diseases such as GVHD, Crohn's disease, SLE, Diabetes Type 1, Multiple Sclerosis, ALS.

Example 30

References (for Examples 19 to 29)

1 Kawai, T. & Akira, S. The roles of TLRs, RLRs and NLRs in pathogen recognition ARTICLE. International Immunology 21, 317-337, doi:10.1093/intimm/dxp017 (2009).
2 Devitt, A. & Marshall, L. J. The innate immune system and the clearance of apoptotic cells. Journal of Leukocyte Biology 90, 447-457, doi:10.1189/jlb.0211095 (2011).
3 Iwasaki, A. & Medzhitov, R. Regulation of Adaptive Immunity by the Innate Immune System. Science 327, 291-295, doi:10.1126/science. 1183021 (2010).
4 Yu, L., Wang, L. & Chen, S. Endogenous toll-like receptor ligands and their biological significance. Journal of Cellular and Molecular Medicine 14, 2592-2603, doi: 10.1111/j.1582-4934.2010.01127.x (2010).
5 Nauta, A. J. & Fibbe, W. E. Immunomodulatory properties of mesenchymal stromal cells. Blood 110, 3499-3506, doi:10.1182/blood-2007-02-069716 (2007).
6 Le Blanc, K. et al. Mesenchymal stem cells for treatment of steroid-resistant, severe, acute graft-versus-host disease: a phase II study. The Lancet 371, 1579-1586 (2008).
7 García-Olmo, D. et al. A Phase I Clinical Trial of the Treatment of Crohn's Fistula by Adipose Mesenchymal Stem Cell Transplantation. Diseases of the Colon & Rectum 48, 1416-1423 1410.1007/s10350-10005-10052-10356 (2005).
8 Singer, N. G. & Caplan, A. I. Mesenchymal Stem Cells: Mechanisms of Inflammation. Annual Review of Pathology: Mechanisms of Disease 6, 457-478, doi:10.1146/annurev-pathol-011110-130230 (2011).
9 Timmers, L. et al. Reduction of myocardial infarct size by human mesenchymal stem cell conditioned medium. Stem Cell Research 1, 129-137 (2008).
10 Timmers, L. et al. Human mesenchymal stem cell-conditioned medium improves cardiac function following myocardial infarction. Stem Cell Research 6, 206-214, doi:10.1016/j.scr.2011.01.001 (2011).
11 Lai, R. C. et al. Exosome secreted by MSC reduces myocardial ischemia/reperfusion injury. Stem Cell Res 4, 214-222, doi:S1873-5061(09)00141-X [pii] 10.1016/j.scr.2009.12.003 (2010).
12 Vignali, D. A. A., Collison, L. W. & Workman, C. J. How regulatory T cells work. Nat Rev Immunol 8, 523-532 (2008).
13 Riley, J. L., June, C. H. & Blazar, B. R. Human T Regulatory Cell Therapy: Take a Billion or So and Call Me in the Morning. Immunity 30, 656-665 (2009).
14 Nandakumar, S., Miller, C. & Kumaraguru, U. T regulatory cells: an overview and intervention techniques to modulate allergy outcome. Clinical and Molecular Allergy 7, 5 (2009).
15 Perry, D., Peck, A. B., Carcamo, W. C., Morel, L. & Nguyen, C. Q. The Current Concept of T H 17 Cells and Their Expanding Role in Systemic Lupus Erythematosus. Arthritis 2011, doi:10.1155/2011/810649 (2011).
16 Su, P. F. et al. Dioscorea phytocompounds enhance murine splenocyte proliferation ex vivo and improve regeneration of bone marrow cells in vivo. Evid Based Complement Alternat Med 2011, 731308, doi:10.1093/ecam/neq032 (2011).

REFERENCES

1. Pan, B. T. & Johnstone, R. M. Fate of the transferrin receptor during maturation of sheep reticulocytes in vitro: selective externalization of the receptor. *Cell* 33, 967-978 (1983).
2. Thery, C., Ostrowski, M. & Segura, E. Membrane vesicles as conveyors of immune responses. *Nat Rev Immunol* 9, 581-593 (2009).
3. Fevrier, B. & Raposo, G. Exosomes: endosomal-derived vesicles shipping extracellular messages. *Curr Opin Cell Biol* 16, 415-421 (2004).
4. Keller, S., Sanderson, M. P., Stoeck, A. & Altevogt, P. Exosomes: from biogenesis and secretion to biological function. *Immunol Lett* 107, 102-108 (2006).
5. Zitvogel, L., et al. Eradication of established murine tumors using a novel cell-free vaccine: Dendritic cell-derived exosomes. *Nature Medicine* 4, 594-600 (1998).
6. Wolfers, J., et al. Tumor-derived exosomes are a source of shared tumor rejection antigens for CTL cross-priming. *Nature Medicine* 7, 297-303 (2001).
7. Skokos, D., et al. Mast cell-derived exosomes induce phenotypic and functional maturation of dendritic cells and elicit specific immune responses in vivo. *Journal of Immunology* 170, 3037-3045 (2003).
8. Taylor, D. D. & Gercel-Taylor, C. Tumour-derived exosomes and their role in cancer-associated T-cell signalling defects. *British Journal of Cancer* 92, 305-311 (2005).
9. Lai, R. C., et al. Exosome secreted by MSC reduces myocardial ischemia/reperfusion injury. *Stem Cell Res* 4, 214-222 (2010).
10. Lai, R. C., et al. Derivation and characterization of human fetal MSCs: an alternative cell source for large-scale production of cardioprotective microparticles. *J Mol Cell Cardiol* 48, 1215-1224 (2010).
11. Sze, S. K., et al. Elucidating the secretion proteome of human embryonic stem cell-derived mesenchymal stem cells. *Mol Cell Proteomics* 6, 1680-1689 (2007).
12. Chen, T. S., et al. Mesenchymal stem cell secretes microparticles enriched in pre-microRNAs. *Nucleic Acids Res* 38, 215-224 (2010).
13. Lian, Q., et al. Derivation of Clinically Compliant MSCs from CD105+, CD24− Differentiated Human ESCs. *Stem Cells* 25, 425-436 (2007).
14. Thomas, P. D., et al. PANTHER: a library of protein families and subfamilies indexed by function. *Genome Res* 13, 2129-2141 (2003).

15. Thomas, P. D., et al. Applications for protein sequence-function evolution data: mRNA/protein expression analysis and coding SNP scoring tools. *Nucleic Acids Res* 34, W645-650 (2006).
16. Simons, M. & Raposo, G. Exosomes—vesicular carriers for intercellular communication. *Curr Opin Cell Biol* 21, 575-581 (2009).
17. Barry, F. P. & Murphy, J. M. Mesenchymal stem cells: clinical applications and biological characterization. *Int J Biochem Cell Biol* 36, 568-584 (2004).
18. Pilkis, S. J., El-Maghrabi, M. R., Pilkis, J. & Claus, T. Inhibition of fructose-1,6-bisphosphatase by fructose 2,6-bisphosphate. *J Biol Chem* 256, 3619-3622 (1981).
19. Bando, H., et al. Phosphorylation of the 6-phosphofructo-2-kinase/fructose 2,6-bisphosphatase/PFKFB3 family of glycolytic regulators in human cancer. *Clin Cancer Res* 11, 5784-5792 (2005).
20. Penefsky, H. S. Mechanism of inhibition of mitochondrial adenosine triphosphatase by dicyclohexylcarbodiimide and oligomycin: relationship to ATP synthesis. *Proc Natl Acad Sci USA* 82, 1589-1593 (1985).
21. Tanaka, K. The proteasome: overview of structure and functions. *Proc Jpn Acad Ser B Phys Biol Sci* 85, 12-36 (2009).
22. Newman, R. H., Whitehead, P., Lally, J., Coffer, A. & Freemont, P. 20S human proteasomes bind with a specific orientation to lipid monolayers in vitro. *Biochim Biophys Acta* 1281, 111-116 (1996).
23. Evgenia Gerasimovskaya, E. K. *Extracellular ATP and adenosine as regulators of endothelial cell function. Implications for health and disease* (2010).
24. Hasko, G., Linden, J., Cronstein, B. & Pacher, P. Adenosine receptors: therapeutic aspects for inflammatory and immune diseases. *Nat Rev Drug Discov* 7, 759-770 (2008).
25. Jacobson, K. A. Introduction to adenosine receptors as therapeutic targets. *Handbook of experimental pharmacology*, 1-24 (2009).
26. Frangogiannis, N. G., Smith, C. W. & Entman, M. L. The inflammatory response in myocardial infarction. *Cardiovasc Res* 53, 31-47 (2002).
27. Davies, A. & Lachmann, P. J. Membrane defense against complement lysis: the structure and biological properties of CD59. *Immunol Res* 12, 258-275 (1993).
28. Simons, M. & Raposo, G. Exosomes—vesicular carriers for intercellular communication. *Current Opinion in Cell Biology* 21, 575-581 (2009).
29. Simpson, R. J., Lim, J. W., Moritz, R. L. & Mathivanan, S. Exosomes: proteomic insights and diagnostic potential. *Expert Rev Proteomics* 6, 267-283 (2009).
30. Raposo, G., et al. B lymphocytes secrete antigen-presenting vesicles. *Journal of Experimental Medicine* 183, 1161-1172 (1996).
31. Valadi, H., et al. Exosome-mediated transfer of mRNAs and microRNAs is a novel mechanism of genetic exchange between cells. *Nat Cell Biol* 9, 654-659 (2007).
32. Schorey, J. S. & Bhatnagar, S. Exosome function: From tumor immunology to pathogen biology. *Traffic* 9, 871-881 (2008).
33. Thery, C., Ostrowski, M. & Segura, E. Membrane vesicles as conveyors of immune responses. *Nature Reviews Immunology* 9, 581-593 (2009).
34. Huber, V., Filipazzi, P., Iero, M., Fais, S. & Rivoltini, L. More insights into the immunosuppressive potential of tumor exosomes. *Journal of Translational Medicine* 6 (2008).
35. Muntasell, A., Berger, A. C. & Roche, P. A. T cell-induced secretion of MHC class II-peptide complexes on B cell exosomes. *EMBO Journal* 26, 4263-4272 (2007).
36. Zeelenberg, I. S., et al. Targeting tumor antigens to secreted membrane vesicles in vivo induces efficient antitumor immune responses. *Cancer Research* 68, 1228-1235 (2008).
37. Zöller, M. Tetraspanins: Push and pull in suppressing and promoting metastasis. *Nature Reviews Cancer* 9, 40-55 (2009).
38. Simpson, R. J., Jensen, S. S. & Lim, J. W. E. Proteomic profiling of exosomes: Current perspectives. *Proteomics* 8, 4083-4099 (2008).
39. Orrenius, S., Gogvadze, V. & Zhivotovsky, B. Mitochondrial Oxidative Stress: Implications for Cell Death. *Annual Review of Pharmacology and Toxicology* 47, 143-183 (2007).
40. Jung, T. & Grune, T. The proteasome and its role in the degradation of oxidized proteins. *IUBMB Life* 60, 743-752 (2008).
41. Stadtman, E. R. & Levine, R. L. Protein oxidation. *Ann N Y Acad Sci* 899, 191-208 (2000).
42. Dunlop, R. A., Brunk, U. T. & Rodgers, K. J. Oxidized proteins: mechanisms of removal and consequences of accumulation. *IUBMB Life* 61, 522-527 (2009).
43. Sohns, W., van Veen, T. A. & van der Heyden, M. A. Regulatory roles of the ubiquitin-proteasome system in cardiomyocyte apoptosis. *Curr Mol Med* 10, 1-13.
44. Willis, M. S., Townley-Tilson, W. H., Kang, E. Y., Homeister, J. W. & Patterson, C. Sent to destroy: the ubiquitin proteasome system regulates cell signaling and protein quality control in cardiovascular development and disease. *Circ Res* 106, 463-478.
45. Tsukamoto, O., Minamino, T. & Kitakaze, M. Functional alterations of cardiac proteasomes under physiological and pathological conditions. *Cardiovasc Res* 85, 339-346 (2010).
46. Ovize, M., et al. Postconditioning and protection from reperfusion injury: where do we stand? Position paper from the Working Group of Cellular Biology of the Heart of the European Society of Cardiology. *Cardiovasc Res* 87, 406-423 (2010).
47. Hausenloy, D. J. & Yellon, D. M. New directions for protecting the heart against ischaemia-reperfusion injury: targeting the Reperfusion Injury Salvage Kinase (RISK)-pathway. *Cardiovasc Res* 61, 448-460 (2004).
48. Pamuk, O. N., et al. Spleen tyrosine kinase inhibition prevents tissue damage after ischemia-reperfusion. *Am J Physiol Gastrointest Liver Physiol* 299, G391-399 (2010).
49. Castellano, G., et al. Therapeutic targeting of classical and lectin pathways of complement protects from ischemia-reperfusion-induced renal damage. *Am J Pathol* 176, 1648-1659 (2010).
50. Busche, M. N., Pavlov, V., Takahashi, K. & Stahl, G. L. Myocardial ischemia and reperfusion injury is dependent on both IgM and mannose-binding lectin. *Am J Physiol Heart Circ Physiol* 297, H1853-1859 (2009).
51. Lai, R. C., et al. Exosome secreted by MSC reduces myocardial ischemia/reperfusion injury. *Stem Cell Res* 4, 214-222 (2010).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of identifying a mesenchymal stem cell exosome with immunomodulatory activity, the method comprising detecting in a mesenchymal stem cell exosome an immunomodulatory activity by: detecting an exosome protein selected from biglycan, endoplasmin, HSP60, HSP70, β-defensin 2, fibrinogen alpha, fibrinogen beta, fibrinogen gamma, fibronectin, tenascin-c, S100A11, S100A13, S100A8, S100A9, and S100P; and detecting activity of the mesenchymal stem cell exosome comprising the protein in an assay for activation of toll-like receptor 4 (TLR4), or for differentiation of THP-1 cells into Tregs, thereby identifying an exosome with immunomodulatory activity.

2. The method of claim 1, wherein the method further comprises detecting the activity of the mesenchymal stem cell exosome comprising the protein in an assay for complement-mediated cell lysis.

3. The method of claim 1, wherein the immunomodulatory activity is immunosuppressive.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctgtcctgc gtgttgaaag a                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggaactggg cagactcaaa                                                20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccccagggac ctctctctaa tc                                             22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtttgctac aacatgggct aca                                            23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgagcccac cgggaacgaa                                                20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcaactggac cgaaggcgct                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catggtggat gccgttca                                                18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acctccacct gccgagaat                                               19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgatgcccc aagctgaga                                               19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacggccttg ctcttgtttt                                              20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagcaacaat tcctggcgat a                                            21

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaggcgaaag ccctcaattt                                              20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcttcacca ccatggagaa ggct                                         24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
catgccagtg agcttcccgt tca                                          23

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Leu Val Tyr
1
```